United States Patent
Gaublomme et al.

(10) Patent No.: US 11,092,607 B2
(45) Date of Patent: Aug. 17, 2021

(54) MULTIPLEX ANALYSIS OF SINGLE CELL CONSTITUENTS

(71) Applicants: THE BROAD INSTITUTE, INC., Cambridge, MA (US); MASSACHUSETTS INSTITUTE OF TECHNOLOGY, Cambridge, MA (US)

(72) Inventors: Jellert Gaublomme, Cambridge, MA (US); Aviv Regev, Cambridge, MA (US)

(73) Assignees: The Board Institute, Inc., Cambridge, MA (US); Massachusetts Institute of Technology, Cambridge, MA (US)

( * ) Notice: Subject to any disclaimer, the term of this patent is extended or adjusted under 35 U.S.C. 154(b) by 0 days.

(21) Appl. No.: 15/771,987

(22) PCT Filed: Oct. 27, 2016

(86) PCT No.: PCT/US2016/059195
§ 371 (c)(1),
(2) Date: Apr. 27, 2018

(87) PCT Pub. No.: WO2017/075265
PCT Pub. Date: May 4, 2017

(65) Prior Publication Data
US 2018/0340939 A1  Nov. 29, 2018

Related U.S. Application Data

(60) Provisional application No. 62/247,656, filed on Oct. 28, 2015.

(51) Int. Cl.
| | | |
|---|---|---|
| *G01N 33/68* | (2006.01) | |
| *G01N 33/58* | (2006.01) | |
| *C12Q 1/6869* | (2018.01) | |
| *C12Q 1/6811* | (2018.01) | |
| *C12Q 1/6823* | (2018.01) | |
| *C12Q 1/683* | (2018.01) | |

(52) U.S. Cl.
CPC ......... *G01N 33/6845* (2013.01); *C12Q 1/683* (2013.01); *C12Q 1/6811* (2013.01); *C12Q 1/6823* (2013.01); *C12Q 1/6869* (2013.01); *G01N 33/58* (2013.01); *C12Q 2535/122* (2013.01); *C12Q 2563/179* (2013.01); *G01N 2458/10* (2013.01)

(58) Field of Classification Search
CPC ............... G01N 33/6845; G01N 33/58; G01N 2458/10; C12Q 1/6811; C12Q 1/6823; C12Q 1/683; C12Q 1/6869; C12Q 2535/122; C12Q 2563/179
See application file for complete search history.

(56) References Cited

U.S. PATENT DOCUMENTS

| | | |
|---|---|---|
| 4,683,195 A | 7/1987 | Mullis et al. |
| 4,683,202 A | 7/1987 | Mullis et al. |
| 5,451,500 A | 9/1995 | Stapleton et al. |
| 6,033,880 A | 3/2000 | Haff et al. |
| 6,524,456 B1 | 2/2003 | Ramsey et al. |
| 6,617,145 B2 | 9/2003 | Boone et al. |
| 7,041,481 B2 | 5/2006 | Anderson et al. |
| 7,129,091 B2 | 10/2006 | Ismagilov et al. |
| 7,708,949 B2 | 5/2010 | Stone et al. |
| RE41,780 E | 9/2010 | Anderson et al. |
| 8,273,573 B2 | 9/2012 | Ismagilov et al. |
| 8,304,193 B2 | 11/2012 | Ismagilov et al. |
| 8,329,407 B2 | 12/2012 | Ismagilov et al. |
| 8,658,430 B2 | 2/2014 | Miller et al. |
| 8,697,359 B1 | 4/2014 | Zhang |
| 8,771,945 B1 | 7/2014 | Zhang |
| 8,795,965 B2 | 8/2014 | Zhang |
| 8,822,148 B2 | 9/2014 | Ismagliov |
| 8,835,358 B2 | 9/2014 | Fodor et al. |
| 8,865,406 B2 | 10/2014 | Zhang et al. |
| 8,871,445 B2 | 10/2014 | Cong et al. |
| 8,889,083 B2 | 11/2014 | Ismagilov et al. |
| 8,889,356 B2 | 11/2014 | Zhang |
| 8,889,418 B2 | 11/2014 | Zhang et al. |
| 8,895,308 B1 | 11/2014 | Zhang et al. |
| 8,906,616 B2 | 12/2014 | Zhang et al. |

(Continued)

FOREIGN PATENT DOCUMENTS

| | | |
|---|---|---|
| EP | 2047910 A2 | 4/2009 |
| EP | 2 764 103 A2 | 8/2014 |

(Continued)

OTHER PUBLICATIONS

"Markman Order In re Certain Microfluidic Systems and Components Thereof and Products Containing Same", Docket Alarm, pp. 1-6, Oct. 31, 2018.
"Molecular and Genomics Core Facility Equipment", Molecular and Genomics Core Facility, pp. 1-7, 2018.
"N,N'-Methylenebis(acrylamide)", 146072 Sigma-Aldrich, CAS No. 110-26-9, 2018.
"Neuroscience 2017 Program", Society for Neuroscience, pp. 1-2, 2017.
"Notice of Intent to Certify Sole Source", Sole Source Certification No. SS5098 for Bio-Rad ddSeq Single Cell Isolation System and associated accessories, pp. 1-5, Jun. 5, 2017.

(Continued)

*Primary Examiner* — Robert H Havlin
(74) *Attorney, Agent, or Firm* — Johnson, Marcou, Isaacs & Nix, LLC; F. Brent Nix, Esq.; Michael B. Scher, Esq.

(57) ABSTRACT

The present invention relates to methods for high multiplex protein or cellular constituent analysis in single cells or single isolated aggregations of cellular constituents. The methods provide for embedding cells or isolated aggregations of cellular constituents in a hydrogel mesh and labeling of cellular constituents with labeling ligands linked to a nucleic acid tag. Cellular constituents can be determined using sequencing methods.

18 Claims, 21 Drawing Sheets

(56) References Cited

U.S. PATENT DOCUMENTS

| | | |
|---|---|---|
| 8,932,814 B2 | 1/2015 | Cong et al. |
| 8,945,839 B2 | 2/2015 | Zhang |
| 8,993,233 B2 | 3/2015 | Zhang et al. |
| 8,999,641 B2 | 4/2015 | Zhang et al. |
| 9,089,844 B2 | 7/2015 | Hiddessen et al. |
| 9,126,160 B2 | 9/2015 | Ness et al. |
| 9,216,392 B2 | 12/2015 | Hindson et al. |
| 9,290,808 B2 | 3/2016 | Fodor et al. |
| 9,290,809 B2 | 3/2016 | Fodor et al. |
| 9,315,857 B2 | 4/2016 | Fu et al. |
| 9,347,059 B2 | 5/2016 | Saxonov |
| 9,388,465 B2 | 7/2016 | Hindson et al. |
| 9,500,664 B2 | 11/2016 | Ness et al. |
| 9,567,631 B2 | 2/2017 | Hindson et al. |
| 9,567,645 B2 | 2/2017 | Fan et al. |
| 9,567,646 B2 | 2/2017 | Fan et al. |
| 9,598,736 B2 | 3/2017 | Fan et al. |
| 9,636,682 B2 | 5/2017 | Hiddessen et al. |
| 9,637,799 B2 | 5/2017 | Fan et al. |
| 9,644,204 B2 | 5/2017 | Hindson et al. |
| 9,649,635 B2 | 5/2017 | Hiddessen et al. |
| 9,689,024 B2 | 6/2017 | Hindson et al. |
| 9,695,468 B2 | 7/2017 | Hindson et al. |
| 9,708,654 B2 | 7/2017 | Hunicke-Smith et al. |
| 9,708,659 B2 | 7/2017 | Fodor et al. |
| 9,816,121 B2 | 11/2017 | Agresti et al. |
| 9,816,137 B2 | 11/2017 | Fodor et al. |
| 9,826,137 B2 | 11/2017 | Yokomizo |
| 9,845,502 B2 | 12/2017 | Fodor et al. |
| 9,856,530 B2 | 1/2018 | Hindson et al. |
| 9,885,034 B2 | 2/2018 | Saxonov |
| 10,144,950 B2 | 12/2018 | Nolan |
| 2002/0172965 A1 | 11/2002 | Kamb et al. |
| 2005/0172476 A1 | 8/2005 | Stone et al. |
| 2006/0163385 A1 | 7/2006 | Link et al. |
| 2007/0003442 A1 | 1/2007 | Link et al. |
| 2007/0184489 A1 | 8/2007 | Griffiths et al. |
| 2007/0195127 A1 | 8/2007 | Ahn et al. |
| 2008/0003142 A1 | 1/2008 | Link et al. |
| 2008/0014589 A1 | 1/2008 | Link et al. |
| 2009/0005254 A1 | 1/2009 | Griffiths et al. |
| 2009/0042737 A1 | 2/2009 | Katz et al. |
| 2009/0131543 A1 | 5/2009 | Weitz et al. |
| 2010/0002241 A1 | 1/2010 | Hirose |
| 2010/0022414 A1 | 1/2010 | Link et al. |
| 2010/0137163 A1 | 6/2010 | Link et al. |
| 2010/0172803 A1 | 7/2010 | Stone et al. |
| 2011/0319298 A1 | 12/2011 | Benner et al. |
| 2012/0122714 A1 | 5/2012 | Samuels et al. |
| 2012/0208705 A1 | 8/2012 | Steemers et al. |
| 2012/0219947 A1 | 8/2012 | Yurkovetsky et al. |
| 2012/0220494 A1 | 8/2012 | Samuels et al. |
| 2013/0274117 A1 | 10/2013 | Church et al. |
| 2014/0155295 A1 | 6/2014 | Hindson et al. |
| 2014/0170753 A1 | 6/2014 | Zhang |
| 2014/0179006 A1 | 6/2014 | Zhang |
| 2014/0179770 A1 | 6/2014 | Zhang et al. |
| 2014/0186843 A1 | 7/2014 | Zhang et al. |
| 2014/0186919 A1 | 7/2014 | Zhang et al. |
| 2014/0186958 A1 | 7/2014 | Zhang et al. |
| 2014/0189896 A1 | 7/2014 | Zhang et al. |
| 2014/0227787 A1 | 8/2014 | Zhang |
| 2014/0234972 A1 | 8/2014 | Zhang |
| 2014/0235506 A1 | 8/2014 | Hindson et al. |
| 2014/0242664 A1 | 8/2014 | Zhang et al. |
| 2014/0242699 A1 | 8/2014 | Zhang |
| 2014/0242700 A1 | 8/2014 | Zhang et al. |
| 2014/0248702 A1 | 9/2014 | Zhang et al. |
| 2014/0256046 A1 | 9/2014 | Zhang et al. |
| 2014/0256595 A1 | 9/2014 | Link et al. |
| 2014/0273231 A1 | 9/2014 | Zhang et al. |
| 2014/0273232 A1 | 9/2014 | Zhang et al. |
| 2014/0273234 A1 | 9/2014 | Zhang et al. |
| 2014/0287938 A1 | 9/2014 | Zhang et al. |
| 2014/0310830 A1 | 10/2014 | Zhang et al. |
| 2014/0357500 A1 | 12/2014 | Vigneault et al. |
| 2015/0005199 A1 | 1/2015 | Hindson et al. |
| 2015/0011430 A1 | 1/2015 | Saxonov |
| 2015/0144490 A1 | 5/2015 | Deisseroth et al. |
| 2015/0299784 A1 | 10/2015 | Fodor et al. |
| 2018/0030515 A1 | 2/2018 | Regev et al. |
| 2018/0066242 A1 | 3/2018 | Zhang et al. |
| 2019/0177788 A1* | 6/2019 | Hindson ............ C12Q 1/6874 |

FOREIGN PATENT DOCUMENTS

| | | | |
|---|---|---|---|
| EP | 2 771 468 A1 | 9/2014 | |
| EP | 2 784 162 A1 | 10/2014 | |
| WO | 01/189788 A2 | 11/2001 | |
| WO | 02099078 A2 | 12/2002 | |
| WO | 2004/002627 A2 | 1/2004 | |
| WO | 2004002627 A2 | 1/2004 | |
| WO | 2004016767 A2 | 2/2004 | |
| WO | 2004/091763 A2 | 10/2004 | |
| WO | 2005003291 A2 | 1/2005 | |
| WO | 2005/021151 A1 | 3/2005 | |
| WO | 2006/040551 A2 | 4/2006 | |
| WO | 2006/040554 A1 | 4/2006 | |
| WO | 2006/096571 A2 | 9/2006 | |
| WO | 2007/081385 A2 | 7/2007 | |
| WO | 2007/089541 A2 | 8/2007 | |
| WO | 2007089541 A2 | 8/2007 | |
| WO | 2007/133710 A2 | 11/2007 | |
| WO | 2008/063227 A2 | 5/2008 | |
| WO | 2009036379 A2 | 3/2009 | |
| WO | 2011/079176 A2 | 6/2011 | |
| WO | 2013188872 A1 | 12/2013 | |
| WO | 2014/018423 A2 | 1/2014 | |
| WO | WO2014018423 * | 1/2014 | ............ A61K 48/00 |
| WO | 2014026032 A2 | 2/2014 | |
| WO | 2014/047561 A1 | 3/2014 | |
| WO | 2014/047561 A1 | 3/2014 | |
| WO | 2014/085802 A1 | 6/2014 | |
| WO | 2014/093595 A1 | 6/2014 | |
| WO | 2014/093622 A2 | 6/2014 | |
| WO | 2014/093635 A1 | 6/2014 | |
| WO | 2014/093655 A2 | 6/2014 | |
| WO | 2014/093661 A2 | 6/2014 | |
| WO | 2014/093694 A1 | 6/2014 | |
| WO | 2014/093701 A1 | 6/2014 | |
| WO | 2014/093709 A1 | 6/2014 | |
| WO | 2014/093712 A1 | 6/2014 | |
| WO | 2014/093718 A1 | 6/2014 | |
| WO | 2014/204723 A1 | 12/2014 | |
| WO | 2014/204724 A1 | 12/2014 | |
| WO | 2014/204725 A1 | 12/2014 | |
| WO | 2014/204726 A1 | 12/2014 | |
| WO | 2014/204727 A1 | 12/2014 | |
| WO | 2014/204728 A1 | 12/2014 | |
| WO | 2014/204729 A1 | 12/2014 | |
| WO | 2014207245 A1 | 12/2014 | |
| WO | 2015/065964 A1 | 5/2015 | |
| WO | 2016/049024 A2 | 3/2016 | |
| WO | 2016/049163 A2 | 3/2016 | |
| WO | 2016/049258 A2 | 3/2016 | |
| WO | 2016040476 A1 | 3/2016 | |

OTHER PUBLICATIONS

"Nucleic Acid Sample Preparation for Downstream Analyses", GE Healthcare Life Sciences Manual, pp. 1-168, 2009.
"Omniscript Reverse Transcription Handbook", Qiagen, pp. 1-32, Oct. 2010.
"Phosphate-buffered saline (PBS)", pdb.rec8247-, Cold Spring Harbor Protocols (2006).
"Powerful New Tool for Genome Analysis", Georgia Tech Bioinformatics, pp. 1-3, Nov. 14, 2017.
"Q Sepharose High Performance SP Sepharose High Performance", GE Healthcare, Data File 18-1172-88 AB, pp. 1-8, Apr. 2006.
"Research Highlights: Human Cell Atlas", Human Cell Atlas | Broad Institute, pp. 1-4, Jan. 8, 2019.
"Restriction Endonucleases Technical Guide", BioLabs Inc., pp. 1-24, Aug. 2015.

(56) References Cited

OTHER PUBLICATIONS

"Reverse Transcription Reaction Setup—Seven Important Considerations", ThermoFisher Scientific, pp. 1-15, 2018.
"Sequencing Power for Every Scale Systems for every application. For every lab.", Illumina, pp. 1-70, 2016.
"Single-Cell RNA Data Analysis Workflow RNA analysis from single cells using the Illumina Bio-Rad Single-Cell Sequencing Solution with the BaseSpace® SureCellTM RNA Single-Cell App.", illumina | Bio-Rad, pp. 1-4, 2017.
"Single-cell RNAseq (Biorad/Illumina ddSEQ)", UNC School of Medicine, pp. 1-3, 2018.
"SITC 2017 Scientific Highlights—Nov. 11", The Sentinel—The Official Blog of the Society for Immunotherapy of Cancer (SITC)., pp. 1-4, Nov. 12, 2017.
"SureCell VVTA 3' Library Prep Kit Support, Questions & Answers", Illumina, pp. 1-4, 2019.
"SureCell WTA 3' Library Prep Kit for the ddSEQ System", Illumina, pp. 1-6, 2019.
"The Illumina Bio-Rad Single Cell Sequencing Solution", illumina | Bio-Rad, pp. 1-3, 2018.
"The Illumina Bio-Rad Single-Cell Sequencing Solution Robust and scalable single-cell sequencing", illumina | Bio-Rad, pp. 1-4, 2016.
"Top 10 Innovations 2015", The Scientist, pp. 1-12, Dec. 1, 2015.
"Transcriptor Reverse Transcriptase", Roche, Ver. 13, pp. 1-13, Jun. 2017.
"Types of Restriction Endonucleases", pp. 1-2, 2018.
U.S. Office Action issued in copending U.S. Appl. No. 15/453,405, filed Aug. 28, 2018, Aug. 28, 2018, 16 pages.
"University of Mississippi Medical Center, Molecular and Genomics Core Facility, Service Home", pp. 1-2, 2018.
"Genomics Resources Core Facility", Weill Cornell Medicine, pp. 1-5, 2018.
Abate, et al., "Beating Poisson encapsulation statistics using close-packed ordering", Lab Chip, vol. 9, pp. 2628-2631, Accepted: Jul. 24, 2009.
Adamson, et al., "A multiplexed single-cell CRISPR screening platform enables systematic dissection of the unfolded protein response", Cell., vol. 167, Issue 7, pp. 1867-18822, Dec. 15, 2016.
International Search Report and Written Opinion issued in International Application No. PCT/US2015/049178, dated Feb. 22, 2016, 18 pages.
Andersen, et al., "A Quantitative Study of the Human Cerebellum with Unbiased Stereological Techniques", The Journal of comparative neurology, vol. 326, Issue 4, pp. 549-560, Dec. 22, 1992.
Ascoli, et al., "Petilla Terminology: Nomenclature of Features of GABAergic Interneurons of the Cerebral Cortex", Nature reviews Neuroscience, vol. 9, pp. 557-568, Jul. 2008.
International Preliminary Report on Patentability issues in International Application No. PCT/US2015/049178, dated Mar. 23, 2017, 12 pages.
Barany, Francis, "Genetic Disease Detection and DNA Amplification Using Cloned Thermostable Ligase", PNAS, vol. 88, Issue 1, pp. 189-193, Jan. 1991.
Barany, Francis, "The Ligase Chain Reaction in a PCR World", PCR Methods and Applications, vol. 1, pp. 5-16, 1991.
Bar-Joseph, et al., "Genome-Wide Transcriptional Analysis of the Human Cell Cycle Identifies Genes Differentially Regulated in Normal and Cancer Cells", PNAS, vol. 105, Issue 3, pp. 955-960, Jan. 22, 2008.
Barres, et al., "Immunological, Morphological, and Electrophysiological Variation Among Retinal Ganglion Cells Purified by Panning", Neuron, vol. 1, Issue 9, pp. 791-803, Nov. 1988.
Beer, et al., "On-Chip Single-Copy Real-Time Reverse-Transcription PCR in Isolated Picoliter Droplets", Analytical Chemistry, vol. 80, Issue 6, pp. 1854-1858, Mar. 15, 2008.
Bentley, et al., "Accurate whole human genome sequencing using reversible terminator chemistry.", Nature, 456 (7218), pp. 53-59, Nov. 6, 2008.

Berman, et al., "Mapping the Stereotyped Behaviour of Free Moving Fruit Flies", Journal of the Royal Society Interface, vol. 11, Issue 99, 20140672, pp. 1-12, Aug. 20, 2014.
Binladen, et al., "The Use of Coded PCR Primers Enables High-Throughput Sequencing of Multiple Homolog Amplification Products by 454 Parallel Sequencing", PLoS One; vol. 2, Issue 2: e197, pp. 1-9, Feb. 14, 2007.
Bitinaite, et al., "USER™ friendly DNA engineering and cloning method by uracil excision", Nucleic Acids Res., vol. 35, No. 6, pp. 1992-2002, Publised online Mar. 6, 2007.
Black, Chris, "The ChromiumTM System: Linked Read and Single Cell RNA-Seq Applications Powered by GemCode Technology", 10X Genomics, pp. 1-57, Jul. 17, 2017.
Bochet, Christian G., "Photolabile protecting groups and linkers", J. Chem. Soc., Perkin Trans. 1, 2002,0, pp. 125-142, First published as an Advance Article on the Web: Dec. 13, 2001.
Brennecke, et al., "Accounting for Technical Noise in Single-Cell RNA-seq Experiments", Nature methods, vol. 10, Issue 11, 1093-1095, Sep. 22, 2013.
Bringer, et al., "Microfluidic Systems for Chemical Kinetics that Rely on Chaotic Mixing in Droplets", Philosophical Transactions of The Royal Society A Mathematical Physical and Engineering Sciences, vol. 362, Issue 1818, pp. 1087-1104, Jun. 2004.
Britten, et al., "Repeated Sequences in DNA. Hundreds of Thousands of Copies of DNA Sequences have been Incorporated into the Genomes of Higher Organisms", Science, vol. 161, Issue 3841, pp. 529-540, Aug. 9, 1968.
Brouzes, et al., "Droplet Microfluidic Technology for Single-Cell High-Throughput Screening", Proceedings of the National Academy of Sciences, vol. 106, No. 34, pp. 14195-14200, Aug. 25, 2009.
Brown, et al., "Chemical Synthesis and Cloning of a Tyrosine tRNA Gene", Methods in Enzymology, vol. 68, pp. 109-151, 1979.
Buettner, et al., "Computational Analysis of Cell-to-Cell Heterogeneity in Single-Cell RNA-Sequencing Data Reveals Hidden Subpopulations of Cells", Nature Biotechnology, vol. 33, Issue 2, pp. 155-160, Feb. 2015.
International Search Report and Written Opinion for PCT International Application No. PCT/US2016/059195, dated Apr. 7, 2017, 14.
"BD Cytofix/Cytoperm Fixation/Permeabilization Kit", http:l/www.bdbiosciences.com/ds/ab/others/554714_554715_555028_Book_Website.pdf>], in further view of US 2013/0274117 to Church et al., 2014, 23 pages.
Invitation to Pay Additional Fees for PCT International Application No. PCT/US2016/059195, mailed Jan. 27, 2017, 3 pages.
Assarsson, et al., "Homogenous 96-plex PEA Immunoassay Exhibiting High Sensitivity, Specificity, and Excellent Scalability", PLoS One, vol. 9, Issue 4, Apr. 2014 |, 11 pages.
Bendall, et al., "Single-Cell Mass Cytometry of Differential Immune and Drug Responses Across a Human Hematopoietic Continuum", Science, vol. 332, No. 6030, May 6, 2011, 687-696.
Buenrostro, et al., "Single-Cell Chromatin Accessibility Reveals Principles of Regulatory Variation", Nature, vol. 523, No. 7561, Jul. 2015, 486-490.
Buenrostro, et al., "Transposition of Native Chromatin for Fast and Sensitive Epigenomic Profiling of Open Chromatin, DNA-binding Proteins and Nucleosome Position", Nature Methods, vol. 10, No. 12, Dec. 2013, 1213-1218.
Chung, et al., "Structural and Molecular Interrogation of Intact Biological Systems", Nature, vol. 497, No. 7449, May 16, 2013, 332-337.
Cusanovich, et al., "Multiplex Single Cell Profiling of Chromatin Accessibility by Combinatorial Cellular Indexing", Science, vol. 348, No. 6237, May 2015, 910-914.
Fan, et al., "Combinatorial Labeling of Single Cells for Gene Expression Cytometry", Science, vol. 347, Issue 6222, Feb. 6, 2015, 10 pages.
Fredriksson, et al., "Protein Detection Using Proximity-Dependent DNA Ligation Assays", Nature Biotechnology, vol. 20, No. 5, May 2002, 473-477.
Gomez, et al., "Detection of Histone Modifications at Specific Gene Loci in Single Cells in Histological Sections", Nature Methods, vol. 10, No. 2, Feb. 2013, 171-177.

(56) References Cited

OTHER PUBLICATIONS

Gullberg, et al., "Cytokine Detection by Antibody-Based Proximity Ligation", Proceedings of the National Academy of Sciences, vol. 101, No. 22, Jun. 1, 2004, 8420-8424.
Guo, et al., "Droplet Microfluidics for High-throughput Biological Assays", Lab Chip, vol. 12, No. 12, 2012, 2146-2155.
Gustafsdottir, et al., "In Vitro Analysis of DNA-Protein Interactions by Proximity Ligation", Proceedings of National Academy of Sciences, vol. 104, No. 9, Feb. 27, 2007, 3067-3072.
Hammond, et al., "Profiling Cellular Protein Complexes by Proximity Ligation with Dual Tag Microarray Readout", PLoS One, vol. 7, Issue 7, Jul. 2012, 9 pages.
Islam, et al., "Quantitative Single-Cell RNA-seq with Unique Molecular Identifiers", Nature Methods, vol. 11, Issue 2, Feb. 2014, 163-166.
Janssen, et al., "Nucleic Acids for Ultra-Sensitive Protein Detection", Sensors, vol. 13, 2013, 1353-1384.
Kantlehner, et al., "A High-Throughput DNA Methylation Analysis of a Single Cell", Nucleic Acids Research, vol. 39, No. 7, 2011, 9 pages.
Kivioja, et al., "Counting Absolute Number of Molecules Using Unique Molecular Identifiers", Nature Methods, vol. 9, 2012, 72-74.
Klein, et al., "Droplet Barcoding for Single-Cell Transcriptomics Applied to Embryonic Stem Cells", Cell, vol. 161, No. 5, May 21, 2015, 1187-1201.
Leuchowius, et al., "Flow Cytometric in Situ Proximity Ligation Analyses of Protein Interactions and Post-Translational Modification of the Epidermal Growth Factor Receptor Family", Cytometry Part A, vol. 75, No. 10, 2009, 833-839.
Lorthongpanich, et al., "Single-Cell DNA-Methylation Analysis Reveals Epigenetic Chimerism in Preimplantation Embryos", Science, vol. 341, No. 6150, Sep. 2013, 1110-1112.
Lundberg et al. "Homogeneous Antibody-Based Proximity Extension Assays Provide Sensitive and Specific Detection of Low-Abundant Proteins in Human Blood", Nucleic Acids Research, vol. 39, No. 15, Aug. 2011, 8 pages.
Macosko, et al., "Highly Parallel Genome-Wide Expression Profiling of Individual Cells Using Nanoliter Droplets", Cell, vol. 161, No. 5, May 21, 2015, 1202-1214.
Na, et al., "Probing Enzymatic Activity inside Living Cells Using a Nanowire-Cell "Sandwich" Assay", Nano Letters, vol. 13, No. 1, Jan. 9, 2013, 153-158.
Nagano, et al., "Single-cell Hi-C Reveals Cell-to-cell Variability in Chromosome Structure", Nature, vol. 502, Oct. 3, 2013, 59-64.
Niemeyer, et al., "Detecting Antigens by Quantitative Immuno-PCR", Nature Protocols, vol. 2, No. 8, 2007, 1918-1930.
Pardon, et al., "A General Protocol for the Generation of Nanobodies for Structural Biology", Nature Protocols, vol. 9, No. 3, Mar. 2014, 674-693.
Parnas, et al., "A Genome-Wide CRISPR Screen in Primary Immune Cells to Dissect Regulatory Networks", Cell, vol. 162, No. 3, Jul. 30, 2015, 675-686.
Perfetto, et al., "Seventeen-Colour Flow Cytometry: Unravelling the Immune System", Nature Reviews Immunology, vol. 4, No. 8, Aug. 2004, 648-655.
Platt, et al., "CRISPR-Cas9 Knockin Mice for Genome Editing and Cancer Modelling", Cell, vol. 159, No. 2, Oct. 9, 2014, 440-455.
Shalek, et al., "Nanowire-Mediated Delivery Enables Functional Interrogation of Primary Immune Cells: Application to the Analysis of Chronic Lymphocytic Leukemia", Nano Letters, vol. 12, No. 12, Dec. 12, 2012, 6498-6504.
Shalek, et al., "Single-Cell RNA-Seq Reveals Dynamic Paracrine Control of Cellular Variation", Nature, vol. 510, Jun. 19, 2014, 363-369.
Stahlberg, et al., "Quantitative PCR Analysis of DNA, RNAs, and Proteins in the Same Single Cell", Clinical Chemistry, vol. 58, No. 12, Dec. 2012, 1682-1691.
Theile, et al., "Site-Specific N-Terminal Labeling of Proteins Using Sortase-Mediated Reactions", Nature Protocols, vol. 8, No. 9, Sep. 2013, 1800-1807.
Thurman, et al., "The Accessible Chromatin Landscape of the Human Genome", Nature, vol. 489, No. 7414, Sep. 2012, 75-82.
Tomer, et al., "Advanced Clarity for Rapid and High-resolution Imaging of Intact Tissues", Nature Protocols, vol. 9, No. 7, 2014, 1682-1697.
Trombetta, et al., "Preparation of Single-Cell RNA-Seq Libraries for Next Generation Sequencing", Current Protocols in Molecular Biology, vol. 107, Jul. 2014, 25 pages.
"International Preliminary Report on Patentability_for_PCT_Application_No_PCT_US2016_059195_BROD_0850WP", dated May 11, 2018, 1-10.
"2017 Top 10 Innovations", 2017 Top 10 Innovations, The Scientist, pp. 1-11, Dec. 1, 2017.
"Acrylamide Product Information Sheet", Sigma Aldrich 1996 Product Information Sheet, A8887, pp. 1-2, 1996.
"American Cell Biology Meeting Program 2017", The 2017 ASCB EMBO Meeting, pp. 1-198, Dec. 2017.
"An Introduction to Linked-Read Technology for a More Comprehensive Genome and Exome Analysis", 10X Genomics Technical Note, pp. 1-5, 2016.
Bio-Rad and Illumina to Co-Develop Comprehensive Solution for Single-Cell Genomics, "Scalable, High-Throughput Platform to Offer Unprecedented Insight into Gene Expression of Individual Cells," Bio-Rad Newsroom, pp. 1-2, Jan. 11, 2016.
"Bio-Rad ddSEQ Single-Cell Isolator Instruction Manual", Bio-Rad, Catalog #12004336, pp. 1-24, 2017.
"Bio-Rad Laboratories, Inc. Form 10-K for the year ended Dec. 31, 2016", pp. 1-92.
"Bio-Rad Life Science Research Product Catalog", Bio-Rad Life Science Research 2017 Product Catalog, pp. 1-500, 2017.
"Boston Medical Center/ Boston University School of Medicine Department of Medicine Newsletter", pp. 1-20, 2017.
"Cancer Moonshot", National Cancer Institute, pp. 1-4, Jan. 8, 2019.
"ChromiumTM Genome Reagent Kits v2 User Guide," Multiplex Kit, 96 rxns, PN-120262, 10X Genomics, pp. 1-71, 2016.
"ChromiumTM Single Cell 3' Reagent Kits Quick Reference Cards", ChromiumTM Single Cell 3' Chip Kit PN-120232, 10X Genomics, pp. 1-10, 2016.
"ChromiumTM Chromium Single Cell 3' Reagent Kits Safety Data Sheets", ChromiumTM Single Cell 3' Gel Bead Kit PN-120231, 10X Genomics, pp. 1-10, Jul. 11, 2016.
"ChromiumTM Chromium Single Cell 3' Reagent Kits v2 Safety Data Sheets," Chromium Single Cell 3' Gel Bead Kit v2, 16 runs, PN-120235, 10X Genomics, pp. 1-10, Oct. 7, 2016.
"Chromium Single Cell 3' Reagent Kits v3 with Feature Barcoding technology for CRISPR Screening", Chromium Single Cell 3' GEM, Library & Gel Bead Kit v3, 4 rxns PN-1000092, 10X Genomics, pp. 1-70, CG0001841 | Rev A, 2018.
"ChromiumTM Single Cell 3' Reagent Kits v2 Quick Reference Cards," ChromiumTM Single Cell 3' Library & Gel Bead Kit, 4 rxns PN-120267, 10X Genomics, CG000075 | Rev C, pp. 1-10, 2017.
"ChromiumTM Single Cell 3' Reagent Kits Safety Data Sheets," ChromiumTM Single Cell 3' Library Kit, 10X Genomics, PN-120230, pp. 1-139, May 25, 2016.
"ChromiumTM Single Cell 3' Reagent Kits v2 Safety Data Sheets," ChromiumTM Single Cell 3' Library Kit v2 16 rxns, PN-120234, 10X Genomics, pp. 1-121, Oct. 7, 2016.
"Chromium Single Cell 3' Reagent Kits v2 User Guide," Chromium Single Cell 3' Library & Gel Bead Kit v2, 16 rxns PN-120237, 10X Genomics, pp. 1-74, 2018.
"ChromiumTM Single Cell V(D)J Reagent Kits User Guide," ChromiumTM Single Cell 5' Library & Gel Bead Kit, 16 rxns PN-1000006, 10X Genomics, pp. 1-73, 2017.
"Chromium Single Cell 3' Reagent Kits v2 User Guide", Chromium Single Cell A Chip Kit, 16 rxns PN-1000009, 10X Genomics, pp. 1-74, CG00052 | Rev E, 2018.
"Chromium Single Cell 3' Reagent Kits v2 Safety Data Sheets," Chromium Single Cell A Chip Kit, 48 runs, 10X Genomics, PN-120236, Oct. 6, 2016.

(56) References Cited

OTHER PUBLICATIONS

"Chromium Single Cell ATAC Reagent Kits," Chromium Single Cell ATAC Library & Gel Bead Kit, 16 rxns PN-1000110, 10X Genomics, CG000168 | Rev A, pp. 1-47, 2018.
"Chromium Single Cell DNA Reagent Kits", Chromium Single Cell DNA Library & Gel Bead Kit, 16 rxns PN-1000040, 10X Genomics, CG000153 | Rev B, pp. 1-65, 2018.
"ChromiumTM Controller Training Kit User Guide", 10X Genomics, CG00021 | Rev B, pp. 1-27, (Product ID 120244), 2016.
"ChromiumTM Training Kits Safety Data Sheets", ChromiumTM Training Reagents and Gel Bead Kit, 10X Genomics, PN-120238, Rev A, pp. 1-33, May 24, 2016.
"ddSEQ™ Cartridge Holder", Bio-Rad ddSEQ™ Cartridge Holder #12004739, 2016.
"ddSEQ™ Single-Cell Isolator—Accessories", ddSEQ™ Single-Cell Isolator—Accessories—Bio-Rad, pp. 1-2, 2016.
"ddSEQ™ Single-Cell Isolator—Ordering", ddSEQ™ Single-Cell Isolator Bio-Rad, 2016.
"ddSEQ™ Single-Cell Isolator by Bio-Rad", Bio-Rad, pp. 1-8, Select Science, 2019.
"ddSEQ™ Single-Cell Isolator by Bio-Rad", ddSEQ™ Single-Cell Isolator, Bio-Rad, pp. 1-2, 2016.
"ddSEQ™ Test Cartridges", Bio-Rad ddSEQ™ Test Cartridges #12003862, 2016.
"Deoxyribonuclease I from bovine pancreas", Sigma-Aldrich Deoxyribonuclease I from bovine pancreas, CAS Number: 9003-98-9, 2018.
"DNase I (RNase-free)", New England Biolabs, Inc. (NEB), pp. 1-6, 2018.
"DTT 1,4-Dithiothreitol", Sigma-Aldrich, CAS No. 3483-12-3, pp. 1-4, 2015.
Office Action issued by the European Patent Office in Application No. 15767655.2 dated Apr. 17, 2018, 4 pages.
Office Action issued by the European Patent Office in Application No. 15767655.2 dated Jul. 11, 2018, 12 pages.
Banga, J.P., "SDS-Polyacrylamide Gel Electrophoresis (SDS-PAGE)", Encyclopedia of Immunology ISBN:0-12-226765-6, pp. 2143-2144, 1998.
"Generation of Human Tumor Atlases-Cancer Moonshot Recommendation", National Cancer Institute, pp. 1-4, Jan. 8, 2019.
"Genome Analysis Core", pp. 1-2, Georgia Institute of Technology, 2019.
"Georgia Tech—Shared User Management System", pp. 1-12, Georgia Institute of Technology, 2015.
"Hydrophobic Interaction Chromatography", Amersham Pharmacia Biotech 2000, Edition AB, pp. 1-104, ISBN 91-970490-4-2, 2000.
"Illumina and Bio-Rad Launch Solution for Single-Cell Genomic Sequencing to Enable Robust Study of Complex Diseases", Bio-Rad, pp. 1-2, Jan. 9, 2017.
"Illumina and Bio-Rad Launch Solution for Single-Cell Genomic Sequencing to Enable Robust Study of Complex Diseases", 69th AACC Annual Scientific Meeting Press Program, Article ID: 678428, pp. 1-6, Jul. 25, 2017.
"Illumina Bio-Rad SureCell WTA 3' Library Prep Reference Guide", Illumina, Document # 1000000021452 v01, pp. 1-53, Jun. 2017.
"Illumina SureCell WTA 3' Checklist", Illumina, Document # 1000000021454 v00, pp. 1-6, Feb. 2017.
"Illumina® | Bio-Rad® Single Cell Sequencing", illumina I Bio-Rad, pp. 1-37, 2015.
"Illumina® Bio-Rad® SureCellTM WTA 3' Library Prep Kit for the ddSEQTM System", illumina I Bio-Rad, pp. 1-4, 2015.
"Infoporte—Cores", Infoporte | Version: 7.1.1 | © 2019 The University of North Carolina at Chapel Hill.
"The Instrument—Chromium Controller Compatible Solutions", 10X Genomics, pp. 1-7, 2019.
Rothberg, et al., "An integrated semiconductor device enabling non-optical genome sequencing", Nature, vol. 475, pp. 348-352, Jul. 21, 2011.

Shimkus, et al., "A chemically cleavable biotinylated nucleotide: usefulness in the recovery of protein-DNA complexes from avidin affinity columns.", Proc Natl Acad Sci U S A., vol. 82, No. 9, pp. 2593-2597, May 1985.
Song, et al., "A Microfluidic System for Controlling Reaction Networks in Time", Angew. Chem. Int. Ed. 2003, vol. 42, No. 7, pp. 767-772, ,Received: Sep. 6, 2002.
Soumillon, et al., "Characterization of Directed Differentiation by High-Throughput Single-Cell RNA-Seq", BioRxiv, pp. 1-13, Preprint: Mar. 5, 2014.
Spies, et al., "Genome-wide reconstruction of complex structural variants using read clouds", Nat Methods, vol. 14, No. 9, pp. 915-920, Sep. 2017.
Stoeckius, et al., "Large-scale simultaneous measurement of epitopes and transcriptomes in single cells", Nature Methods, vol. 14, No. 9, pp. 865-868, Sep. 2017.
Taylor, et al., "A scalable high-throughput method for RNA-Seq analysis of thousands of single cells", illumina I Bio-Rad, 2016.
Tewhey, et al., "Microdroplet-based PCR enrichment for large-scale targeted sequencing", Nature Biotechnology, vol. 27, No. 11, pp. 1025-1031, Nov. 1, 2009.
The Broad Institute, Inc., "Communication Pursuant to Rule 164(2)(b) and Article 94(3) EPC", Jul. 11, 2018, 12 pages.
Tice, et al., "Formation of Droplets and Mixing in Multiphase Microfluidics at Low Values of the Reynolds and the Capillary Numbers", Langmuir, vol. 19, No. 22, pp. 9127-9132, Published on Web: Aug. 12, 2003.
Wilson, "Ape1 abasic endonuclease activity is regulated by magnesium and potassium concentrations and is robust on alternative DNA structures.", J Mol Biol., vol. 345, No. 5, pp. 1003-1014, Feb. 4, 2005.
Wu, et al., "Termination of DNA synthesis by N6-alkylated, not 3'-O-alkylated, photocleavable 2'-deoxyadenosine triphosphates", Nucleic Acids Res., vol. 35, No. 19, pp. 6339-6349, Sep. 18, 2007.
Yan, et al., "Intestinal enteroendocrine lineage cells possess homeostatic and injury-inducible stem cell activity", Cell Stem Cell, vol. 21, No. 1, pp. 78-90, Jul. 6, 2017.
Yan, et al., "Non-equivalence of Wnt and R-spondin ligands during Lgr5+ intestinal stem cell self-renewal", Nature, vol. 545, No. 7653, pp. 238-242, May 11, 2017.
Zhang, et al., "Massively Parallel Single-Molecule and Single-Cell Emulsion Reverse Transcription Polymerase Chain Reaction Using Agarose Droplet Microfluidics", Anal. Chem., vol. 84, No. 8, pp. 3599-3606, Published: Mar. 27, 2012.
Zheng, et al., "Massively parallel digital transcriptional profiling of single cells", Nature Communications, vol. 8, Article number: 14049, pp. 1-12, Published: Jan. 16, 2017.
Metzker, "Sequencing technologies—the next generation", Nature Reviews, Genetics, vol. 11, pp. 31-46, Published online: Dec. 8, 2009.
Chung, et al., "Statistical Significance of Variables Driving Systematic Variation in High-Dimensional Data", Bioinformatics, vol. 31, No. 4, pp. 545-554, Advance Access publication: Oct. 21, 2014.
Collins, "Biomedical Research Highlighted in Science's 2018 Breakthroughs", NIH Director's Blog, pp. 1-9, Jan. 8, 2019.
Corbo, et al., "A Typology of Photoreceptor Gene Expression Patterns in the Mouse", PNAS, vol. 104, Issue 29, pp. 12069-12074, Jul. 17, 2007.
Cuatrecasas, Pedro, "Protein Purification by Affinity Chromatography", J Biol Chem, vol. 245, Issue 12, pp. 3059-3065, Jun. 25, 1970.
Damha, et al., "An improved procedure for derivatization of controlled-pore glass beads for solid-phase oligonucleotide synthesis", Nucleic Acids Res., vol. 18, No. 13, pp. 3813-3821, Accepted: May 17, 1990.
Descamps, et al., "Gelatinase B/matrix Metalloproteinase-9 Pprovokes Cataract by Cleaving Lens BetaB 1 Crystallin", The FASEB Journal, vol. 19, Issue 1, pp. 29-35, Jan. 2005.
Ding, et al., "Progress Towards a Systematic Comparison of Single Cell RNA-Seq Methods", Broad Institute, Feb. 12, 2019.
Dixit, et al., "Perturb-Seq: Dissecting Molecular Circuits with Scalable Single-Cell Rna Profiling of Pooled Genetic Screens", Cell, vol. 167, Issue 7, pp. 1853-1866, Dec. 15, 2016.

(56) References Cited

OTHER PUBLICATIONS

Dobin, et al., "STAR: Ultrafast Universal RNA-seq Aligner", Bioinformatics, vol. 29, Issue 1, pp. 15-21, Advance Access publication: Oct. 25, 2012.
Dressman, et al., "Transforming single DNA molecules into fluorescent magnetic particles for detection and enumeration of genetic variations", PNAS, vol. 100, No. 15, pp. 8817-8822, Jul. 22, 2003.
Droege, et al., "The Genome Sequencer FLX System—longer reads, more applications, straight forward bioinformatics and more complete data sets.", J Biotechnol., vol. 136, Issues 1-2, pp. 3-10, Accepted: Mar. 31, 2008.
Edd, et al., "Controlled Encapsulation of Single Cells into Monodisperse Picoliter Drops", Lab Chip, vol. 8, Issue 8, pp. 1262-1264, Aug. 2008.
Ester, et al., "A Density-Based Algorithm for Discovering Clusters in Large Spatial Databases with Noise", pp. 226-231, KDD-96, 1996.
Farmer, et al., "Defining epithelial cell dynamics and lineage relationships in the developing lacrimal gland", Development, The Company of Biologists, vol. 144, Issue 13, pp. 2517-2528, Accepted: May 31, 2017.
Feigenspan, et al., "Expression of Neuronal Connexin36 in All Amacrine Cells of the Mammalian Retina", The Journal of Neuroscience, vol. 21, Issue 1, pp. 230-239, Jan. 1, 2001.
Gao, et al., "Secondary structure effects on DNA hybridization kinetics: a solution versus surface comparison", Nucleic Acids Research, 2006, vol. 34, No. 11, pp. 3370-3377, Accepted: May 27, 2006.
Glatthar, et al., "A New Photocleavable Linker in Solid-Phase Chemistry for Ether Cleavage", Org. Lett. 2000, vol. 2, No. 15, pp. 2315-2317, Received: May 18, 2000.
Greenfieldboyce, "Biological cartographers seek to map the trillions of cells in the human body", NPR, pp. 1-5, Jan. 5, 2019.
Greer, et al., "Linked read sequencing resolves complex genomic rearrangements in gastric cancer metastases", Genome Medicine, vol. 9, No. 57, pates 1-17, 2017.
Gueroult, et al., "How Cations Can Assist DNase I in DNA Binding and Hydrolysis", PLoS Comput Biol., vol. 6, Issue 11:e1001000, pp. 1-11, Nov. 18, 2010.
Haber, et al., "A single-cell survey of the small intestinal epithelium", Nature, vol. 551, No. 7680, pp. 333-339, Nov. 16, 2017.
Hamady, et al., "Error-correcting barcoded primers for pyrosequencing hundreds of samples in multiplex", Nature Methods, vol. 5, No. 3, pp. 235-237, Mar. 2008.
Hamady, et al., "Microbial community profiling for human microbiome projects: Tools, techniques, and challenges", Genome Res., vol. 19, No. 7, pp. 1141-1152, ISSN 1088-9051/09, Jul. 2009.
He, et al., "High-resolution crystal structures reveal plasticity in the metal binding site of apurinic/apyrimidinic endonuclease I.", Biochemistry, vol. 53, No. 41, pp. 6520-6529, Published: Sep. 24, 2014.
Hoffmann, et al., "DNA bar coding and pyrosequencing to identify rare HIV drug resistance mutations", Nucleic Acids Res., vol. 35, No. 13, e91, pp. 1-8, Published online: Jun. 18, 2007.
Holmberg, et al., "The biotin-streptavidin interaction can be reversibly broken using water at elevated temperatures.", Electrophoresis, vol. 26, No. 3, pp. 501-510, Feb. 2005.
Islam, et al., "Quantitative single-cell RNA-seq with unique molecular identifiers", Nature Methods, , vol. 11, No. 2, pp. 163-166, Feb. 2014.
Kaiser, et al., "Huge trove of British biodata is unlocking secrets of depression, sexual orientation, and more", Science | AAAS, pp. 1-12, Jan. 3, 2019.
Kovall, et al., "Structural, functional, and evolutionary relationships between exonuclease and the type II restriction endonucleases", Proc Natl Acad Sci U S A., vol. 95, No. 14, pp. 7893-7897, Jul. 1998.

Kumaresan, et al., "High-Throughput Single Copy DNA Amplification and Cell Analysis in Engineered Nanoliter Droplets", Anal. Chem., vol. 80, No. 10, pp. 3522-3529, May 15, 2008.
Kutnjak, et al., "Calorimetric study of octylcyanobiphenyl liquid crystal confined to a controlled-pore glass.", Physical Review E, The American Physical Society, pp. 021705-1-021705-12, Published: Aug. 22, 2003.
Litosh, et al., "Improved nucleotide selectivity and termination of 3'-OH unblocked reversible terminators by molecular tuning of 2-nitrobenzyl alkylated HOMedU triphosphates.", Nucleic Acids Res., vol. 39, No. 6, pp. 1-13, Published online: Jan. 11, 2011.
Macosko, et al., "Highly Parallel Genome-Wide Expression Profiling of Individual Cells Using Nanoliter Droplets", Cell, Voume 161, No. 5, pp. 1202-1214, May 21, 2015.
Malone, et al., "Bringing Renal Biopsy Interpretation Into the Molecular Age With Single-Cell RNA Sequencing", Seminars in Nephrology, vol. 38, Issue 1, pp. 1-17, Author Manuscript; available in PMC: Jan. 1, 2019.
Margulies, et al., "Genome Sequencing in Open Microfabricated High Density Picoliter Reactors", Nature, vol. 437, No. 7057, pp. 376-380, Sep. 15, 2005.
McKenna, et al., "The Macaque Gut Microbiome in Health, Lentiviral Infection, and Chronic Enterocolitis", PLoS Pathog., vol. 4, Issue 2, e20, pp. 0001-0012, Feb. 8, 2008.
Metzker, "Emerging technologies in DNA sequencing.", Genome Res., vol. 15, No. 12, pp. 1767-1776, Dec. 2005.
Miller, et al., "Basic Concepts of Microarrays and Potential Applications in Clinical Microbiology", Clinical Microbiology Reviews, vol. 22, No. 4, pp. 611-633, Oct. 2009.
Mol, et al., "DNA-bound structures and mutants reveal abasic DNA binding by APE1 and DNA repair coordination.", Nature, vol. 403, No. 6768, pp. 451-456, Jan. 27, 2000.
Narasimhan, et al., "Health and population effects of rare gene knockouts in adult humans with related parents", Science, vol. 352, No. 6284, pp. 474-477, Apr. 22, 2016.
Nguyen, "Optical detection for droplet size control in microfluidic droplet-based analysis systems", Nguyen et al., Optical detection for droplet size control in microfluidic droplet-based analysis systems, 117 Sensors and Actuators B 117, pp. 431-436, Available online: Jan. 18, 2006.
Novak, et al., "Single cell multiplex gene detection and sequencing with microfluidically generated agarose emulsions", Angew. Chem. Int. Ed., pp. 1-11, 2010.
Novak, et al., "Single Cell Multiplex Gene Detection and Sequencing with Microfluidically Generated Agarose Emulsions", Agnew. Chem. Int. Ed., pp. 390-395, Jan. 10, 2011.
Pal, et al., "Construction of developmental lineage relationships in the mouse mammary gland by single-cell RNA profiling", Nature Communications, vol. 8, Article number: 1627, pp. 1-14, Nov. 20, 2017.
Parameswaran, et al., "A pyrosequencing-tailored nucleotide barcode design unveils opportunities for large-scale sample multiplexing", Nucleic Acids Res., vol. 35, No. 19, e130, pp. 1-9, Published online: Oct. 11, 2007.
Pennisi, "Development Cell by Cell", Science, vol. 362, Issue 6421, pp. 1344-1345, Dec. 21, 2018.
Perona, "Type II restriction endonucleases.", Methods, vol. 28, No. 3, pp. 353-364, Accepted: Jul. 30, 2002.
Peterson, et al., "The effect of surface probe density on DNA hybridization", Nucleic Acids Res., vol. 29, No. 24, pp. 5163-5168, Dec. 15, 2001.
Qi, et al., "Digital analysis of the expression levels of multiple colorectal cancer-related genes by multiplexed digital-PCR coupled with hydrogel bead-array.", Analyst, vol. 136, No. 11, pp. 2252-2259, Accepted: Mar. 11, 2011.
Final Office Action for U.S. Appl. No. 15/453,405, issued by the U.S. Patent Office dated Mar. 27, 2019, 17 pages.

* cited by examiner

1. Synthesize ssDNA with the following structure:

▬▬▬ contains RE site to create 4b sticky end
═══ Index A
▬▬▬ UMI
⋯⋯ Ligation handle 2. hybridize primer providing sticky end at 3' end

▬▬▬ Primer including sticky end overhang

3. DNA polymerase for second strand synthesis

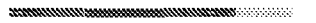

4. Restriction enzyme digestion to generate 5' sticky end

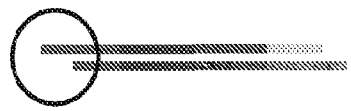

▬▬▬ contains RE site to create 4b sticky end
═══ Index A
▬▬▬ UMI
⋯⋯ Ligation handle
▬▬▬ Primer including sticky end overhang

FIG. 10

1. tagmentation of genomic DNA (Tn5)
2. polymerize hydrogel drop, incorporates genomic DNA into mesh.
3. anneal ligation primer, generating sticky end
4. extend
As previously continue to:
5. split-pool USI +UMI addition
6. Amplification (T7/PCR) + Sequencing
FIG. 14

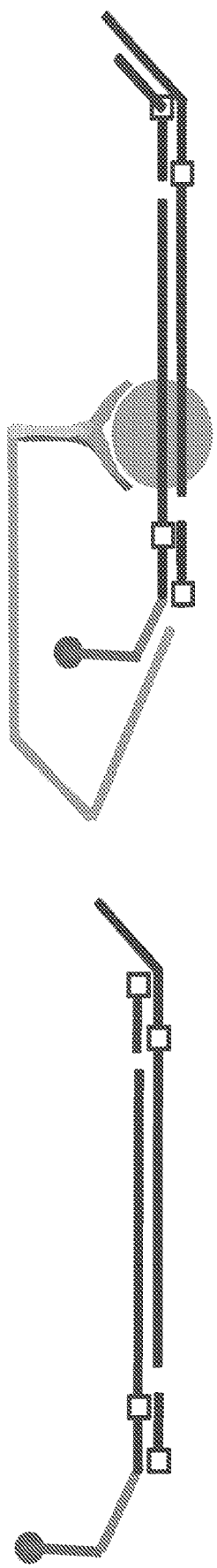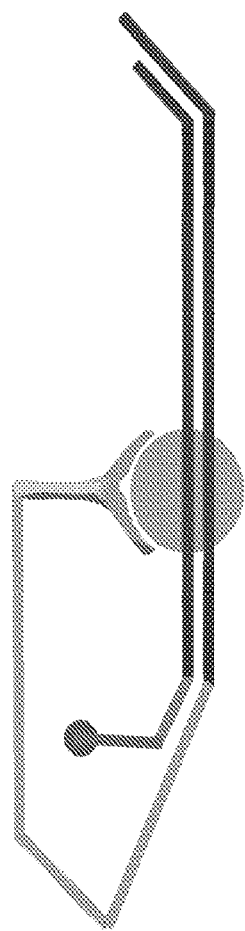
FIG. 15

1. Synthesize ssDNA with the following structure:

▬▬▬ contains RE site to create 4b sticky end
　　　　　▬▬▬ Index C
　　　　　▬▬▬ UMI
　　　　　▬▬▬ PCR primer site 2. Hybridize universal primer

▬▬▬ contains RE site to create 4b sticky end
　　　　　▬▬▬ index C
　　　　　▬▬▬ UMI
　　　　　▬▬▬ PCR primer site
　　　　　▬▬▬ Primer for second strand synthesis 3. DNA polymerase for second strand synthesis

4. Restriction enzyme digest

▬▬▬ contains RE site to create 4b sticky end
　　　　　▬▬▬ Index C
　　　　　▬▬▬ UMI
　　　　　▬▬▬ PCR primer site
　　　　　▬▬▬ Primer

FIG. 18

1) Synthesize ssDNA containing:
≡ RE site to create 4b sticky end
≡ Unique Location index (ULI) randomly generated
≡ Universal hybridization site
≡ Spacer
2) Circularize using CircLigase
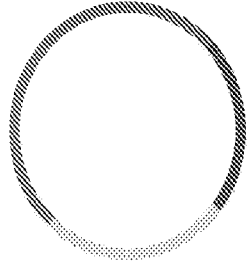
3) Perform Rolling circle amplification
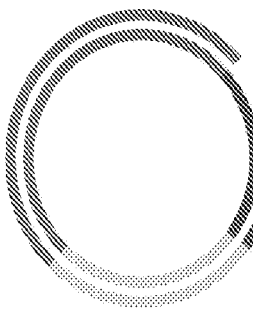
4) isolate linear amplicon and use as staining probe
FIG. 20

1) stain with ULI-probe
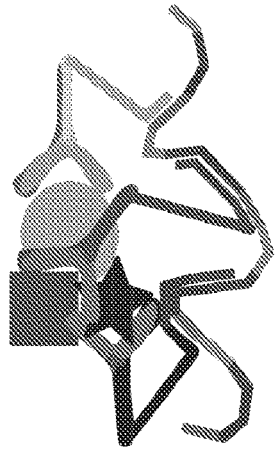
2) extend
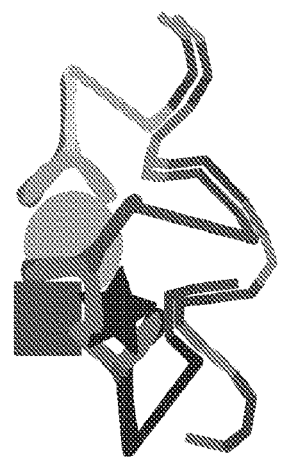
3) Restriction enzyme digest generates 4bp overhang for sticky end ligation of USI +UMI
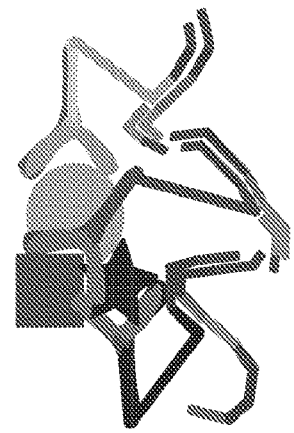
4) ligate on index A, B and C+UMI +PCR
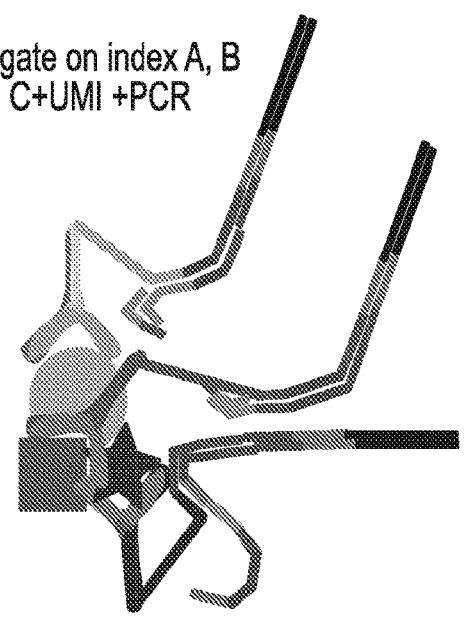
5) Release oligo's from ligand and PCR or T7 amplify, each sequence to amplify (top strand) has:
PCR FWD + UCI + universal hybridization site + ULI + USI + UMI + PCR Rev
FIG. 21

MULTIPLEX ANALYSIS OF SINGLE CELL CONSTITUENTS

CROSS-REFERENCE TO RELATED APPLICATIONS

This application is the U.S. National Stage of International Application No. PCT/US2016/059195, filed Oct. 27, 2016 published in English under PCT Article 21(2), which claims the benefit of U.S. Provisional Application No. 62/247,656, filed Oct. 28, 2015. The entire content of the above-identified priority application is hereby fully incorporated herein by reference.

STATEMENT REGARDING FEDERALLY SPONSORED RESEARCH

This invention was made with government support under Grant No. HG006193 awarded by the National Institutes of Health. The government has certain rights in the invention.

TECHNICAL FIELD

The subject matter disclosed herein is generally directed to methods for high multiplex protein or cellular constituent analysis in single cells or single aggregations of cellular constituents.

BACKGROUND

Regulatory circuits in cells process signals, make appropriate decisions, and orchestrate physiological responses under diverse signals. Diseases, in turn, arise from circuit malfunctions: one or more components are missing or defective; a key module is over- or under-active. A comprehensive picture of all the cellular components, the circuits in which they function, and how these integrate to form responses is needed to understand disease and develop more effective treatments. Genomic research on dissecting cellular circuitry has had three phases:

Phase I: Genomic observations. Early advances in functional genomics made it possible to observe molecular profiles in different cells. Such global analysis has been very powerful in drawing hypotheses that relate regulators to their targets from statistical correlations. However, it is also very limited: the hypotheses were mostly not tested, and because correlation is not causation, many are wrong.

Phase II: Perturbation of single components. To determine causation, genomic profiles were used to infer a molecular model, and then hundreds of genes were perturbed one at a time to observe their effect on the genomic profile. Applicants pioneered key experimental and computational tools (1-49); applied them to model two circuits in immune cells and ES cells; discovered hundreds of new functional factors; and built rigorous molecular models that relate these factors to molecular mechanisms and physiological effect (1-49). However, testing genes individually is too limited: because the genes in biological circuits have non-linear interactions, it cannot be predicted how a circuit functions simply by summing up the individual effects.

Phase III: Combinatorial probing of circuits. What is necessary is a combinatorial approach: perturbing multiple components simultaneously, at a large enough scale that will allow reliable reconstruction of circuits.

Such a combinatorial approach has been considered intractable in genomics, because it required: (1) the ability to perturb many genes simultaneously in the same cell; (2) the ability to readout genomic profiles in individual cells, so that the effect of many perturbations can be assessed in parallel in a pool of cells; and (3) the development of mathematics that enables inference of higher-order interactions from a random sampling of this space of possibilities (because even millions of experiments are very few compared to the staggering size of the possible combinatorial space).

However, three very recent advances now put this approach within reach: (1) large scale multi-gene perturbation with CRISPR; (2) massively-parallel single cell genomic profiling; and (3) new mathematical analysis that posits that under biologically realistic assumptions, most of the meaningful interactions based on random sampling of the space can be recovered.

Single cell analysis of genomic variation and transcriptome heterogeneity allows for identification of factors influencing disease susceptibility, unraveling of intracellular regulatory networks and discovery of novel cell types. Despite their status as main mediators of biological functions, proteins are currently only read out a handful at a time, either due to spectral overlap of fluorescent tags in flow cytometry (Perfetto et al., 2004) or limit in the number of available isotope tags in mass cytometry (Bendall et al., 2011). Specifically, the current assays (e.g., CyTOF), allow multiplexed, single cell detection of dozens of proteins in millions of cells, but rely on antibodies and cannot yet be combined with DNA readout. Conversely, mass spectrometry (LC-MS/MS) allows quantitative analysis of entire proteomes, but deep analysis requires large amounts of protein/cells. Thus, there is a need for high multiplex analysis of proteins in single cells.

Citation or identification of any document in this application is not an admission that such document is available as prior art to the present invention.

SUMMARY

It is an object of the present invention to provide a method for the high multiplex analysis of cellular constituents by linking nucleic acids tags to existing ligand binding and/or antibody technologies to enable proteomic or cellular constituent detection and relative quantification by next-generation sequencing (NGS) in single cells or isolated aggregations of cellular constituents.

It is a further object of the present invention to provide for comparing high multiplex protein data variation between single cells or isolated aggregation of cellular constituents and between different biological conditions (e.g. healthy vs. diseased states; one genetic perturbation vs. another, different genetic backgrounds).

It is a further object of the present invention to provide massively parallel profiling of all circuit aspects in single cells or isolated aggregations of cellular constituents: from RNA to chromatin organization to protein levels.

In a first aspect, the present invention provides a method of assaying segregated cellular constituents, comprising: admixing at least one isolated aggregation of cellular constituents with monomers of a polymerizable gel; polymerizing the gel, to embed the cellular constituents in discrete polymer matrices; incubating the cellular constituents embedded in the polymer matrices with one or more labeling ligands with specific binding affinity for one or more target cellular constituents to produce one or more labeled cellular constituents in the polymer matrices, wherein each of the one or more labeling ligand comprises a bound oligonucleotide label comprising a unique constituent identifier (UCI) sequence, and wherein the incubation comprises binding conditions under which the labeling ligand will bind to the cellular constituent within the polymer matrix, and the incubation further comprises washing conditions under which unbound labeling ligands will be washed out of the polymer matrix; and sequencing the oligonucleotide label, whereby detecting the UCI by sequencing indicates the presence of the target cellular constituent.

Cellular constituents may include any molecule within a cell; i.e. proteins, nucleic acids, or post translational modifications (PTM). The cellular constituent may be a protein, RNA transcript, metabolite, or a DNA molecule. Specific cellular constituents may be proteins, modified proteins, hormones, cytokines, cellular metabolites, or carbohydrates. The isolated aggregation of cellular constituents may be a cell, an extracellular vesicle, an organelle, or an organized subcomponent thereof, including molecular complexes. Isolated aggregations of cellular constituents may include separate organelles of a single cell or separate organelles isolated from a population of cells. Organelles may be for example, mitochondria, nuclei, or cellular vesicles. In one embodiment, a specific type of single cells may be isolated. In one embodiment, immune cells are isolated from a population of cells. Not being bound by a theory, single mitochondria can be purified from a population of cells and the relative amounts of constituents present in each individual mitochondrion may be analyzed. Not being bound by a theory, immune cells may be isolated by a method such as cell sorting and the relative representation of cellular constituents may be determined for each individual cell.

The step of admixing the isolated aggregation of cellular constituents with monomers may be carried out in an aqueous solution, or in an aqueous aliquot or droplet present in an oil emulsion. The polymer matrix may be a hydrogel. The polymer matrix may be any hydrogel capable of polymerization to create a solid matrix that fixes the cellular constituents and provides a porosity capable of allowing labeling ligands to freely diffuse through the network of pores. The cellular constituents may be further fixed by treating with an aldehyde. The aldehyde may be formaldehyde, paraformaldehyde, or glutaraldehyde. Not being bound by a theory the fixation in a solid matrix prevents the mixing of the cellular constituents between the isolated aggregations of cellular constituents. Not being bound by a theory, capturing cellular constituents in a solid polymer mesh insures that they are physical units that can be ligand and/or antibody stained as a pool and isolated as single cells or isolated aggregates of cellular constituents subsequently. Not being bound by a theory, the fixing of cellular constituents in the polymer matrix allows access to the labeling ligands to intracellular constituents.

The physical units formed by the polymer matrix may be particles, droplets, or a continuous polymer matrix with discrete regions comprising the isolated aggregates of cellular constituents. Therefore, the polymer matrix may include more than one isolated aggregate of cellular constituents. The polymer matrix may be divided such that isolated aggregates of cellular constituents are separable. The polymer matrix may be separable in that individual particles, droplets, or sections can be isolated. They may be isolated by physical manipulation using a sorting device. The sorting device may use microfluidics. They may be separated by use of dilution or manual manipulation by a user. They may be separated by use any kind of (micro) dissection. The cellular constituents within the polymer matrix may be stained with a dye, or a dye-conjugated ligand indicating the location of individual cellular constituents or cells. The polymer matrix may be punched to isolate a core, wherein each core from the polymer matrix contains a single isolated aggregate of cellular constituents. Not being bound by a theory, the fixation of isolated aggregates of cellular constituents in a matrix allows each isolated aggregate of cellular constituents to be compartmentalized wherein the separate compartments can be treated in a single experimental vessel or container and separated subsequently.

The labeling ligands are linked with an oligonucleotide label that can be used to determine the identity of the ligand. Each oligonucleotide label may comprise a unique constituent identifier (UCI) that can be used to determine the presence of a cellular constituent. Not being bound by a theory, the availability of unique sequences allows the labeling and detection of a plurality of ligands each for a specific constituent. Not being bound by a theory, the UCI allows a DNA readout for detection of a cellular constituent. The DNA readout may be by any sequencing method or method of amplification, such as by PCR or next generation sequencing. The oligonucleotide label may additionally include a promoter for amplification by an RNA polymerase, such as T7 polymerase. Not being bound by a theory, amplification by T7 polymerase allows amplification of low represented sequences, whereas such sequences may be diluted out by domination of a higher represented sequence during PCR. Not being bound by a theory, the labeling of each labeling ligand with a unique UCI allows the identification of more than ten, or hundred, or thousands of cellular constituents in an isolated aggregation of cellular constituents.

The method may further comprise segregating the discrete polymer matrices comprising the labeled constituents before the step of sequencing. Segregating the discrete polymer matrices may be by sorting single discrete matrices into separate reaction vessels. Segregating the discrete polymer matrices may be by forming discrete unique-identifier-transfer compositions, each comprising the cellular constituents embedded in a discrete polymer matrix and a transfer particle, wherein: the ligand oligonucleotide label further comprises a capture sequence, and the UCI and capture sequence are together releasably attached to the labeling ligand; the labelling ligand is bound to the target cellular constituent; and, the transfer particle comprises: a capture-binding-sequence having specific binding affinity for the capture sequence attached to the UCI, and, a unique source identifier (USI) sequence that is unique to each transfer particle. The USI of each transfer particle preferably comprises 4-15 nucleotides. The method may further comprise releasing the UCI from the labeled ligand, under conditions within the unique-identifier-transfer composition so that the released capture sequence binds to the capture-binding-sequence on the transfer particle, thereby transferring the UCI to the transfer particle. The transfer particle may be a solid bead. The transfer particle may be a hydrogel bead. The transfer particle may also be used to capture nucleic acids present in a discrete polymer matrix. The nucleic acids may be RNA and/or DNA. Not being bound by a theory the transfer particle may be used to capture both the UCI and the nucleic acids, whereby the source of the bound cellular constituents and nucleic acids can be determined after sequencing.

The method may further comprise, before the sequencing step, generating a USI for each discrete polymer matrix by a split pool ligation method, wherein the oligonucleotide label further comprises a universal ligation handle (ULH) sequence configured to produce a DNA overhang capable of hybridization to a complementary overhang on a first index nucleotide sequence, wherein the first index nucleotide sequence comprises an overhang complementary to a final index sequence or optionally a middle index sequence, wherein the middle index sequence comprises overhangs complementary to the first index sequence and to the final index sequence or optionally to another middle index sequence and final index sequence, wherein the final index sequence has a single overhang complementary to the preceding index sequence, and wherein the first, middle, and final index sequences are selected from a plurality of unique sequences comprising compatible DNA overhangs and 10 to 30 base pairs of unique sequence.

The split pool ligation method may comprise: splitting the pool of discrete polymer matrices into separate pools of polymer matrices, each containing a unique first index sequence; ligating the first index sequence to the ligation handle; pooling the discrete polymer matrices; optionally, splitting the pool of discrete polymer matrices into separate pools each containing a unique middle index sequence; ligating the middle index sequence to the first index sequence; and pooling the discrete polymer matrices; optionally, repeating the steps with another middle index sequence; splitting the pool of discrete polymer matrices into pools containing a unique final index sequence; and ligating the final index sequence to the preceding index sequence, whereby each discrete polymer matrix comprises a USI. The USI may have no middle index sequence, one middle index sequence, two middle index sequences, preferably the USI has a first, middle, and final index sequence. Not being bound by a theory, the size of the unique sequences in each index determines the amount included. Not being bound by a theory, the number of indices selected is the amount necessary such that the probability of having identical USI sequences on spate polymer matrices is approaching zero. In an exemplary embodiment, each index includes 192 unique sequences.

The ligation handle may comprise a restriction site for producing an overhang complementary with a first index sequence overhang, and wherein the method further comprises digestion with a restriction enzyme. The ligation handle may comprise a nucleotide sequence complementary with a ligation primer sequence and wherein the overhang complementary with a first index sequence overhang is produced by hybridization of the ligation primer to the ligation handle. Additionally, the ULH may comprise a dsDNA part that already includes the overhang needed for index ligation.

The UCI may comprise 4 to 30 nucleotides or 7 to 30 nucleotides, preferably about 21 nucleotides. The oligonucleotide label may further comprise a unique molecular identifier (UMI) sequence. The first, middle, or final index sequence may further comprises a unique molecular identifier (UMI) sequence. The UMI may comprise 4-20 nucleotides. The UMI may comprise 8 to 16 nucleotides.

The isolated aggregation of cellular constituents may be a cell, an extracellular vesicle, an organelle, or an organized subcomponent thereof.

The sequencing may comprise combining a primer having a unique source identifier (USI) sequence with UCI, so that the USI and UCI sequences are sequenced together, and the USI preferably comprises 20 to 120 nucleotides.

The step of admixing the isolated aggregation of cellular constituents with monomers may be carried out in an aqueous aliquot or in a droplet formed by an aqueous solution in oil emulsion. The aqueous aliquot may be a separate reaction vessel such as a well in a plate. The droplet may be formed by a microfluidic device. The polymer matrix may be a hydrogel. The method may be a multiplex assay with a plurality of labeling ligands, each labeling ligand have a distinct UCI. The labeling ligand may be non-covalently bound to the target cellular constituent.

The method may further comprise pooling the oligonucleotide labels comprising a USI from a plurality of polymer matrices and sequencing the pooled UCI sequences and USI sequences. The method may further comprise pooling the oligonucleotide labels comprising a USI and UMI from a plurality of polymer matrices and sequencing the pooled UCI sequences, USI sequences, and UMI sequences.

The method may further comprise washing the cellular constituents embedded in the polymer matrices to remove selected cellular components from the polymer matrices before incubating the cellular constituents with the labeling ligand. The washing may comprise treating the cellular constituents embedded in the polymer matrices with a detergent so as to remove lipids from the polymer matrices before incubating the cellular constituents with the labeling ligand. The detergent may be an anionic detergent or non-ionic detergent. The detergent may be SDS, NP-40, triton X-100, or any other detergent known in the art capable of removing lipids.

The method may further comprise quantitating the relative amount of the UCI sequence associated with a first aggregation of cellular constituents to the amount of the same UCI sequence associated with a second aggregation of cellular constituents, whereby the relative differences of a cellular constituent between aggregations of cellular constituents are determined. The relative amount may be compared to a control sample. The control sample may have predetermined amounts of cellular constituents. There may be more than one control sample. There may be at least three control samples. The at least three control samples can be used to generate a standard curve upon which all of the other cellular constituents within discrete polymer matrices are compared. The control sample may comprise isolated aggregations of cellular constituents that were untreated as compared relative to isolated aggregations of cellular constituents that were treated with a different condition. Cells may be treated with drugs, small molecules, pathogens, hormones, cytokines, proteins, nucleic acids, virus particles, or grown in different cellular environments. Cells may be isolated from a diseased tissue. The cells from the diseased tissue may be compared to cells from non-diseased tissue. Cells may be treated with systems that knockout, decrease or increase expression of a gene. Cells may be treated with systems that knockout functional elements of a genome. Functional elements include, but are not limited to promoters, enhancers, repressors, centromeres, or telomeres. CRISPR systems may be used.

The labeling ligand may be an antibody or an antibody fragment. The antibody fragment may be a nanobody, Fab, Fab', (Fab')2, Fv, ScFv, diabody, triabody, tetrabody, BisscFv, minibody, Fab2, or Fab3 fragment. The labeling ligand may be an aptamer. The labeling ligand may be a nucleotide sequence complementary to a target sequence.

The method may comprise multiplex binding of two or more labeling ligands to each aggregation of cellular constituents. The two or more distinct labeling ligands may comprise complementary oligonucleotide sequences, so that binding of the labeling ligands to respective target cellular constituents that are in proximity permits the complementary sequences of the distinct ligands to hybridize, forming an amplifiable polynucleotide duplex. The method may further comprise amplifying the polynucleotide duplex to provide an amplified sequence that is a detectable signal that target cellular constituents are in proximity. The complementary oligonucleotide sequences, which serve as a start site for polymerase extension, can either be designed to query proximity of two specific cellular constituents, or it can be designed to be universal, thereby querying interactions between all members of the labeling ligand panel.

In one embodiment, at least two distinct labeling ligands comprise oligonucleotide sequences configured to be ligated, so that binding of the labeling ligands to respective target cellular constituents that are in proximity permits the oligonucleotide sequences of the distinct ligands to ligate, forming an amplifiable polynucleotide duplex. The method may further comprise amplifying the polynucleotide duplex to provide an amplified sequence that is a detectable signal that target cellular constituents are in proximity.

One of the labeling ligands may comprise an oligonucleotide label with a restriction enzyme site between the labeling ligand and the UCI, and wherein the method may further comprise treating with a restriction enzyme, whereby the UCI from the labeling ligand is transferred to the oligonucleotide label of the labeling ligand in proximity.

The method may further comprise labeling the aggregation of cellular constituents by fluorescent in situ hybridization.

The aggregation of cellular constituents may be a cell that is a member of a cell population. The cell may be transformed or transduced with one or more genomic sequence-perturbation constructs that perturb a genomic sequence in the cells, wherein each distinct genomic sequence-perturbation construct comprises a unique-perturbation-identifier (UPI) sequence unique to that construct. The genomic sequence-perturbation construct may comprise a sequence encoding a guide RNA sequence of a CRISPR-Cas targeting system. The method may further comprise multiplex transformation of the population of cells with a plurality of genomic sequence-perturbation constructs. The UPI sequence may be attached to a perturbation-sequence-capture sequence, and the microbeads may comprise a perturbation-sequence-capture-binding-sequence having specific binding affinity for the perturbation-sequence-capture sequence attached to the UPI sequence. The UPI sequence may be attached to a universal ligation handle sequence, whereby a USI may be generated by split-pool ligation. The method may further comprise multiplex sequencing of the pooled UCI sequences, USI sequences, and UPI sequences.

The oligonucleotide label may comprise a regulatory sequence configured for amplification by an RNA polymerase, such as T7 polymerase. The labeling ligands may comprise oligonucleotide sequences configured to hybridize to a transcript specific region. The oligonucleotide label may further comprise attachment chemistry, such as an acrylic phosphoramidite modification, whereby the modification allows for incorporation into the polymer matrices upon polymerization. The acrylic phosphoramidite may be Acrydite™ (Eurofins Scientific, Luxembourg). The method may further comprise amplification of the oligonucleotide label and USI by PCR or T7 amplification before sequencing. T7 amplification may be followed by cDNA generation and optionally amplification by PCR. The oligonucleotide label may further comprise at least one spacer sequence, preferably two spacer sequences. The oligonucleotide label may further comprise a photocleavable linker. The oligonucleotide label may further comprise a restriction enzyme site between the labeling ligand and UCI.

The discrete polymer matrices may be labeled and washed more than once. Discrete polymer matrices may be labeled with a marker specific for a cell type or cell cycle marker or developmental marker, or differentiation marker, or disease marker. The label may be a fluorescent label. The fluorescent label may be used to separate the discrete polymer matrices into distinct groups. The label may be used to identify a certain cell type prior to embedding it into a discrete polymer matrix. The discrete polymer matrices of a distinct group may then be labeled again with labeling ligands that contain an oligonucleotide label of the present invention. After novel information is obtained from the multiplex assay of the present invention, a 'banked' population of polymer matrices can be stained for newly identified markers and the population of interest can be sorted (enriched) for, and investigated more deeply.

In another aspect, the present invention provides a method of determining open chromatin in individual cells comprising: isolating single cells into droplets formed by an aqueous solution in oil emulsions, wherein the droplets further comprise Tn5-transposase loaded with two tagmentation adapters, wherein one adapter is configured for incorporation into a polymer matrix and the second adapter is configured with a ligation handle for generating a USI; incubating the droplets to allow cell lysis and tagmentation of open chromatin; infusing monomers of a polymerizable gel into the droplets; polymerizing the gel, to embed the cellular constituents in discrete polymer matrices; optionally incubating the polymer matrices with one or more labeling ligands with specific binding affinity for one or more target cellular constituents to produce one or more labeled cellular constituents in the polymer matrices, wherein each of the one or more labeling ligand comprises a bound oligonucleotide label comprising a unique constituent identifier (UCI) sequence and a sequence capable of hybridization to the tagmentation adapter configured for incorporation into a polymer matrix, and wherein the incubation comprises binding conditions under which the labeling ligand will bind to the cellular constituent within the polymer matrix and the oligonucleotide label will hybridize to said tagmentation adapter, and wherein the incubation further comprises washing conditions under which unbound labeling ligands will be washed out of the polymer matrix; and extending the genomic DNA and adapter DNA, whereby a continuous DNA strand is generated comprising the adapters, genomic DNA, and DNA overhang; optionally the oligonucleotide label bound to a labeling ligand; generating a USI at the DNA overhang by split-pool ligation; sequencing the continuous DNA strand, whereby open chromatin is determined and optionally the presence of a cellular constituent at a site of open chromatin is determined.

In another aspect, the present invention provides a method of measuring RNA levels in individual cells comprising: isolating single cells into droplets formed by an aqueous solution in oil emulsions, wherein the droplets comprise at least one labeling ligands specific for binding at one or more target RNA transcripts, wherein the labeling ligands are configured for incorporation into a polymer matrix and comprise a ligation handle for generating a USI; lysing the cells in the droplets under conditions wherein the labeling ligands will bind to the target RNA transcripts; injecting monomers of a polymerizable gel into the droplets; polymerizing the gel, to embed the labeling ligands in discrete polymer matrices; optionally, staining the discrete polymer matrices with at least one additional labeling ligand; generating a USI by split-pool ligation; and sequencing the resulting DNA, whereby RNA levels and optionally protein levels are determined in single cells. The droplets may comprise at least one pair of labeling ligands specific for binding at adjacent sites of one or more target RNA transcripts, wherein each pair of labeling ligands comprises one labeling ligand configured for incorporation into a polymer matrix and one labeling ligand comprising a ligation handle for generating a USI, and wherein the method may further comprise injecting a ligation reaction buffer comprising a ligase that is configured to allow ligation of the pair of labeling ligands if they are hybridized adjacently with single nucleotide resolution on the target RNA transcript, such that off target binding of labeling ligand does not get ligated, and will not be amplified in subsequent steps.

In another aspect, the present invention provides a method of assaying segregated cellular constituents, comprising: fixing and permeabilizing at least one cell; incubating the fixed and permeabilized cell(s) with one or more labeling ligands with specific binding affinity for one or more target cellular constituents to produce one or more labeled cell(s), wherein each of the one or more labeling ligands comprise a bound oligonucleotide label comprising a unique constituent identifier (UCI) sequence, and wherein the incubation comprises binding conditions under which the labeling ligand will bind to the cellular constituent within the cell(s), and the incubation further comprises washing conditions under which unbound labeling ligands will be washed from the cell(s); admixing the cell(s) with monomers of a polymerizable gel; isolating single cells into droplets formed by an aqueous solution in oil emulsions; polymerizing the gel, to embed the labeling ligands and other cellular constituents in discrete polymer matrices; optionally, staining the discrete polymer matrices with at least one additional labeling ligand; generating a USI by split-pool ligation; and sequencing the oligonucleotide label, whereby detecting the UCI by sequencing indicates the presence of the target cellular constituent. The labeling ligands in step (b) may comprise at least one pair of labeling ligands specific for binding at adjacent sites of one or more target RNA transcripts, wherein each pair of labeling ligands comprises one labeling ligand configured for incorporation into a polymer matrix and one labeling ligand comprising a ligation handle for generating a USI, and wherein the method further comprises ligating the pair of labeling ligands if they are within proximity after binding to the target RNA transcripts. Any of the preceding methods may comprise polymer matrices wherein they further comprise magnetic particles. In one embodiment, any hydrogel droplet encapsulated aggregations of cellular constituents may further comprise magnetic particles embedded into the droplets. Not being bound by a theory, magnetic particles enable magnetic separation, aiding in clean up and washing steps in multiple reactions. Not being bound by a theory, the use of magnetic particles greatly enhances automation and therefore throughput.

In another aspect, the present invention provides a method of assaying segregated cellular constituents, comprising: fixing and permeabilizing at least one cell; incubating the fixed and permeabilized cell(s) with one or more labeling ligands with specific binding affinity for one or more target cellular constituents to produce one or more labeled cell(s), wherein each of the one or more labeling ligands comprise a bound oligonucleotide label comprising a unique constituent identifier (UCI) sequence, and wherein the incubation comprises binding conditions under which the labeling ligand will bind to the cellular constituent within the cell(s), and the incubation further comprises washing conditions under which unbound labeling ligands will be washed from the cell(s); and sequencing the oligonucleotide label, whereby detecting the UCI by sequencing indicates the presence of the target cellular constituent. The cellular constituent may comprise a protein, RNA transcript, or a DNA molecule. The method may further comprise segregating the cell(s) before sequencing. The segregating the cell(s) may comprise sorting the single cell(s) into a separate reaction vessel(s). The segregating the cell(s) may comprise forming discrete unique-identifier-transfer compositions, each comprising a cell and a transfer particle, wherein: the oligonucleotide label further comprises a capture sequence, and the UCI and capture sequence are together releasably attached to the labeling ligand; the labelling ligand is bound to the target cellular constituent; and, the transfer particle comprises: a capture-binding-sequence having specific binding affinity for the capture sequence attached to the UCI, and, a unique source identifier (USI) sequence that is unique to each transfer particle, and the USI preferably comprises 4-15 nucleotides. The method may further comprise releasing the UCI from the labeled ligand, under conditions within the unique-identifier-transfer composition so that the released capture sequence binds to the capture-binding-sequence on the transfer particle, thereby transferring the UCI to the transfer particle. The method may further comprise, before sequencing in step, generating a USI for each cell(s) by a split pool ligation method, wherein the oligonucleotide label further comprises a universal ligation handle (ULH) sequence configured to produce a DNA overhang capable of hybridization to a complementary overhang on a first index nucleotide sequence, wherein the first index nucleotide sequence comprises an overhang complementary to a final index sequence or optionally a middle index sequence, wherein the middle index sequence comprises overhangs complementary to the first index sequence and to the final index sequence or optionally to another middle index sequence and final index sequence, wherein the final index sequence has a single overhang complementary to the preceding index sequence, and wherein the first, middle, and final index sequences are selected from a plurality of unique sequences comprising compatible DNA overhangs and 10 to 30 base pairs of unique sequence. The split pool ligation method may comprise: splitting the pool of cell(s) into separate pools of cell(s), each containing a unique first index sequence; ligating the first index sequence to the ligation handle; pooling the cell(s); optionally, splitting the pool of cell(s) into separate pools each containing a unique middle index sequence; ligating the middle index sequence to the first index sequence; and pooling the cell(s); optionally, repeating with another middle index sequence; splitting the pool of cell(s) into pools containing a unique final index sequence; and ligating the final index sequence to the preceding index sequence, whereby each cell comprises a USI.

The ligation handle may comprise a restriction site for producing an overhang complementary with a first index sequence overhang, and wherein the method further comprises digestion with a restriction enzyme. The ligation handle may comprise a nucleotide sequence complementary with a ligation primer sequence and wherein the overhang complementary with a first index sequence overhang is produced by hybridization of the ligation primer to the ligation handle.

The UCI may comprise 4 to 30 nucleotides, or 7 to 30 nucleotides, or about 21 nucleotides. The oligonucleotide label may further comprise a unique molecular identifier (UMI) sequence. The first, middle, or final index sequence may further comprise a unique molecular identifier (UMI) sequence. The UMI may be 4-20 nucleotides. The UMI may be 8 to 16 nucleotides.

The sequencing may comprise combining a primer having a unique source identifier (USI) sequence with UCI, so that the USI and UCI sequences are sequenced together, and the USI preferably comprises 20 to 120 nucleotides.

The method may comprise a multiplex assay with a plurality of labeling ligands, each labeling ligand have a distinct UCI. The labeling ligand may be non-covalently bound to the target cellular constituent. The method may further comprise pooling the oligonucleotide labels comprising a USI from a plurality of cells and sequencing the pooled UCI sequences and USI sequences. The method may further comprise pooling the oligonucleotide labels comprising a USI and UMI from a plurality of cells and sequencing the pooled UCI sequences, USI sequences, and UMI sequences. The method may further comprise quantitating the relative amount of the UCI sequence associated with a first cell to the amount of the same UCI sequence associated with a second cell, whereby the relative differences of a cellular constituent between cell(s) are determined.

The labeling ligand may be an antibody or an antibody fragment. The antibody fragment may be a nanobody, Fab, Fab', (Fab')2, Fv, ScFv, diabody, triabody, tetrabody, BisscFv, minibody, Fab2, or Fab3 fragment. The labeling ligand may be an aptamer. The labeling ligand may be a nucleotide sequence complementary to a target sequence.

The method may comprise multiplex binding of two or more labeling ligands to the cellular constituents. At least two distinct labeling ligands may comprise complementary oligonucleotide sequences, so that binding of the labeling ligands to respective target cellular constituents that are in proximity permits the complementary sequences of the distinct ligands to hybridize, forming an amplifiable polynucleotide duplex. The method may further comprise amplifying the polynucleotide duplex to provide an amplified sequence that is a detectable signal that target cellular constituents are in proximity. At least two distinct labeling ligands may comprise oligonucleotide sequences configured to be ligated, so that binding of the labeling ligands to respective target cellular constituents that are in proximity permits the oligonucleotide sequences of the distinct ligands to ligate, forming an amplifiable polynucleotide duplex. The method may further comprise amplifying the polynucleotide duplex to provide an amplified sequence that is a detectable signal that target cellular constituents are in proximity. One of the labeling ligands may comprise a restriction enzyme site between the labeling ligand and the oligonucleotide label, and wherein the method further comprises treating with a restriction enzyme, whereby the UCI from said labeling ligand is transferred to the oligonucleotide label of the labeling ligand in proximity.

The method may further comprise labeling the cell(s) by fluorescent in situ hybridization.

The cell(s) may be a member of a cell population, further comprising transforming or transducing the cell population with one or more genomic sequence-perturbation constructs that perturb a genomic sequence in the cells, wherein each distinct genomic sequence-perturbation construct comprises a unique-perturbation-identified (UPI) sequence unique to that construct. The genomic sequence-perturbation construct may comprise a sequence encoding a guide RNA sequence of a CRISPR-Cas targeting system. The method may further comprise multiplex transformation of the population of cells with a plurality of genomic sequence-perturbation constructs. The UPI sequence may be attached to a perturbation-sequence-capture sequence, and the transfer particle may comprise a perturbation-sequence-capture-binding-sequence having specific binding affinity for the perturbation-sequence-capture sequence attached to the UPI sequence. The UPI sequence may be attached to a universal ligation handle sequence, whereby a USI may be generated by split-pool ligation. The method may further comprise multiplex sequencing of the pooled UCI sequences, USI sequences, and UPI sequences.

In another aspect, the present invention provides a method of determining interactions between 2 or more cellular constituents, comprising: admixing at least one isolated aggregation of cellular constituents with monomers of a polymerizable gel; polymerizing the gel, to embed the cellular constituents in discrete polymer matrices; incubating the cellular constituents embedded in the polymer matrices with one or more labeling ligands with specific binding affinity for one or more target cellular constituents to produce one or more labeled cellular constituents in the polymer matrices, wherein each of the one or more labeling ligands comprise a bound oligonucleotide label comprising a unique constituent identifier (UCI) sequence and a universal hybridization nucleotide sequence, and wherein the incubation comprises binding conditions under which the labeling ligand will bind to the cellular constituent within the polymer matrix, and the incubation further comprises washing conditions under which unbound labeling ligands will be washed out of the polymer matrix; incubating the polymer matrices with at least one Unique Location Index probe, wherein the probe comprises at least two repeating nucleotide sequences, each repeat comprising a restriction enzyme site, a Unique Location Index (ULI) sequence, and a complementary universal hybridization nucleotide sequence, and wherein the incubation comprises binding conditions under which the universal hybridization sequence will hybridize the complementary universal hybridization sequence; extending the oligonucleotide label hybridized to the probe such that the oligo bound to the affinity ligand incorporates the ULI sequence that is unique to that Unique Location Index probe; digestion with a restriction enzyme specific for the site on the probe, sequencing the oligonucleotide label, whereby detecting the same ULI with two or more UCI's indicates that the cellular constituents were interacting. The ULI sequence may be randomly generated, such that no two ULI sequences are the same. Methods of generating a barcode sequence described herein may be used to generate a ULI. The ULI will be detected with the UCI, such that when multiple cellular constituents are in proximity oligonucleotide labels comprising each UCI and the ULI from a single probe will be generated. Not being bound by a theory, using a plurality of labeling ligands with specificity for a plurality of cellular constituents will allow novel interactions to be determined. The use of polymer matrices allows a stable platform for washing out the unbound labeling ligands before staining with the ULI probes. The cellular constituent may comprise a protein, RNA transcript, or a DNA molecule. The ULI may be 4-30 nucleotides. The ULI may be 8-20 nucleotides.

The method may further comprise segregating the discrete polymer matrices comprising the labeled constituents before sequencing. The segregating of the discrete polymer matrices may comprise sorting single discrete matrices into separate reaction vessels.

The method may further comprise, before sequencing, generating a USI for each discrete polymer matrix by a split pool ligation method, wherein the restriction site on the ULI probe is a universal ligation handle (ULH) sequence configured to produce a DNA overhang capable of hybridization to a complementary overhang on a first index nucleotide sequence, wherein the first index nucleotide sequence comprises an overhang complementary to a final index sequence or optionally a middle index sequence, wherein the middle index sequence comprises overhangs complementary to the first index sequence and to the final index sequence or optionally to another middle index sequence and final index sequence, wherein the final index sequence has a single overhang complementary to the preceding index sequence, and wherein the first, middle, and final index sequences are selected from a plurality of unique sequences comprising compatible DNA overhangs and 10 to 30 base pairs of unique sequence. The split pool ligation method may comprise: splitting the pool of discrete polymer matrices into separate pools of polymer matrices, each containing a unique first index sequence; ligating the first index sequence to the ligation handle; pooling the discrete polymer matrices; optionally, splitting the pool of discrete polymer matrices into separate pools each containing a unique middle index sequence; ligating the middle index sequence to the first index sequence; and pooling the discrete polymer matrices; optionally, repeating step (d) with another middle index sequence; splitting the pool of discrete polymer matrices into pools containing a unique final index sequence; and ligating the final index sequence to the preceding index sequence, whereby each discrete polymer matrix comprises a USI.

The oligonucleotide label may further comprise a unique molecular identifier (UMI) sequence. The first, middle, or final index sequence may further comprise a unique molecular identifier (UMI) sequence. The method may further comprise pooling the oligonucleotide labels comprising a USI, ULI and UMI from a plurality of polymer matrices and sequencing the pooled UCI sequences, USI sequences, ULI sequences, and UMI sequences.

The aggregation of cellular constituents may be a cell that is a member of a cell population, further comprising transforming or transducing the cell population with one or more genomic sequence-perturbation constructs that perturb a genomic sequence in the cells, wherein each distinct genomic sequence-perturbation construct comprises a unique-perturbation-identified (UPI) sequence unique to that construct.

In another aspect, the present invention provides a method of determining interactions between 2 or more cellular constituents, comprising: fixing and permeabilizing at least one cell; incubating the fixed and permeabilized cell(s) with one or more labeling ligands with specific binding affinity for one or more target cellular constituents to produce one or more labeled cell(s), wherein each of the one or more labeling ligands comprise a bound oligonucleotide label comprising a unique constituent identifier (UCI) sequence and a universal hybridization nucleotide sequence, and wherein the incubation comprises binding conditions under which the labeling ligand will bind to the cellular constituent within the cell(s), and the incubation further comprises washing conditions under which unbound labeling ligands will be washed from the polymer cell(s); incubating the cell(s) with at least one Unique Location Index probe, wherein the probe comprises at least two repeating nucleotide sequences, each repeat comprising a restriction enzyme site, a Unique Location Index (ULI) sequence, and a complementary universal hybridization nucleotide sequence, and wherein the incubation comprises binding conditions under which the universal hybridization sequence will hybridize to the complementary universal hybridization sequence; extending the oligonucleotide label hybridized to the probe; digesting with a restriction enzyme specific for the site on the probe; and sequencing the oligonucleotide label, whereby detecting the same ULI with two or more UCI's indicates that the cellular constituents were interacting. The cellular constituent may comprise a protein, RNA transcript, or a DNA molecule. The ULI may be 4-30 nucleotides. The ULI may be 8-20 nucleotides.

The method may further comprise segregating the cell(s) comprising the labeled constituents before sequencing. The segregating of the cell(s) may comprise sorting single discrete matrices into separate reaction vessels. The method may further comprise, before sequencing, generating a USI for each cell by a split pool ligation method, wherein the restriction site on the ULI probe is a universal ligation handle (ULH) sequence configured to produce a DNA overhang capable of hybridization to a complementary overhang on a first index nucleotide sequence, wherein the first index nucleotide sequence comprises an overhang complementary to a final index sequence or optionally a middle index sequence, wherein the middle index sequence comprises overhangs complementary to the first index sequence and to the final index sequence or optionally to another middle index sequence and final index sequence, wherein the final index sequence has a single overhang complementary to the preceding index sequence, and wherein the first, middle, and final index sequences are selected from a plurality of unique sequences comprising compatible DNA overhangs and 10 to 30 base pairs of unique sequence. The split pool ligation method may comprise: splitting the pool of cells into separate pools of cells, each containing a unique first index sequence; ligating the first index sequence to the ligation handle; pooling the cells; optionally, splitting the pool of cells into separate pools each containing a unique middle index sequence; ligating the middle index sequence to the first index sequence; and pooling the cells; optionally, repeating with another middle index sequence; splitting the pool of cells into pools containing a unique final index sequence; and ligating the final index sequence to the preceding index sequence, whereby each cell comprises a USI.

The oligonucleotide label may further comprise a unique molecular identifier (UMI) sequence. The first, middle, or final index sequence may further comprise a unique molecular identifier (UMI) sequence. The method may further comprise pooling the oligonucleotide labels comprising a USI, ULI and UMI from a plurality of polymer matrices and sequencing the pooled UCI sequences, USI sequences, ULI sequences, and UMI sequences.

The cells may be a member of a cell population, further comprising transforming or transducing the cell population with one or more genomic sequence-perturbation constructs that perturb a genomic sequence in the cells, wherein each distinct genomic sequence-perturbation construct comprises a unique-perturbation-identified (UPI) sequence unique to that construct. The perturbation constructs may be any as described herein.

The oligonucleotide label may comprise a regulatory sequence configured for amplification by T7 polymerase.

The labeling ligands may comprise oligonucleotide sequences configured to hybridize to a transcript specific region.

Before sequencing, the method may further comprise: amplification of the oligonucleotide label by PCR; or T7 amplification of the oligonucleotide label followed by subsequent cDNA generation, and optionally amplification by PCR.

The oligonucleotide label may further comprise at least one spacer sequence. The oligonucleotide label may further comprise a photocleavable linker. The oligonucleotide label may further comprise a restriction enzyme site between the labeling ligand and UCI.

The oligonucleotide label may comprise one or more iso-dG and/or iso-dC nucleotides. The oligonucleotide labels for hybridization in a proximity assay may comprise one or more iso-dG and/or iso-dC nucleotides. The universal hybridization sequences may comprise one or more iso-dG and/or iso-dC nucleotides. Not being bound by a theory the one or more iso-dG and/or iso-dC nucleotides will increase specificity of hybridization.

In one embodiment, the oligonucleotide label of any of the methods described herein may comprise one or more iso-dG and/or iso-dC nucleotides. Two complementary sequences may comprise one sequence with iso-dG and the other complementary sequence with iso-dC, whereby the two sequences are capable of hybridizing with each other, but not with sequences containing only dG, dC, dA, and/or dT. The sequence of the oligonucleotide labels for hybridization in a proximity assay may advantageously comprise one or more iso-dG and/or iso-dC nucleotides.

Any of the methods of the present invention may advantageously be combined for determining any combination of protein detection, RNA detection, open chromatin detection, protein-protein interactions, protein-RNA interactions, or protein-DNA interactions.

Accordingly, it is an object of the invention to not encompass within the invention any previously known product, process of making the product, or method of using the product such that Applicants reserve the right and hereby disclose a disclaimer of any previously known product, process, or method. It is further noted that the invention does not intend to encompass within the scope of the invention any product, process, or making of the product or method of using the product, which does not meet the written description and enablement requirements of the USPTO (35 U.S.C. § 112, first paragraph) or the EPO (Article 83 of the EPC), such that Applicants reserve the right and hereby disclose a disclaimer of any previously described product, process of making the product, or method of using the product.

It is noted that in this disclosure and particularly in the claims and/or paragraphs, terms such as "comprises", "comprised", "comprising" and the like can have the meaning attributed to it in U.S. patent law; e.g., they can mean "includes", "included", "including", and the like; and that terms such as "consisting essentially of" and "consists essentially of" have the meaning ascribed to them in U.S. patent law, e.g., they allow for elements not explicitly recited, but exclude elements that are found in the prior art or that affect a basic or novel characteristic of the invention. Nothing herein is intended as a promise.

These and other aspects, objects, features, and advantages of the example embodiments will become apparent to those having ordinary skill in the art upon consideration of the following detailed description of illustrated example embodiments.

This patent or patent application file contains at least one drawing executed in color. Copies of this patent or patent application publication with color drawing(s) may be provided by the Office upon request and payment of the necessary fee.

BRIEF DESCRIPTION OF THE DRAWINGS

The following detailed description, given by way of example, but not intended to limit the invention solely to the specific embodiments described, may best be understood in conjunction with the accompanying drawings, in which:

FIG. 2A provides an overlay of transmission light microscopy image epifluorescent measurement of CD51/Alexa488. Black arrow indicates an example of a hydrogel embedded cell, the white arrow indicates an empty hydrogel droplet, staining negative for CD51. FIG. 2B provides the same cells, stained for genomic DNA DAPI and intracellular PCNA/Alexa647. FIG. 2C provides a strong Pearson correlation (0.98) measured between fluorescence levels of 'endogenous' GFP levels from 293/GFP cells, and a detecting anti-GFP antibody conjugated to Alexa647. Similar staining with the BD cytofix/perm kit yielded a Pearson correlation of 0.36.

FIG. 10 illustrates the generation of an Index A+UMI.

FIG. 14 illustrates high throughput single-cell ATAC-seq.

FIG. 15 illustrates high throughput single-cell measuring protein-DNA complexes.

FIG. 18 illustrates the generation of an Index C+UMI.

FIG. 20 illustrates a novel probe for detection of complexes consisting of more than 2 cellular constituents at the same time. The probe includes a Unique Location Identifier (ULI). It can be constructed by rolling circle amplification.

FIG. 21 illustrates the overall scheme to measure the proximity of 3 or more proteins, RNA or DNA molecules. The hybridization sequence of the ligand bound oligo binds to the complementary hybridization site on the ULI probe. By extension, each ligand bound oligo incorporates the same ULI. Restriction enzyme digestion generates a 4 bp overhang. Sticky end ligation is used to attach a USI+UMI.

DETAILED DESCRIPTION OF THE EXAMPLE EMBODIMENTS

Overview

Figure 1:
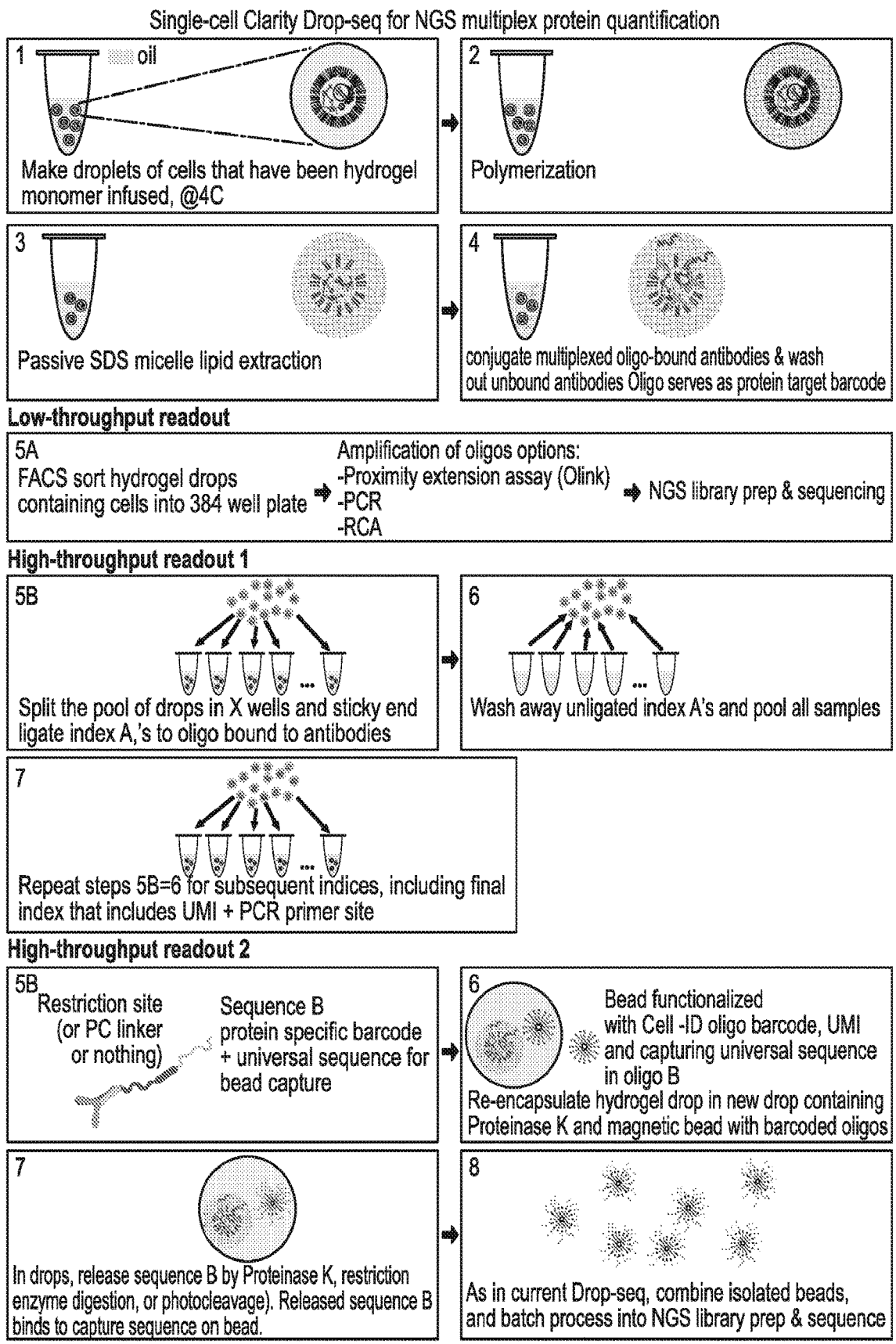
FIG. 1 illustrates a schematic overview of embodiments using hydrogel embedding of single cells, followed by lipid clearing and DNA-tagged antibody labeling. Also shown, are low-throughput and high-throughput readouts.

The terms "isolated aggregation of cellular constituents" or "single aggregations of cellular constituents" or "aggregations of cellular constituents" or "aggregations of biologically connected cellular constituents" are used interchangeably and refer to any group of cellular constituents that originate from the same source, that are functionally connected biologically, and that can be isolated individually. Examples may be a cell, an extracellular vesicle, an organelle, or an organized subcomponent thereof. Specific examples may be a nucleus or a mitochondria.

The term "cellular constituent" refers to any cellular molecule, including but not limited to a protein, nucleic acid, RNA molecule, DNA molecule, or carbohydrate.

The term "unique molecular identifiers" (UMI) refers to a sequencing linker used in a method that uses molecular tags to detect and quantify unique amplified products. A UMI is used to distinguish effects through a single clone from multiple clones. In preferred embodiments, the amplification is by PCR. A sequencer linker with a random sequence of between 4 and 20 base pairs and an index sequence is added to the 5' end of the template, which is amplified and sequenced. Sequencing allows for high resolution reads, enabling accurate detection of true variants. As used herein, a "true variant" will be present in every amplified product originating from the original clone as identified by aligning all products with a UMI. Each clone amplified will have a different random UMI that will indicate that the amplified product originated from that clone. Background caused by the fidelity of the amplification process can be eliminated because true variants will be present in all amplified products and background representing random error will only be present in single amplification products (See e.g., Islam S. et al., 2014. Nature Methods No: 11, 163-166). Not being bound by a theory, the UMI and UCI's are designed such that assignment to the original can take place despite up to 4-7 errors during amplification or sequencing.

The term "unique constituent identifier" (UCI) refers to any unique nucleotide sequence linked to a labeling ligand, such that the presence of the sequence indicates the presence of the cellular constituent that the labeling ligand specifically binds. In an exemplary embodiment, the UCI is linked to an antibody for a specific cellular constituent. If the cellular constituent is present in a sample, the antibody will bind and the UCI can be detected. If the cellular constituent is not present in a sample, the antibody will not bind and the UCI will not be detected above background. In another exemplary embodiment, the labeling ligand is an oligonucleotide probe and the cellular constituent is an RNA transcript molecule complementary to the sequence of the oligonucleotide probe. The sequence of the oligonucleotide probe may be the UCI or may comprise an additional UCI sequence to identify the RNA transcript.

The term "unique source identifier" (USI) refers to a unique nucleotide sequence that is associated with the nucleic acids from a single cell or single isolated aggregation of cellular constituents (source), such that upon sequencing a pool of nucleic acid sequences from more than one cell or isolated aggregation of cellular constituents, the presence of a USI in the sequenced product indicates that a product originated from a single source. USI may be used interchangeably with the term "barcode."

The term "unique-amplification-identifier" (UAI) refers to a nucleotide sequence that is only formed only when two or more nucleotide sequences are in close proximity to each other such that they can be ligated. The UAI can be generated using methods described for the proximity ligation assay (PLA) or proximity extension assay (PEA) (Fredriksson S, et al. (2002) Protein detection using proximity-dependent DNA ligation assays. Nature biotechnology 20: 473-477; Gullberg M, et al. (2004) Cytokine detection by antibody-based proximity ligation. Proceedings of the National Academy of Sciences of the United States of America 101: 8420-8424; and Lundberg M, et al. (2011) Homogeneous antibody-based proximity extension assays provide sensitive and specific detection of low-abundant proteins in human blood. Nucleic acids research 39(15): e102). PEA is based on pairs of antibodies that are linked to oligonucleotides having slight affinity to one another (PEA probes). Upon target binding the probes are brought in proximity, and the two oligonucleotides are extended by a DNA polymerase forming the UAI that now acts as a unique surrogate marker for the specific antigen.

The terms "sticky end," "overhang" and "DNA overhang" refer to a double stranded DNA having either a 3' or 5' single stranded DNA overhang capable of hybridization to another complementary sticky end or DNA overhang.

The term "hydrogel" refers to any network of polymer chains that are hydrophilic, and sometimes found as a colloidal gel, in which water is the dispersion medium. Hydrogels are highly absorbent (they can contain over 90% water) natural or synthetic polymeric networks. Hydrogels also possess a degree of flexibility very similar to natural tissue, due to their significant water content. Hydrogel may include polyvinyl alcohol, sodium polyacrylate, acrylate polymers, copolymers with an abundance of hydrophilic groups, agarose, methylcellulose, hyaluronan, and other naturally derived polymers.

The term "tagmentation" refers to a step in the Assay for Transposase Accessible Chromatin using sequencing (ATAC-seq) as described. (See, Buenrostro, J. D., Giresi, P. G., Zaba, L. C., Chang, H. Y., Greenleaf, W. J., Transposition of native chromatin for fast and sensitive epigenomic profiling of open chromatin, DNA-binding proteins and nucleosome position. Nature methods 2013; 10 (12): 1213-1218). Specifically, a hyperactive Tn5 transposase loaded in vitro with adapters for high-throughput DNA sequencing, can simultaneously fragment and tag a genome with sequencing adapters. In one embodiment the adapters are compatible with the methods described herein.

The present invention may also include barcoding. Barcoding may be performed based on any of the compositions or methods disclosed in patent publication WO 2014047561 A1, Compositions and methods for labeling of agents, incorporated herein in its entirety. In one embodiment each labeling ligand has a barcode (UCI). In one embodiment, a sgRNA has a barcode. In one embodiment the UCI is captured on a bead that includes a barcode sequence (USI). Not being bound by a theory, amplified sequences from single cells or isolated aggregations of cellular constituents can be sequenced together and resolved based on the barcode associated with each USI. Not being bound by a theory, the presence of a labeling ligand can be determined by sequencing of the UCI.

The term "barcode" as used herein, refers to any unique, non-naturally occurring, nucleic acid sequence that may be used to identify the originating source of a nucleic acid fragment. Such barcodes may be sequences including but not limited to, TTGAGCCT, AGTTGCTT, CCAGTTAG, ACCAACTG, GTATAACA or CAGGAGCC. Although it is not necessary to understand the mechanism of an invention, it is believed that the barcode sequence provides a high-quality individual read of a barcode associated with a viral vector, labeling ligand, shRNA, sgRNA or cDNA such that multiple species can be sequenced together.

DNA barcoding is also a taxonomic method that uses a short genetic marker in an organism's DNA to identify it as belonging to a particular species. It differs from molecular phylogeny in that the main goal is not to determine classification but to identify an unknown sample in terms of a known classification. Kress et al., "Use of DNA barcodes to identify flowering plants" Proc. Natl. Acad. Sci. U.S.A. 102(23):8369-8374 (2005). Barcodes are sometimes used in an effort to identify unknown species or assess whether species should be combined or separated. Koch H., "Combining morphology and DNA barcoding resolves the taxonomy of Western Malagasy Liotrigona Moure, 1961" African Invertebrates 51(2): 413-421 (2010); and Seberg et al., "How many loci does it take to DNA barcode a crocus?" PLoS One 4(2):e4598 (2009). Barcoding has been used, for example, for identifying plant leaves even when flowers or fruit are not available, identifying the diet of an animal based on stomach contents or feces, and/or identifying products in commerce (for example, herbal supplements or wood). Soininen et al., "Analysing diet of small herbivores: the efficiency of DNA barcoding coupled with high-throughput pyrosequencing for deciphering the composition of complex plant mixtures" Frontiers in Zoology 6:16 (2009).

It has been suggested that a desirable locus for DNA barcoding should be standardized so that large databases of sequences for that locus can be developed. Most of the taxa of interest have loci that are sequencable without species-specific PCR primers. CBOL Plant Working Group, "A DNA barcode for land plants" PNAS 106(31):12794-12797 (2009). Further, these putative barcode loci are believed short enough to be easily sequenced with current technology. Kress et al., "DNA barcodes: Genes, genomics, and bioinformatics" PNAS 105(8):2761-2762 (2008). Consequently, these loci would provide a large variation between species in combination with a relatively small amount of variation within a species. Lahaye et al., "DNA barcoding the floras of biodiversity hotspots" Proc Natl Acad Sci USA 105(8): 2923-2928 (2008).

DNA barcoding is based on a relatively simple concept. For example, most eukaryote cells contain mitochondria, and mitochondrial DNA (mtDNA) has a relatively fast mutation rate, which results in significant variation in mtDNA sequences between species and, in principle, a comparatively small variance within species. A 648-bp region of the mitochondrial cytochrome c oxidase subunit 1 (CO1) gene was proposed as a potential 'barcode'. As of 2009, databases of CO1 sequences included at least 620,000 specimens from over 58,000 species of animals, larger than databases available for any other gene. Ausubel, J., "A botanical macroscope" Proceedings of the National Academy of Sciences 106(31):12569 (2009).

Software for DNA barcoding requires integration of a field information management system (FIMS), laboratory information management system (LIMS), sequence analysis tools, workflow tracking to connect field data and laboratory data, database submission tools and pipeline automation for scaling up to eco-system scale projects. Geneious Pro can be used for the sequence analysis components, and the two plugins made freely available through the Moorea Biocode Project, the Biocode LIMS and Genbank Submission plugins handle integration with the FIMS, the LIMS, workflow tracking and database submission.

Additionally, other barcoding designs and tools have been described (see e.g., Birrell et al., (2001) Proc. Natl Acad. Sci. USA 98, 12608-12613; Giaever, et al., (2002) Nature 418, 387-391; Winzeler et al., (1999) Science 285, 901-906; and Xu et al., (2009) Proc Natl Acad Sci USA. February 17; 106(7):2289-94).

The invention provides a method for preparing uniquely barcoded particles. Unique barcode sequences may be generated by a split pool method. The split pool method may include sticky end ligation. Sticky end ligation may include a sticky end ligation handle and separate indexes containing unique sequences capable of hybridizing to a sticky end (see examples). The sticky end may comprise a ssDNA overhang. The overhang may be 2, 3, 4, 5, 6, 7, 8, preferably 4 bases. The overhang may be generated by a restriction enzyme. Each index may contain a plurality of unique sequences. Each index may contain 10, 20, 30, 40, 50, 60, 70, 80, 90, 100, 200, preferably 192 sequences. In one embodiment there are 2, 3, 4, preferably 3 indexes. A unique barcode sequence is generated by ligation of the first index to the ligation handle, splitting and pooling of the ligated samples, and then addition of the next index also containing sticky ends. The last index preferably has a sticky end for ligation to the previous index. The last index may advantageously include a primer sequence for priming of PCR. Methods of split pooling have been described. In one embodiment the ligation handle is digested with a restriction enzyme to produce a four base overhang. In another embodiment, a ligation primer is hybridized to the ligation handle to generate an at least 4 base overhang that is complementary to an index in the split pool method.

In one exemplary embodiment, the hydrogel particles or polymer matrices are split into pools, each pool containing a unique index A and each ligation handle is ligated to a sequence in index A. All particles are then pooled and re-split into new pools containing a unique index B. After ligation, all of the particles are pooled again and re-split into new pools containing a unique index C. If each index has 100 unique sequences and for each cycle the particles are split into 100 pools each containing a unique sequence, then after 3 cycles of split and pool ligation, the barcode on any given particle possess the same one of $100^3=1,000,000$ possible barcodes, but different particles have different sequences.

In another embodiment, single cell or single isolated aggregation of cellular constituent analysis is performed by digital polymerase chain reactions (PCR), e.g., Fluidigm C. Digital polymerase chain reaction (digital PCR, DigitalPCR, dPCR, or dePCR) is a refinement of conventional polymerase chain reaction methods that can be used to directly quantify and clonally amplify nucleic acids including DNA, cDNA or RNA. The key difference between dPCR and traditional PCR lies in that PCR carries out one reaction per single sample and dPCR carries out a single reaction within samples separated into a large number of partitions wherein the reactions are carried out in each partition individually. A sample is partitioned so that individual nucleic acid molecules within the sample are localized and concentrated within many separate regions. The capture or isolation of individual nucleic acid molecules may be effected in micro well plates, capillaries, the dispersed phase of an emulsion, and arrays of miniaturized chambers, as well as on nucleic acid binding surfaces.

In a preferred embodiment, single cell or single aggregation of cellular constituent analysis is performed using microfluidics. Microfluidics involves micro-scale devices that handle small volumes of fluids. Because microfluidics may accurately and reproducibly control and dispense small fluid volumes, in particular volumes less than 1 μl, application of microfluidics provides significant cost-savings. The use of microfluidics technology reduces cycle times, shortens time-to-results, and increases throughput. Furthermore, incorporation of microfluidics technology enhances system integration and automation. Microfluidic reactions are generally conducted in microdroplets. The ability to conduct reactions in microdroplets depends on being able to merge different sample fluids and different microdroplets. See, e.g., US Patent Publication No. 20120219947 and PCT publication No. WO2014085802 A 1.

Droplet microfluidics offers significant advantages for performing high-throughput screens and sensitive assays. Droplets allow sample volumes to be significantly reduced, leading to concomitant reductions in cost. Manipulation and measurement at kilohertz speeds enable up to $10^8$ samples to be screened in a single day. Compartmentalization in droplets increases assay sensitivity by increasing the effective concentration of rare species and decreasing the time required to reach detection thresholds. Droplet microfluidics combines these powerful features to enable currently inaccessible high-throughput screening applications, including single-cell and single-molecule assays. See, e.g., Guo et al., Lab Chip, 2012, 12, 2146-2155.

The manipulation of fluids to form fluid streams of desired configuration, discontinuous fluid streams, droplets, particles, dispersions, etc., for purposes of fluid delivery, product manufacture, analysis, and the like, is a relatively well-studied art. Microfluidic systems have been described in a variety of contexts, typically in the context of miniaturized laboratory (e.g., clinical) analysis. Other uses have been described as well. For example, WO 2001/89788; WO 2006/040551; U.S. Patent Application Publication No. 2009/0005254; WO 2006/040554; U.S. Patent Application Publication No. 2007/0184489; WO 2004/002627; U.S. Pat. No. 7,708,949; WO 2008/063227; U.S. Patent Application Publication No. 2008/0003142; WO 2004/091763; U.S. Patent Application Publication No. 2006/0163385; WO 2005/021151; U.S. Patent Application Publication No. 2007/0003442; WO 2006/096571; U.S. Patent Application Publication No. 2009/0131543; WO 2007/089541; U.S. Patent Application Publication No. 2007/0195127; WO 2007/081385; U.S. Patent Application Publication No. 2010/0137163; WO 2007/133710; U.S. Patent Application Publication No. 2008/0014589; U.S. Patent Application Publication No. 2014/0256595; and WO 2011/079176. In a preferred embodiment single cell analysis is performed in droplets using methods according to WO 2014085802. Each of these patents and publications is herein incorporated by reference in their entireties for all purposes.

Single cells or isolated aggregations of cellular constituents may be sorted into separate vessels by dilution of the sample and physical movement, such as pipetting. A machine can control the pipetting and separation. The machine may be a computer controlled robot.

Microfluidics may also be used to separate the single cells and/or isolated aggregations of cellular constituents. Single cells and/or isolated aggregations of cellular constituents can be separated using microfluidic devices. Microfluidics involves micro-scale devices that handle small volumes of fluids. Because microfluidics may accurately and reproducibly control and dispense small fluid volumes, in particular volumes less than 1 μl, application of microfluidics provides significant cost-savings. The use of microfluidics technology reduces cycle times, shortens time-to-results, and increases throughput. The small volume of microfluidics technology improves amplification and construction of DNA libraries made from single cells and single isolated aggregations of cellular constituents. Furthermore, incorporation of microfluidics technology enhances system integration and automation.

Single cells and/or single isolated aggregations of cellular constituents of the present invention may be divided into single droplets using a microfluidic device. The single cells and/or single isolated aggregations of cellular constituents in such droplets may be further labeled with a barcode. In this regard reference is made to Macosko et al., 2015, "Highly Parallel Genome-wide Expression Profiling of Individual Cells Using Nanoliter Droplets" Cell 161, 1202-1214 and Klein et al., 2015, "Droplet Barcoding for Single-Cell Transcriptomics Applied to Embryonic Stem Cells" Cell 161, 1187-120, 1 all the contents and disclosure of each of which are herein incorporated by reference in their entirety. Not being bound by a theory, the volume size of an aliquot within a droplet may be as small as 1 fL.

Single cells and/or single aggregations of cellular constituents may be diluted into a physical multi-well plate or a plate free environment. The multi-well assay modules (e.g., plates) may have any number of wells and/or chambers of any size or shape, arranged in any pattern or configuration, and be composed of a variety of different materials. Preferred embodiments of the invention are multi-well assay plates that use industry standard multi-well plate formats for the number, size, shape and configuration of the plate and wells. Examples of standard formats include 96-, 384-, 1536- and 9600-well plates, with the wells configured in two-dimensional arrays. Other formats include single well, two well, six well and twenty-four well and 6144 well plates. Plate free environments of the present invention utilize a single polymerizable gel containing compartmentalized cells and/or isolated aggregations of cellular constituents. In one embodiment, extraction of single cells and/or single isolated aggregations of cellular constituents may be by a mechanical punch. Single cells and/or single isolated aggregations of cellular constituents may be visualized in the gel before a punch.

In one embodiment, a DNA tag including a protein specific barcode (UCI) is conjugated to detection biomolecules or labeling ligands with high target affinity and low unspecific binding, such as antibodies (Janssen et al., 2013) or nanobodies (Pardon et al., 2014; Theile et al., 2013) or aptamers (Janssen et al., 2013).

In one embodiment, to ensure proper staining of intracellular and cell surface proteins with, for instance, DNA-tagged antibodies, single cells are embedded in hydrogel droplets. Not being bound by a theory, the hydrogel mesh provides a physical framework, chemically incorporates biomolecules and is permeable to macromolecules such as antibodies (Chung et al., 2013). In one embodiment, to further improve permeability and staining efficiency, lipids are cleared (Chung et al., 2013). Not being bound by a theory, the clearance of the lipids and the porosity of the hydrogel allow for more efficient washing and removal of unspecific antibodies. This higher accuracy of measurement is important for the high multiplex measurements and computational inference of regulatory mechanisms.

In one embodiment, cells embedded in a hydrogel mesh can be stained with the DNA-tagged antibodies and washed in bulk before isolating the single cells. Once isolated, a cell specific oligonucleotide barcode (USI) can be introduced before subsequent DNA amplification and library preparation steps. Isolating single cells into individual reaction chambers to perform PCR amplification or a proximity ligation/extension assay (Assarsson et al., 2014) can be achieved at modest throughput either by FACS sorting into multi-well plates or microfluidic capture using the Fluidigm C1 (Shalek et al., 2014).

In one embodiment, for more high throughput processing, a microfluidic chip can be used to capture the hydrogel embedded cells or cellular constituents in nanoliter-sized aqueous droplets (Macosko et al., 2015, "Highly Parallel Genome-wide Expression Profiling of Individual Cells Using Nanoliter Droplets" Cell 161, 1202-1214). In one embodiment, the hydrogel embedded cells or cellular constituents are poisson loaded into microwells (Fan et al., 2015). The aqueous droplets or microwells may be simultaneously loaded with barcoded beads, each of which has oligonucleotides including; a "cell barcode" that is the same across all the primers on the surface of any one bead, but different from the cell barcodes on all other beads; a Unique Molecular Identifier (UMI), different on each primer, that enables sequence reads derived from the same original DNA tag (amplification and PCR duplicates) to be identified computationally (Kivioja et al., 2012); and a capture sequence to bind the oligos (either amplified PCR products or original DNA tags released by proteinase K treatment, or enzymatic/photonic oligo cleavage). Once the beads are loaded, they can be pooled for amplification and library preparation, and sequencing. These beads can take multiple forms, the preferred drop-seq beads are polystyrene, oligo functionalized beads, but alternative beads are possible, such as soft beads (polymer gel based beads), that allow for one on one pairing with cells, as to avoid the poisson loading needed in the described drop-seq scheme. This reduces the amount of cells one needs, and makes it possible to analyze rare cell types or clinical samples only available in low amounts of cells.

In one embodiment, the present invention provides for the simultaneous detection of proteins and nucleic acids. Nucleic acids can be reverse cross-linked after separation of discrete polymer matrices into separate wells or droplets. The contents of individual wells or droplets may then be sequenced. In one embodiment, crosslinking is reversed by incubating the cross-linked sample in high salt (approximately 200 mM NaCl) at 65° C. for at least 4 h.

In one embodiment, Drop-Seq (Macosko et al., 2015) is used to analyze RNA or DNA in single cells in parallel to the detection of cellular constituents. Drop-Seq is a reverse emulsion, early barcoding method for analyzing $10^4$-$10^6$ cells/experiment at very low cost ($0.06/cell). The Drop-seq method may be used to encapsulate discrete hydrogel matrices in a droplet. The RNA and/or DNA can be reverse cross-linked and the oligonucleotide labels can be removed from the labelling ligand. Capture of RNA, DNA, and oligonucleotide labels on barcoded beads, library preparation, and sequencing is performed as described previously.

In one embodiment, the detection of proteins or post translational modifications (PTM) is determined by sequencing based readouts. In some embodiments, Immuno-Seq is used when antibodies can be washed out (Niemeyer, C. M., et al., Nat Protoc. 2, 1918-1930 (2007)) and proximity extension assays (PEA) is used when antibodies cannot be washed away (Hammond, M., et al. PLoS One. 7, e40405, (2012); and Stahlberg, A., et al. Clin Chem. 58, 1682-1691 (2012)). These methods use DNA-sequence based encoding, and are compatible with other genomic readouts (e.g., sgRNA barcodes).

In another embodiment, the detection of proteins embedded in a hydrogel matrix is determined by FACS. Not being bound by a theory, the encapsulation of cellular constituents in a hydrogel matrix and removing lipids provides for improved binding of antibodies to intracellular targets as compared to regular fixation and permeabilization protocols for FACS alone.

In one embodiment, PEA methods are used for profiling protein-protein or protein-nucleic acid interactions by, respectively, using antibodies against two protein targets (Leuchowius, K. J., et al. Cytometry A. 75, 833-839 (2009)). or replacing one antibody with an oligonucleotide complementary to a sequence of interest (Gustafsdottir, S. M., et al. Proceedings of the National Academy of Sciences of the United States of America. 104, 3067-3072, (2007)).

In another aspect, the present invention provides screening methods to determine the effect on protein, post translational modifications and cellular constituents of single cells or isolated aggregations of cellular constituents in response to the perturbation of genes or cellular circuits. Perturbation may be knocking down a gene, increasing expression of a gene, mutating a gene, mutating a regulatory sequence, or deleting non-protein-coding DNA.

In one embodiment, CRISPR/Cas9 may be used to perturb protein-coding genes or non-protein-coding DNA. CRISPR/Cas9 may be used to knockout protein-coding genes by frameshifts, point mutations, inserts, or deletions. An extensive toolbox may be used for efficient and specific CRISPR/Cas9 mediated knockout as described herein, including a double-nicking CRISPR to efficiently modify both alleles of a target gene or multiple target loci and a smaller Cas9 protein for delivery on smaller vectors (Ran, F. A., et al., In vivo genome editing using *Staphylococcus aureus* Cas9. Nature. 520, 186-191 (2015)). A genome-wide sgRNA mouse library (10 sgRNAs/gene) may also be used in a mouse that expresses a Cas9 protein. The cells of the mouse can then be analyzed using the methods of the present invention.

In one embodiment, a CRISPR system may be used to activate gene transcription. A nuclease-dead RNA-guided DNA binding domain, dCas9, tethered to transcriptional repressor domains that promote epigenetic silencing (e.g., KRAB) may be used for "CRISPRi" that represses transcription. To use dCas9 as an activator (CRISPRa), a guide RNA is engineered to carry RNA binding motifs (e.g., MS2) that recruit effector domains fused to RNA-motif binding proteins, increasing transcription. A key dendritic cell molecule, p65, may be used as a signal amplifier, but is not required.

In one embodiment, perturbation is by deletion of regulatory elements. Noncoding elements may be targeted by using pairs of guide RNAs to delete regions of a defined size, and by tiling deletions covering sets of regions in pools.

In one embodiment, perturbation of genes is by RNAi. The RNAi may be shRNA's targeting genes. The shRNA's may be delivered by any methods known in the art. In one embodiment the shRNA's may be delivered by a viral vector. The viral vector may be a lentivirus.

In one embodiment, a CRISPR based pooled screen is used. Perturbation may rely on sgRNA expression cassettes that are stably integrated into the genome. The expressed sgRNA may serve as a molecular barcode, reporting the loss of function of the target in a cell. Alternatively, optimized separate barcodes may be co-expressed with the sgRNA, should sgRNAs not be ideal as barcodes. Transduction of cells at a higher multiplicity of infection (MOI) or delivering vectors by transfection at a higher MOI would result in any given cell receiving multiple sgRNA's and allow combinatorial perturbations. In one embodiment, 2, or 3, or 4, or 5, or up to 10 genes, preferably 5-7 genes are perturbed in a single cell. In certain example embodiments, a pooled CRISPR screen such as that disclosed in Datlinger et al. bioRxiv (2016) doi:http:/dx.doi.org.10.1101/083774 may be used in connection with the devices and methods disclosed herein.

In one embodiment, recombinant Cas9 protein and sgRNA is delivered simultaneously to cells with nanowires or the recently developed 'CellSqueeze' (Sharei, A., et al. Proceedings of the National Academy of Sciences of the United States of America. 110, 2082-2087, (2013)). Applicants have shown that nanowires can deliver functional proteins, RNA and small molecules alone and in combinations into the cell's cytoplasm, and do not cause toxicity or inappropriate activation and allow the cells to respond normally to signals (Shalek, A. K., et al. Nano Lett. 12, 6498-6504, (2012); Yosef, N., et al. Nature. 496, 461-468, (2013); and Shalek, A. K., et al. Proceedings of the National Academy of Sciences of the United States of America. 107, 1870-1875, (2010)).

In one embodiment, hybrid measurements or alternative readouts are measured. The alternative readouts may either be stand alone, or hybrid measurements. One alternative readout may be epigenetic measurements. Not being bound by a theory, when biomolecules with functional groups are formaldehyde fixed and bound to the polymer mesh, and membrane and nuclear lipids are cleared, chromosomal DNA is preserved and is accessible for further interrogation. Epigenetic assays that have been applied to single cells may be combined with a perturbation and protein level readout. Not being bound by a theory, the new layers of information aid in understanding of the regulatory mechanisms underpinning cellular behavior. Histone modifications have been measured at specific gene loci at the single cell level (Gomez et al., 2013). This publication uses ISH-PLA (in situ hybridization (ISH), proximity ligation assay (PLA)). They use a biotin modified ISH probe, by binding with streptavidin and an oligo bound anti-streptavidin antibody. As antibodies against multiple histone modifications are readily available, the PLA scheme is applicable to the present invention. Not being bound by a theory, a histone code based on the combination of a plurality of histone modifications determines gene expression at a given locus. Many histone modifications at many genetic loci can be determined simultaneously by replacing the biotin-streptavidin construct by an ISH probe conjugated to a linker (peptide, DNA or nanoparticles, . . . ), followed by another DNA barcode reporting on the genetic locus, and including a binding sequence to the oligo conjugated to the histone modification antibody.

In one embodiment, chromatin accessibility is determined using a single cell ATAC-seq assay. ATAC-seq offers genome-wide chromatin accessibility of regulatory elements, transcription factor binding and nucleosome positioning.

In one embodiment, DNA methylation analysis is determined. Cytosine methylation analysis has been analyzed at the single cell level (Kantlehner et al., 2011), as has adenine methylation (Lorthongpanich et al., 2013).

In one embodiment, the spatial organization of chromosomes is determined. The spatial organization of chromosomes has been found to have fundamental effects on gene expression and cellular function. Single cell measurements (Hi-C) have revealed extensive cell-to-cell heterogeneity in chromosome structure (Nagano et al., 2013). This method can be incorporated into the present invention.

In one embodiment, protein-protein interactions are measured. In addition to assessing presence and abundance of individual proteins, assays such as Proximity Extension Assay (PEA) allow for assaying the proximity of two proteins. In particular, the present invention allows for probing protein-protein interactions by designing pairs of antibodies for the interacting proteins of interest, such that the oligos conjugated to these antibodies have a binding region, which only bind when the two proteins are in near proximity, and therefore only PCR amplify in this case.

In one embodiment, protein-DNA interaction measurements are determined. Similar to the modified ISH-PLA described herein, instead of probing histone modifications, one could probe protein (transcription factor) proximity to many specific genetic loci, in a multiplex fashion.

In one embodiment, fluorescent in situ hybridization methods are used in the present invention. The present invention allows a combined approach where cells can be fluorescently labeled by methods known in the art, and cells of interest can be selected for downstream profiling of cellular constituents. In addition, the assays of the present invention can be combined with in situ hybridization methods such as RNA and DNA FISH.

In another embodiment, the gelled and cleared cells offer a platform in which any biological agent that is able to be detected by a high affinity and specific counterpart or ligand that can directly or indirectly be conjugated to a DNA molecule could be detected and quantified using the methods of the present invention.

Releasing the oligo's to be sequenced from their antibody can take a multitude of forms; i.e. in one embodiment, oligo's could be released from their antibodies by digesting all proteins (for instance proteinase K), alternatively, photocleavable linkers could be used, or restriction sites could be included in the oligo sequence to allow for enzymatic restriction and release. In another embodiment, the oligo can stay bound to the antibody, and in situ amplified (i.e. either by PCR, rolling circle amplification or T7 polymerase amplification) and the products of this reaction could be captured and sequenced.

Similarly, capturing the released oligo's could take a number of forms: in a drop based approach, beads can be loaded with capture oligo's as described herein. Microwells could either be loaded with beads, or their surface could be functionalized with capture oligos from which further amplification could take place. Alternatively, in the scenario where drops are sorted into multiwell plates, or microfluidic reaction chambers such as the Fluidigm C1 system, oligos can be amplified linearly or exponentially, and cellular barcodes and library adapters can be added on during these amplification steps.

Many different assays have been developed for oligo-barcode based detection of proteins (Janssen et al., 2013) and may be used in the present invention.

In one embodiment, cells are fixed and monomer infused before capturing them in a droplet. Alternatively, cells or aggregations of constituents are co-flowed with a lysis/monomer solution into a larger diameter drop. In this embodiment, biomolecules from a single cell or isolated aggregation of constituents are spread over a larger volume, which with similar polymer density could increase accessibility for staining.

With respect to general information on CRISPR-Cas Systems, components thereof, and delivery of such components, including methods, materials, delivery vehicles, vectors, particles, AAV, and making and using thereof, including as to amounts and formulations, all useful in the practice of the instant invention, reference is made to: U.S. Pat. Nos. 8,999,641, 8,993,233, 8,945,839, 8,932,814, 8,906,616, 8,895,308, 8,889,418, 8,889,356, 8,871,445, 8,865,406, 8,795,965, 8,771,945 and 8,697,359; US Patent Publications US 2014-0310830 (U.S. application Ser. No. 14/105,031), US 2014-0287938 A1 (U.S. application Ser. No. 14/213,991), US 2014-0273234 A1 (U.S. application Ser. No. 14/293,674), US2014-0273232 A1 (U.S. application Ser. No. 14/290,575), US 2014-0273231 (U.S. application Ser. No. 14/259,420), US 2014-0256046 A1 (U.S. application Ser. No. 14/226,274), US 2014-0248702 A1 (U.S. application Ser. No. 14/258,458), US 2014-0242700 A1 (U.S. application Ser. No. 14/222,930), US 2014-0242699 A1 (U.S. application Ser. No. 14/183,512), US 2014-0242664 A1 (U.S. application Ser. No. 14/104,990), US 2014-0234972 A1 (U.S. application Ser. No. 14/183,471), US 2014-0227787 A1 (U.S. application Ser. No. 14/256,912), US 2014-0189896 A1 (U.S. application Ser. No. 14/105,035), US 2014-0186958 (U.S. application Ser. No. 14/105,017), US 2014-0186919 A1 (U.S. application Ser. No. 14/104,977), US 2014-0186843 A1 (U.S. application Ser. No. 14/104,900), US 2014-0179770 A1 (U.S. application Ser. No. 14/104,837) and US 2014-0179006 A1 (U.S. application Ser. No. 14/183,486), US 2014-0170753 (U.S. application Ser. No. 14/183,429); European Patents EP 2 784 162 B1 and EP 2 771 468 B1; European Patent Applications EP 2 771 468 (EP13818570.7), EP 2 764 103 (EP13824232.6), and EP 2 784 162 (EP14170383.5); and PCT Patent Publications WO 2014/093661 (PCT/US2013/074743), WO 2014/093694 (PCT/US2013/074790), WO 2014/093595 (PCT/US2013/074611), WO 2014/093718 (PCT/US2013/074825), WO 2014/093709 (PCT/US2013/074812), WO 2014/093622 (PCT/US2013/074667), WO 2014/093635 (PCT/US2013/074691), WO 2014/093655 (PCT/US2013/074736), WO 2014/093712 (PCT/US2013/074819), WO2014/093701 (PCT/US2013/074800), WO2014/018423 (PCT/US2013/051418), WO 2014/204723 (PCT/US 2014/041790), WO 2014/204724 (PCT/US2014/041800), WO 2014/204725 (PCT/US 2014/041803), WO 2014/204726 (PCT/US2014/041804), WO 2014/204727 (PCT/US 2014/041806), WO 2014/204728 (PCT/US2014/041808), WO 2014/204729 (PCT/US2014/041809). Reference is also made to U.S. provisional patent applications 61/758,468; 61/802,174; 61/806,375; 61/814,263; 61/819,803 and 61/828,130, filed on Jan. 30, 2013; Mar. 15, 2013; Mar. 28, 2013; Apr. 20, 2013; May 6, 2013 and May 28, 2013 respectively. Reference is also made to U.S. provisional patent application 61/836,123, filed on Jun. 17, 2013. Reference is additionally made to U.S. provisional patent applications 61/835,931, 61/835,936, 61/836,127, 61/836,101, 61/836,080 and 61/835,973, each filed Jun. 17, 2013. Further reference is made to U.S. provisional patent applications 61/862,468 and 61/862,355 filed on Aug. 5, 2013; 61/871,301 filed on Aug. 28, 2013; 61/960,777 filed on Sep. 25, 2013 and 61/961,980 filed on Oct. 28, 2013. Reference is yet further made to: PCT Patent applications Nos: PCT/US2014/041803, PCT/US2014/041800, PCT/US2014/041809, PCT/US2014/041804 and PCT/US2014/041806, each filed Jun. 10, 2014 Jun. 10, 14; PCT/US2014/041808 filed Jun. 11, 2014; and PCT/US2014/62558 filed Oct. 28, 2014, and U.S. Provisional Patent Applications Ser. Nos. 61/915,150, 61/915,301, 61/915,267 and 61/915,260, each filed Dec. 12, 2013; 61/757,972 and 61/768,959, filed on Jan. 29, 2013 and Feb. 25, 2013; 61/835,936, 61/836,127, 61/836,101, 61/836,080, 61/835,973, and 61/835,931, filed Jun. 17, 2013; 62/010,888 and 62/010,879, both filed Jun. 11, 2014; 62/010,329 and 62/010,441, each filed Jun. 10, 2014; 61/939,228 and 61/939,242, each filed Feb. 12, 2014; 61/980,012, filed Apr. 15, 2014; 62/038,358, filed Aug. 17, 2014; 62/054,490, 62/055,484, 62/055,460 and 62/055,487, each filed Sep. 25, 2014; and 62/069,243, filed Oct. 27, 2014. Reference is also made to U.S. provisional patent applications Nos. 62/055,484, 62/055,460, and 62/055,487, filed Sep. 25, 2014; U.S. provisional patent application 61/980,012, filed Apr. 15, 2014; and U.S. provisional patent application 61/939,242 filed Feb. 12, 2014. Reference is made to PCT application designating, inter alia, the United States, application No. PCT/US14/41806, filed Jun. 10, 2014. Reference is made to U.S. provisional patent application 61/930,214 filed on Jan. 22, 2014. Reference is made to U.S. provisional patent applications 61/915,251; 61/915,260 and 61/915,267, each filed on Dec. 12, 2013. Reference is made to US provisional patent application U.S. Ser. No. 61/980,012 filed Apr. 15, 2014. Reference is made to PCT application designating, inter alia, the United States, application No. PCT/US14/41806, filed Jun. 10, 2014. Reference is made to U.S. provisional patent application 61/930,214 filed on Jan. 22, 2014. Reference is made to U.S. provisional patent applications 61/915,251; 61/915,260 and 61/915,267, each filed on Dec. 12, 2013.

Mention is also made of U.S. application 62/091,455, filed, 12 Dec. 14, PROTECTED GUIDE RNAS (PGRNAS); U.S. application 62/096,708, 24 Dec. 14, PROTECTED GUIDE RNAS (PGRNAS); U.S. application 62/091,462, 12 Dec. 14, DEAD GUIDES FOR CRISPR TRANSCRIPTION FACTORS; U.S. application 62/096,324, 23 Dec. 14, DEAD GUIDES FOR CRISPR TRANSCRIPTION FACTORS; U.S. application 62/091,456, 12 Dec. 14, ESCORTED AND FUNCTIONALIZED GUIDES FOR CRISPR-CAS SYSTEMS; U.S. application 62/091,461, 12 Dec. 14, DELIVERY, USE AND THERAPEUTIC APPLICATIONS OF THE CRISPR-CAS SYSTEMS AND COMPOSITIONS FOR GENOME EDITING AS TO HEMATOPOIETIC STEM CELLS (HSCs); U.S. application 62/094,903, 19 Dec. 14, UNBIASED IDENTIFICATION OF DOUBLE-STRAND BREAKS AND GENOMIC REARRANGEMENT BY GENOME-WISE INSERT CAPTURE SEQUENCING; U.S. application 62/096,761, 24 Dec. 14, ENGINEERING OF SYSTEMS, METHODS AND OPTIMIZED ENZYME AND GUIDE SCAFFOLDS FOR SEQUENCE MANIPULATION; U.S. application 62/098,059, 30 Dec. 14, RNA-TARGETING SYSTEM; U.S. application 62/096,656, 24 Dec. 14, CRISPR HAVING OR ASSOCIATED WITH DESTABILIZATION DOMAINS; U.S. application 62/096,697, 24 Dec. 14, CRISPR HAVING OR ASSOCIATED WITH AAV; U.S. application 62/098,158, 30 Dec. 14, ENGINEERED CRISPR COMPLEX INSERTIONAL TARGETING SYSTEMS; U.S. application 62/151,052, 22 Apr. 15, CELLULAR TARGETING FOR EXTRACELLULAR EXOSOMAL REPORTING; U.S. application 62/054,490, 24 Sep. 14, DELIVERY, USE AND THERAPEUTIC APPLICATIONS OF THE CRISPR-CAS SYSTEMS AND COMPOSITIONS FOR TARGETING DISORDERS AND DISEASES USING PARTICLE DELIVERY COMPONENTS; U.S. application 62/055,484, 25 Sep. 14, SYSTEMS, METHODS AND COMPOSITIONS FOR SEQUENCE MANIPULATION WITH OPTIMIZED FUNCTIONAL CRISPR-CAS SYSTEMS; U.S. application 62/087,537, 4 Dec. 14, SYSTEMS, METHODS AND COMPOSITIONS FOR SEQUENCE MANIPULATION WITH OPTIMIZED FUNCTIONAL CRISPR-CAS SYSTEMS; U.S. application 62/054,651, 24 Sep. 14, DELIVERY, USE AND THERAPEUTIC APPLICATIONS OF THE CRISPR-CAS SYSTEMS AND COMPOSITIONS FOR MODELING COMPETITION OF MULTIPLE CANCER MUTATIONS IN VIVO; U.S. application 62/067,886, 23 Oct. 14, DELIVERY, USE AND THERAPEUTIC APPLICATIONS OF THE CRISPR-CAS SYSTEMS AND COMPOSITIONS FOR MODELING COMPETITION OF MULTIPLE CANCER MUTATIONS IN VIVO; U.S. application 62/054,675, 24 Sep. 14, DELIVERY, USE AND THERAPEUTIC APPLICATIONS OF THE CRISPR-CAS SYSTEMS AND COMPOSITIONS IN NEURONAL CELLS/TISSUES; U.S. application 62/054,528, 24 Sep. 14, DELIVERY, USE AND THERAPEUTIC APPLICATIONS OF THE CRISPR-CAS SYSTEMS AND COMPOSITIONS IN IMMUNE DISEASES OR DISORDERS; U.S. application 62/055,454, 25 Sep. 14, DELIVERY, USE AND THERAPEUTIC APPLICATIONS OF THE CRISPR-CAS SYSTEMS AND COMPOSITIONS FOR TARGETING DISORDERS AND DISEASES USING CELL PENETRATION PEPTIDES (CPP); U.S. application 62/055,460, 25 Sep. 14, MULTIFUNCTIONAL-CRISPR COMPLEXES AND/OR OPTIMIZED ENZYME LINKED FUNCTIONAL-CRISPR COMPLEXES; U.S. application 62/087,475, 4 Dec. 14, FUNCTIONAL SCREENING WITH OPTIMIZED FUNCTIONAL CRISPR-CAS SYSTEMS; U.S. application 62/055,487, 25 Sep. 14, FUNCTIONAL SCREENING WITH OPTIMIZED FUNCTIONAL CRISPR-CAS SYSTEMS; U.S. application 62/087,546, 4 Dec. 14, MULTIFUNCTIONAL CRISPR COMPLEXES AND/OR OPTIMIZED ENZYME LINKED FUNCTIONAL-CRISPR COMPLEXES; and U.S. application 62/098,285, 30 Dec. 14, CRISPR MEDIATED IN VIVO MODELING AND GENETIC SCREENING OF TUMOR GROWTH AND METASTASIS.

Each of these patents, patent publications, and applications, and all documents cited therein or during their prosecution ("appln cited documents") and all documents cited or referenced in the appln cited documents, together with any instructions, descriptions, product specifications, and product sheets for any products mentioned therein or in any document therein and incorporated by reference herein, are hereby incorporated herein by reference, and may be employed in the practice of the invention. All documents (e.g., these patents, patent publications and applications and the appln cited documents) are incorporated herein by reference to the same extent as if each individual document was specifically and individually indicated to be incorporated by reference.

Also with respect to general information on CRISPR-Cas Systems, mention is made of the following (also hereby incorporated herein by reference):

Multiplex genome engineering using CRISPR/Cas systems. Cong, L., Ran, F. A., Cox, D., Lin, S., Barretto, R., Habib, N., Hsu, P. D., Wu, X., Jiang, W., Marraffini, L. A., & Zhang, F. Science February 15; 339(6121):819-23 (2013);

RNA-guided editing of bacterial genomes using CRISPR-Cas systems. Jiang W., Bikard D., Cox D., Zhang F, Marraffini L A. Nat Biotechnol March; 31(3):233-9 (2013);

One-Step Generation of Mice Carrying Mutations in Multiple Genes by CRISPR/Cas-Mediated Genome Engineering. Wang H., Yang H., Shivalila C S., Dawlaty M M., Cheng A W., Zhang F., Jaenisch R. Cell May 9; 153(4):910-8 (2013);

Optical control of mammalian endogenous transcription and epigenetic states. Konermann S, Brigham M D, Trevino A E, Hsu P D, Heidenreich M, Cong L, Platt R J, Scott D A, Church G M, Zhang F. Nature. August 22; 500(7463):472-6. doi: 10.1038/Nature12466. Epub 2013 August 23 (2013);

Double Nicking by RNA-Guided CRISPR Cas9 for Enhanced Genome Editing Specificity. Ran, F A., Hsu, P D., Lin, C Y., Gootenberg, J S., Konermann, S., Trevino, A E., Scott, D A., Inoue, A., Matoba, S., Zhang, Y., & Zhang, F. Cell August 28. pii: S0092-8674(13)01015-5 (2013-A);

DNA targeting specificity of RNA-guided Cas9 nucleases. Hsu, P., Scott, D., Weinstein, J., Ran, F A., Konermann, S., Agarwala, V., Li, Y., Fine, E., Wu, X., Shalem, O., Cradick, T J., Marraffini, L A., Bao, G., & Zhang, F. Nat Biotechnol doi:10.1038/nbt.2647 (2013);

Genome engineering using the CRISPR-Cas9 system. Ran, F A., Hsu, P D., Wright, J., Agarwala, V., Scott, D A., Zhang, F. Nature Protocols November; 8(11):2281-308 (2013-B);

Genome-Scale CRISPR-Cas9 Knockout Screening in Human Cells. Shalem, O., Sanjana, N E., Hartenian, E., Shi, X., Scott, D A., Mikkelson, T., Heckl, D., Ebert, B L., Root, D E., Doench, J G., Zhang, F. Science December 12. (2013). [Epub ahead of print];

Crystal structure of cas9 in complex with guide RNA and target DNA. Nishimasu, H., Ran, F A., Hsu, P D., Konermann, S., Shehata, S I., Dohmae, N., Ishitani, R., Zhang, F., Nureki, O. Cell February 27, 156(5):935-49 (2014);

Genome-wide binding of the CRISPR endonuclease Cas9 in mammalian cells. Wu X., Scott D A., Kriz A J., Chiu A C., Hsu P D., Dadon D B., Cheng A W., Trevino A E., Konermann S., Chen S., Jaenisch R., Zhang F., Sharp P A. Nat Biotechnol. April 20. doi: 10.1038/nbt.2889 (2014);

CRISPR-Cas9 Knockin Mice for Genome Editing and Cancer Modeling. Platt R J, Chen S, Zhou Y, Yim M J, Swiech L, Kempton H R, Dahlman J E, Parnas O, Eisenhaure T M, Jovanovic M, Graham D B, Jhunjhunwala S, Heidenreich M, Xavier R J, Langer R, Anderson D G, Hacohen N, Regev A, Feng G, Sharp P A, Zhang F. Cell 159(2):440-455 DOI: 10.1016/j.cell.2014.09.014(2014);

Development and Applications of CRISPR-Cas9 for Genome Engineering, Hsu P D, Lander E S, Zhang F., Cell. June 5; 157(6):1262-78 (2014);

Genetic screens in human cells using the CRISPR/Cas9 system, Wang T, Wei J J, Sabatini D M, Lander E S., Science. January 3; 343(6166): 80-84. doi:10.1126/science.1246981 (2014);

Rational design of highly active sgRNAs for CRISPR-Cas9-mediated gene inactivation, Doench J G, Hartenian E, Graham D B, Tothova Z, Hegde M, Smith I, Sullender M, Ebert B L, Xavier R J, Root D E., (published online 3 Sep. 2014) Nat Biotechnol. December; 32(12):1262-7 (2014);

In vivo interrogation of gene function in the mammalian brain using CRISPR-Cas9, Swiech L, Heidenreich M, Banerjee A, Habib N, Li Y, Trombetta J, Sur M, Zhang F., (published online 19 Oct. 2014) Nat Biotechnol. January; 33(1):102-6 (2015);

Genome-scale transcriptional activation by an engineered CRISPR-Cas9 complex, Konermann S, Brigham M D, Trevino A E, Joung J, Abudayyeh O O, Barcena C, Hsu P D, Habib N, Gootenberg J S, Nishimasu H, Nureki O, Zhang F., Nature. January 29; 517(7536):583-8 (2015);

A split-Cas9 architecture for inducible genome editing and transcription modulation, Zetsche B, Volz S E, Zhang F., (published online 2 Feb. 2015) Nat Biotechnol. February; 33(2):139-42 (2015);

Genome-wide CRISPR Screen in a Mouse Model of Tumor Growth and Metastasis, Chen S, Sanjana N E, Zheng K, Shalem O, Lee K, Shi X, Scott D A, Song J, Pan J Q, Weissleder R, Lee H, Zhang F, Sharp P A. Cell 160, 1246-1260, Mar. 12, 2015 (multiplex screen in mouse), and In vivo genome editing using *Staphylococcus aureus* Cas9, Ran F A, Cong L, Yan W X, Scott D A, Gootenberg J S, Kriz A J, Zetsche B, Shalem O, Wu X, Makarova K S, Koonin E V, Sharp P A, Zhang F., (published online 1 Apr. 2015), Nature. April 9; 520(7546): 186-91 (2015).

each of which is incorporated herein by reference, may be considered in the practice of the instant invention, and discussed briefly below:

Cong et al. engineered type II CRISPR-Cas systems for use in eukaryotic cells based on both *Streptococcus thermophilus* Cas9 and also *Streptococcus pyogenes* Cas9 and demonstrated that Cas9 nucleases can be directed by short RNAs to induce precise cleavage of DNA in human and mouse cells. Their study further showed that Cas9 as converted into a nicking enzyme can be used to facilitate homology-directed repair in eukaryotic cells with minimal mutagenic activity. Additionally, their study demonstrated that multiple guide sequences can be encoded into a single CRISPR array to enable simultaneous editing of several at endogenous genomic loci sites within the mammalian genome, demonstrating easy programmability and wide applicability of the RNA-guided nuclease technology. This ability to use RNA to program sequence specific DNA cleavage in cells defined a new class of genome engineering tools. These studies further showed that other CRISPR loci are likely to be transplantable into mammalian cells and can also mediate mammalian genome cleavage. Importantly, it can be envisaged that several aspects of the CRISPR-Cas system can be further improved to increase its efficiency and versatility.

Jiang et al. used the clustered, regularly interspaced, short palindromic repeats (CRISPR)-associated Cas9 endonuclease complexed with dual-RNAs to introduce precise mutations in the genomes of *Streptococcus pneumoniae* and *Escherichia coli*. The approach relied on dual-RNA:Cas9-directed cleavage at the targeted genomic site to kill unmutated cells and circumvents the need for selectable markers or counter-selection systems. The study reported reprogramming dual-RNA:Cas9 specificity by changing the sequence of short CRISPR RNA (crRNA) to make single- and multinucleotide changes carried on editing templates. The study showed that simultaneous use of two crRNAs enabled multiplex mutagenesis. Furthermore, when the approach was used in combination with recombineering, in *S. pneumoniae*, nearly 100% of cells that were recovered using the described approach contained the desired mutation, and in *E. coli*, 65% that were recovered contained the mutation.

Wang et al. (2013) used the CRISPR/Cas system for the one-step generation of mice carrying mutations in multiple genes which were traditionally generated in multiple steps by sequential recombination in embryonic stem cells and/or time-consuming intercrossing of mice with a single mutation. The CRISPR/Cas system will greatly accelerate the in vivo study of functionally redundant genes and of epistatic gene interactions.

Konermann et al. (2013) addressed the need in the art for versatile and robust technologies that enable optical and chemical modulation of DNA-binding domains based CRISPR Cas9 enzyme and also Transcriptional Activator Like Effectors.

Ran et al. (2013-A) described an approach that combined a Cas9 nickase mutant with paired guide RNAs to introduce targeted double-strand breaks. This addresses the issue of the Cas9 nuclease from the microbial CRISPR-Cas system being targeted to specific genomic loci by a guide sequence, which can tolerate certain mismatches to the DNA target and thereby promote undesired off-target mutagenesis. Because individual nicks in the genome are repaired with high fidelity, simultaneous nicking via appropriately offset guide RNAs is required for double-stranded breaks and extends the number of specifically recognized bases for target cleavage. The authors demonstrated that using paired nicking can reduce off-target activity by 50- to 1,500-fold in cell lines and to facilitate gene knockout in mouse zygotes without sacrificing on-target cleavage efficiency. This versatile strategy enables a wide variety of genome editing applications that require high specificity.

Hsu et al. (2013) characterized SpCas9 targeting specificity in human cells to inform the selection of target sites and avoid off-target effects. The study evaluated >700 guide RNA variants and SpCas9-induced indel mutation levels at >100 predicted genomic off-target loci in 293T and 293FT cells. The authors that SpCas9 tolerates mismatches between guide RNA and target DNA at different positions in a sequence-dependent manner, sensitive to the number, position and distribution of mismatches. The authors further showed that SpCas9-mediated cleavage is unaffected by DNA methylation and that the dosage of SpCas9 and sgRNA can be titrated to minimize off-target modification. Additionally, to facilitate mammalian genome engineering applications, the authors reported providing a web-based software tool to guide the selection and validation of target sequences as well as off-target analyses.

Ran et al. (2013-B) described a set of tools for Cas9-mediated genome editing via non-homologous end joining (NHEJ) or homology-directed repair (HDR) in mammalian cells, as well as generation of modified cell lines for downstream functional studies. To minimize off-target cleavage, the authors further described a double-nicking strategy using the Cas9 nickase mutant with paired guide RNAs. The protocol provided by the authors experimentally derived guidelines for the selection of target sites, evaluation of cleavage efficiency and analysis of off-target activity. The studies showed that beginning with target design, gene modifications can be achieved within as little as 1-2 weeks, and modified clonal cell lines can be derived within 2-3 weeks.

Shalem et al. described a new way to interrogate gene function on a genome-wide scale. Their studies showed that delivery of a genome-scale CRISPR-Cas9 knockout (GeCKO) library targeted 18,080 genes with 64,751 unique guide sequences enabled both negative and positive selection screening in human cells. First, the authors showed use of the GeCKO library to identify genes essential for cell viability in cancer and pluripotent stem cells. Next, in a melanoma model, the authors screened for genes whose loss is involved in resistance to vemurafenib, a therapeutic that inhibits mutant protein kinase BRAF. Their studies showed that the highest-ranking candidates included previously validated genes NF1 and MED12 as well as novel hits NF2, CUL3, TADA2B, and TADA1. The authors observed a high level of consistency between independent guide RNAs targeting the same gene and a high rate of hit confirmation, and thus demonstrated the promise of genome-scale screening with Cas9.

Nishimasu et al. reported the crystal structure of *Streptococcus pyogenes* Cas9 in complex with sgRNA and its target DNA at 2.5 A° resolution. The structure revealed a bilobed architecture composed of target recognition and nuclease lobes, accommodating the sgRNA:DNA heteroduplex in a positively charged groove at their interface. Whereas the recognition lobe is essential for binding sgRNA and DNA, the nuclease lobe contains the HNH and RuvC nuclease domains, which are properly positioned for cleavage of the complementary and non-complementary strands of the target DNA, respectively. The nuclease lobe also contains a carboxyl-terminal domain responsible for the interaction with the protospacer adjacent motif (PAM). This high-resolution structure and accompanying functional analyses have revealed the molecular mechanism of RNA-guided DNA targeting by Cas9, thus paving the way for the rational design of new, versatile genome-editing technologies.

Wu et al. mapped genome-wide binding sites of a catalytically inactive Cas9 (dCas9) from *Streptococcus pyogenes* loaded with single guide RNAs (sgRNAs) in mouse embryonic stem cells (mESCs). The authors showed that each of the four sgRNAs tested targets dCas9 to between tens and thousands of genomic sites, frequently characterized by a 5-nucleotide seed region in the sgRNA and an NGG protospacer adjacent motif (PAM). Chromatin inaccessibility decreases dCas9 binding to other sites with matching seed sequences; thus 70% of off-target sites are associated with genes. The authors showed that targeted sequencing of 295 dCas9 binding sites in mESCs transfected with catalytically active Cas9 identified only one site mutated above background levels. The authors proposed a two-state model for Cas9 binding and cleavage, in which a seed match triggers binding but extensive pairing with target DNA is required for cleavage.

Platt et al. established a Cre-dependent Cas9 knockin mouse. The authors demonstrated in vivo as well as ex vivo genome editing using adeno-associated virus (AAV)-, lentivirus-, or particle-mediated delivery of guide RNA in neurons, immune cells, and endothelial cells.

Hsu et al. (2014) is a review article that discusses generally CRISPR-Cas9 history from yogurt to genome editing, including genetic screening of cells.

Wang et al. (2014) relates to a pooled, loss-of-function genetic screening approach suitable for both positive and negative selection that uses a genome-scale lentiviral single guide RNA (sgRNA) library.

Doench et al. created a pool of sgRNAs, tiling across all possible target sites of a panel of six endogenous mouse and three endogenous human genes and quantitatively assessed their ability to produce null alleles of their target gene by antibody staining and flow cytometry. The authors showed that optimization of the PAM improved activity and also provided an on-line tool for designing sgRNAs.

Swiech et al. demonstrate that AAV-mediated SpCas9 genome editing can enable reverse genetic studies of gene function in the brain.

Konermann et al. (2015) discusses the ability to attach multiple effector domains, e.g., transcriptional activator, functional and epigenomic regulators at appropriate positions on the guide such as stem or tetraloop with and without linkers.

Zetsche et al. demonstrates that the Cas9 enzyme can be split into two and hence the assembly of Cas9 for activation can be controlled.

Chen et al. relates to multiplex screening by demonstrating that a genome-wide in vivo CRISPR-Cas9 screen in mice reveals genes regulating lung metastasis.

Ran et al. (2015) relates to SaCas9 and its ability to edit genomes and demonstrates that one cannot extrapolate from biochemical assays.

Also, "Dimeric CRISPR RNA-guided FokI nucleases for highly specific genome editing", Shengdar Q. Tsai, Nicolas Wyvekens, Cyd Khayter, Jennifer A. Foden, Vishal Thapar, Deepak Reyon, Mathew J. Goodwin, Martin J. Aryee, J. Keith Joung Nature Biotechnology 32(6): 569-77 (2014), relates to dimeric RNA-guided FokI Nucleases that recognize extended sequences and can edit endogenous genes with high efficiencies in human cells.

Useful in the practice of the instant invention, reference is made to the article entitled BCL11A enhancer dissection by Cas9-mediated in situ saturating mutagenesis. Canver, M. C., Smith, E. C., Sher, F., Pinello, L., Sanjana, N. E., Shalem, O., Chen, D. D., Schupp, P. G., Vinjamur, D. S., Garcia, S. P., Luc, S., Kurita, R., Nakamura, Y., Fujiwara, Y., Maeda, T., Yuan, G., Zhang, F., Orkin, S. H., & Bauer, D. E. DOI:10.1038/nature15521, published online Sep. 16, 2015, the article is herein incorporated by reference and discussed briefly below:

> Canver et al. describes novel pooled CRISPR-Cas9 guide RNA libraries to perform in situ saturating mutagenesis of the human and mouse BCL11A erythroid enhancers previously identified as an enhancer associated with fetal hemoglobin (HbF) level and whose mouse ortholog is necessary for erythroid BCL11A expression. This approach revealed critical minimal features and discrete vulnerabilities of these enhancers. Through editing of primary human progenitors and mouse transgenesis, the authors validated the BCL11A erythroid enhancer as a target for HbF reinduction. The authors generated a detailed enhancer map that informs therapeutic genome editing.

The present invention also provides for cell handling before hydrogel polymerization. In one embodiment, cells are fixed and infused with polymer monomers in bulk. Cells may then be segregated and polymerization initiated. Segregation can be by any means described herein. In preferred embodiments, segregation is performed by making single cell drops.

In another embodiment, biochemical, thermal, or optical treatment on chip of individual cells in reverse emulsion droplets is performed. In this embodiment, polymer monomers may be spiked in microfluidically and optionally fixation reagents. Polymerization of the monomers may then be performed. This allows biochemical, thermal, or optical treatments at the single-cell level. Examples include, but are not limited to: lysis, DNA/RNA fragmentation/tagmentation, dosing with drugs, enzymatic reactions, or any perturbation of the sample before fixation and/or anchoring biomolecules to the polymer mesh upon polymerization.

In one embodiment, the oligonucleotide label may comprise Iso-deoxyguanosine (iso-dG) and 5-methyl iso-dC (iso-dC). Iso-deoxyguanosine forms a Watson-Crick base pair with 5-methyl iso-dC, but has a different type of hydrogen bonding pattern than those observed for the natural base pairs A:T and C:G. Substitution of a iso-dG: 5-Me-iso-dC base pair for a C: G pair increases the Tm of the resulting duplex by ~2 deg C. per base pair substitution (Switzer, C., et al., Enzymatic incorporation of a new base pair into DNA and RNA. J. Am Chem. Soc. (1989), 111: 8322-8323; and Horn, T., et al., Hybridization properties of the 5-methyl-isocytidine/isoguanosine base pair in synthetic oligodeoxynucleotides. Tetrahedron Lett. (1995), 36: 2033-2036). Furthermore, since iso-dG does not pair with dC, iso-dG: 5-Me-iso-dC can function as a stable unnatural base pair that can be used to expand the genetic code. The combination of iso-dG's high selectivity for 5-Me-iso-dC, and the resulting base pair's high thermodynamic stability, make this modified base particular attractive in embodiments of the present invention.

In one embodiment, iso-dG:5-Me-iso-dC base pairing is used for molecular recognition. The 5-Me-iso-dC:iso-dG base pair may be incorporated into hybridization assays to enhance probe-target specificity and reduce spurious hybridization to non-target sequences. For example, Collins and co-workers significantly improved the sensitivity of a branched DNA quantitative hybridization assay for detecting the HIV POL sequence by incorporating ~30% 5-Me-iso-dC and iso-dG into the pre-amplifier, branched DNA (bDNA) amplifier and alkaline phosphate probe sequences used in the assay (Collins, M. L, et al. A branched DNA signal amplification assay for quantification of nucleic acid targets below 100 molecules/ml. Nucleic Acids Res. (1997), 25: 2979-2984). Use of this strategy resulted in a significant reduction in non-specific hybridization of the above three sequence types to non-target nucleic acid sequences, and thus less amplification of background. The limits of detection of the assay were improved 10-fold, from <500 HIV molecules/mL to <50 molecules/mL. In preferred embodiments, the present invention utilizes the 5-Me-iso-dC:iso-dG base pair to ensure the correct sequences base pair during hybridization of ligation handle primers and during hybridization of two oligonucleotide labels in proximity assays.

In another embodiment, iso-dG:5-Me-iso-dC base pairing is used for qPCR and artificially expanded genetic systems. A number of research groups have been working on optimizing PCR amplification on templates containing 5-Me-iso-dC. Such optimization is necessary to enable the full development of artificially expanded genetic systems utilizing an expanded genetic code, thereby allowing for the site-specific incorporation of novel functional components (such as unnatural amino acids) into proteins. In 2004, Johnson and co-workers observed that, by using the Klenow fragment of Taq polymerase (KF-Taq) in PCR, the fidelity of the 5-Me-iso-dC:iso-dG base pair was about 96% per amplification cycle (Johnson, S. C., et al., A third base pair for the polymerase chain reaction: inserting isoC and isoG. Nucleic Acids Resl. (2004), 32: 1937-1941). The limit in fidelity is chiefly due to the ability of iso-dG's 1,2 tautomer to mis-pair with dT. More recently, Sismour and Benner solved this problem by using 2-thio-dT (dT*) in place of dT. dT*pairs with dA, but not with iso-dG (Sismour, A. M.; Benner, S. A. The use of thymidine analogs to improve the replication of an extra DNA base pair: a synthetic biological system. Nucleic Acids Resl. (2005), 33: 5640-5646). Using this artificial base pair system (5-Me-iso-dC:iso-dG, dA:dT*, dC:dG) with KF-Taq, the fidelity in PCR was increased to about 98% per amplification cycle.

The practice of the present invention employs, unless otherwise indicated, conventional techniques of immunology, biochemistry, chemistry, molecular biology, microbiology, cell biology, genomics and recombinant DNA, which are within the skill of the art. See Sambrook, Fritsch and Maniatis, MOLECULAR CLONING: A LABORATORY MANUAL, 2nd edition (1989); CURRENT PROTOCOLS IN MOLECULAR BIOLOGY (F. M. Ausubel, et al. eds., (1987)); the series METHODS IN ENZYMOLOGY (Academic Press, Inc.): PCR 2: A PRACTICAL APPROACH (M. J. MacPherson, B. D. Hames and G. R. Taylor eds. (1995)), Harlow and Lane, eds. (1988) ANTIBODIES, A LABORATORY MANUAL, and ANIMAL CELL CULTURE (R. I. Freshney, ed. (1987)).

The practice of the present invention employs, unless otherwise indicated, conventional techniques for generation of genetically modified mice. See Marten H. Hofker and Jan van Deursen, TRANSGENIC MOUSE METHODS AND PROTOCOLS, 2nd edition (2011).

The present invention also provides methods applicable to the study of bulk cells and is not limited to single cells. Moreover, the assays described herein are also amenable to regularly fixed and permeabilized cells (i.e. not using polymerization). The proximity assays described herein may be performed on cells without generating discrete polymer matrices. Additionally, detection of cellular constituents utilizing labeling ligands and a sequencing readout may be used to detect low abundant cellular constituents. Not being bound by a theory, the oligonucleotide label may be amplified and increase the signal as compared to antibody readouts known in the art. Moreover, determination of proteins in relation to open chromatin need not be performed in a polymer matrix.

The present invention provides advantages over prior assays for detecting proteins and post translation modifications (PTM) in single cells or isolated aggregations of cellular constituents. Standard flow cytometry can be used to detect a few proteins/PTMs in greater than $10^6$ single cells; and CyTOF (heavy metal labeling with multiplex barcoding) can be used to detect ~30-50 proteins/PTMs in $10^5$-$10^6$ single cells. The present invention provides highly multiplexed, DNA sequencing-based readouts of protein/PTM levels of greater than 100's of proteins/PTMs in greater than $10^6$ cells.

The present invention advantageously provides a Massively Combinatorial Perturbation Profiling (MCPP) approach. Applicants can perturb vast numbers of combinations of genes, each targeting many circuit components at once. Applicants can use massively-parallel single cell genomics to measure genomic profiles and single cell proteomics to measure protein profiles after each perturbation. Applicants can infer the individual and combinatorial effects at each order, relying on random matrix theory, compressive sensing and kernel learning.

Biological systems are not linear: the combined effect of multiple factors is not simply the sum of their individual effects. This is a direct outcome of the biochemistry underlying molecular biology, from allosteric protein changes to cooperative binding, and is essential for cells to process complex signals. However, it has remained an insurmountable stumbling block to achieving a quantitative and predictive understanding of circuits on a genomic scale, with far-reaching implications for basic and translational science. Thus, the present invention provides a powerful combination by being able to measure transcriptional chromatin, epigenetic and proteomic changes as a function of genetic perturbation at the single cell level.

Combinatorial perturbation analyses have measured important genetic interactions, mainly from growth phenotypes in yeast. Mammalian studies have used ricin susceptibility and cell count phenotypes, but none combined large-scale, combinatorial genetic manipulation with complex, quantitative phenotypes, such as proteomic profiles. The single cell resolution readout of both response and perturbation, across many cells, serves as an improved starting point to unravel the function and interaction of the perturbed genes.

Although the present invention and its advantages have been described in detail, it should be understood that various changes, substitutions and alterations can be made herein without departing from the spirit and scope of the invention as defined in the appended claims.

The invention is further described in the following examples, which do not limit the scope of the invention described in the claims.

EXAMPLES

Example 1

Embodiments of Single-Cell Drop-Seq for Next Generation Sequencing Multiplex Protein Quantification FIG. 1 shows in step 1 an embodiment where single cells are isolated in droplets that are monomer infused using an aqueous solution in oil emulsion. Step 2 shows the polymerization of the infused monomers to generate a polymer matrix containing a single cell. Step 3 shows the extraction of lipids from the polymer matrix by treatment with SDS. Step 4 shows the binding of antibodies to cellular constituents and the washing out of unbound antibodies. Each antibody specific for a cellular constituent is bound by an oligo that serves as the UCI. Step 5A shows a low-throughput readout that includes the use of FACS to sort the hydrogel drops into a 384 well plate. The oligos are optionally amplified by a proximity extension assay, PCR, or rolling circle amplification. A NGS library is prepared for each well and the samples are sequenced. Step 5B shows a high-throughput readout that includes a restriction site or photocleavable linker or no cleavage site between the antibody and oligo. A second sequence includes a protein specific barcode (UCI), an UMI, and an universal sequence for bead capture. Step 6 shows one embodiment where a bead functionalized with an oligo barcode (USI) and a capturing universal sequence are encapsulated with the discrete polymer matrix in a second droplet containing an enzyme for cleaving the oligo from the antibody. Step 7 shows release of the oligo bound to the antibody and subsequent capture on the barcoded bead. Step 8 shows pooling of beads from multiple discrete polymer matrices, library prep, and sequencing.

Example 2

Single Cells are Microfluidically Embedded in Hydrogel Droplets

Figure 2A:
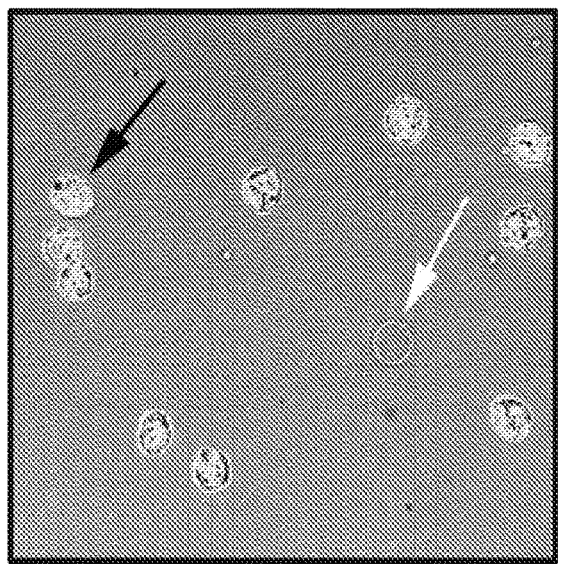
FIGS. 2A-2C illustrates a proof of principle.
Figure 2B:
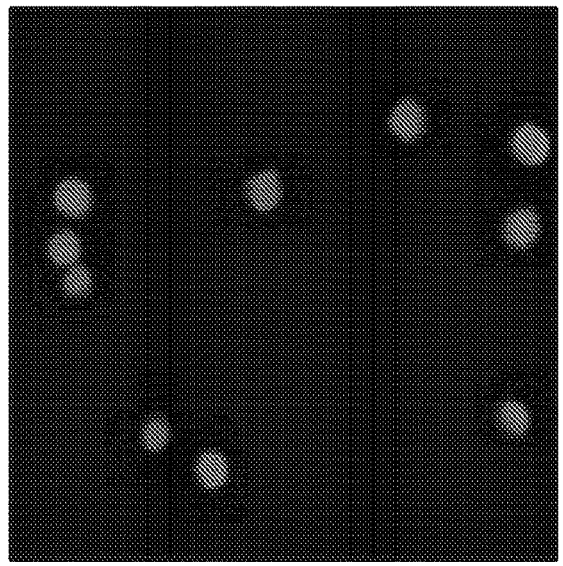
Figure 2C:
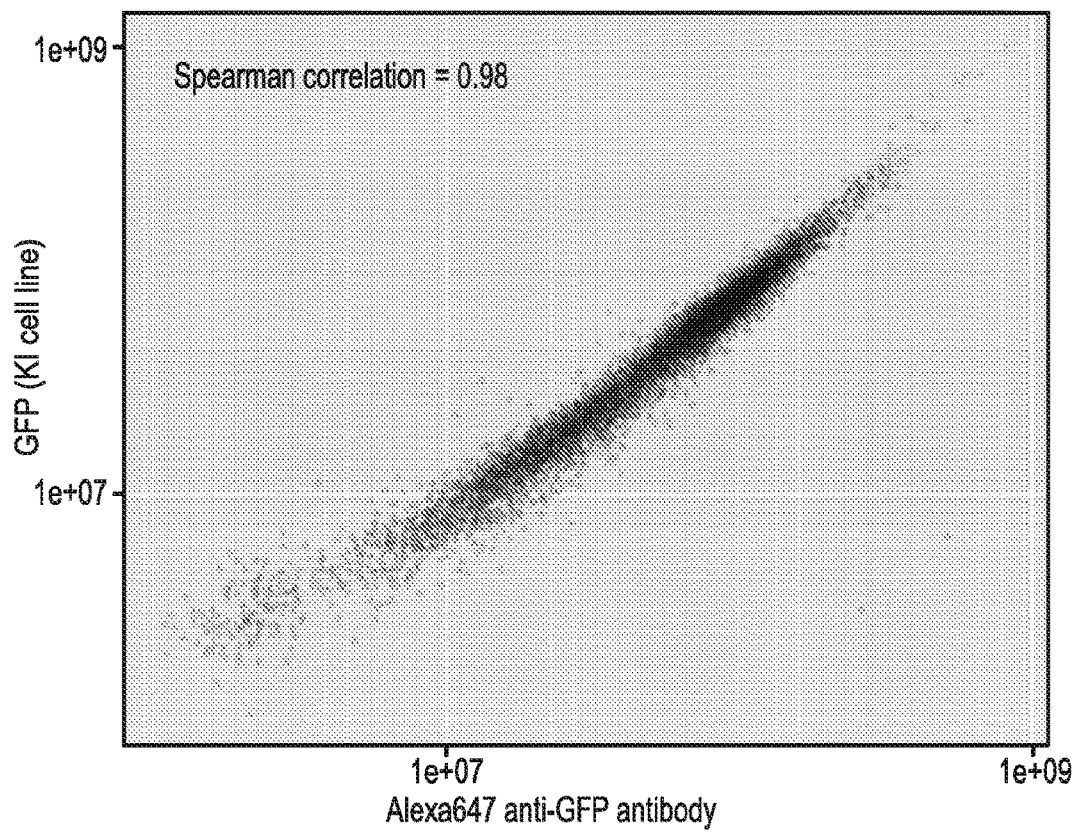
Figure 3:
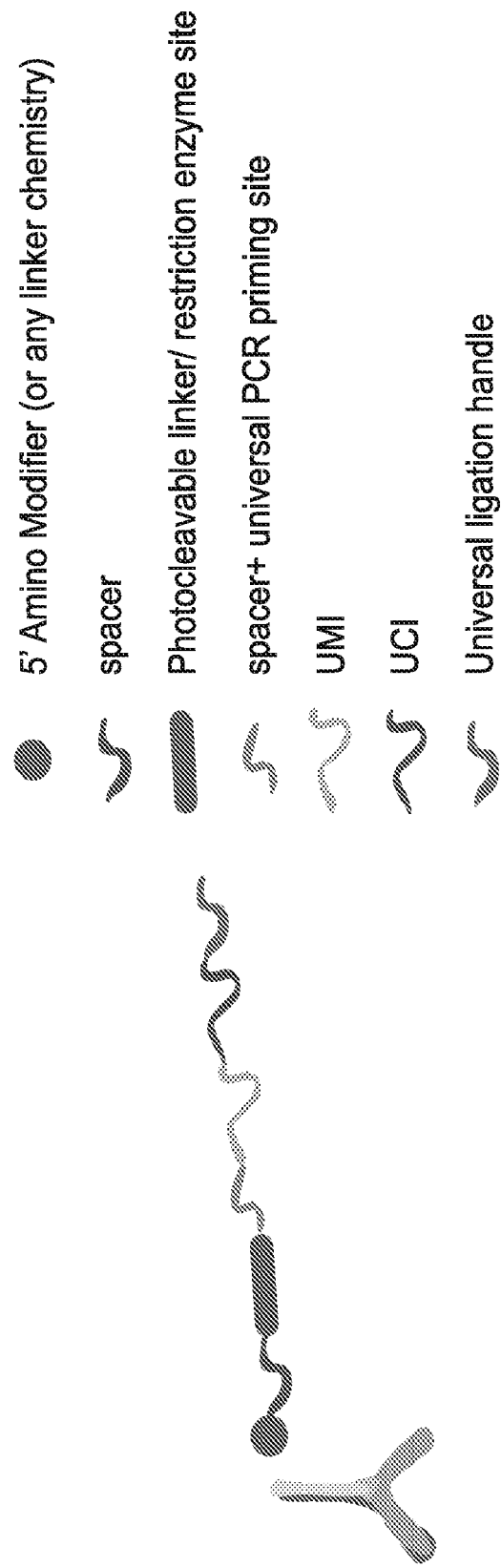
FIG. 3 illustrates measuring protein levels by staining of aggregations of cellular constituents with high affinity reagents (antibodies) linked to an oligonucleotide with the structure [5' Amino Modifier]-[~6 bp spacer]-[PhotoCleavable linker]-[~4 bp spacer]-[Illumina PCR primer]-[~8-16 bp UMI]-[~21 bp UCI]-[~20 bp universal ligation handle]. Note: UMI may be omitted in case of incorporation of a UMI in a split and pool index.
Figure 4:
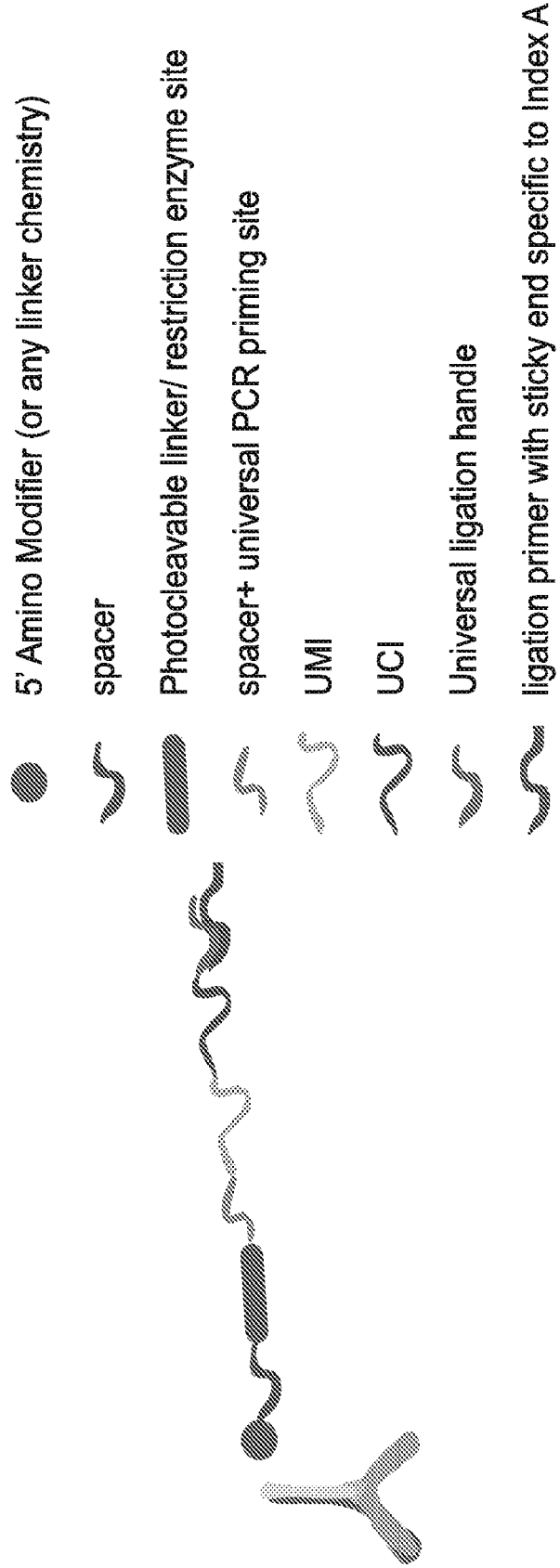
FIG. 4 illustrates hybridization of a ligation primer that binds to the universal ligation handle on oligonucleotide label, such that the sticky end needed for ligation of index A is produced.
Figure 5:
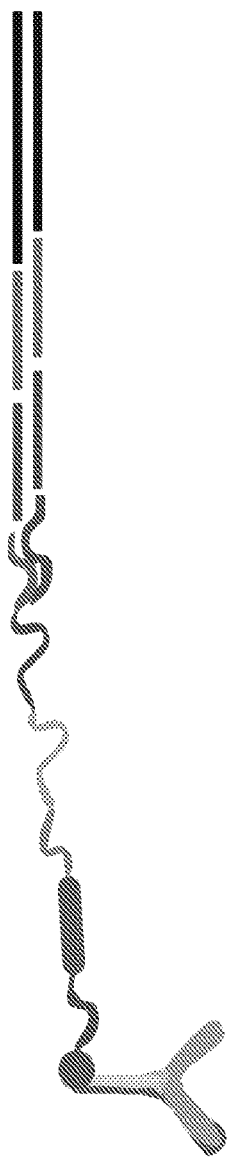
FIG. 5 illustrates split-pool ligation using single-cell hydrogel drops as the basic unit and ligation of Index A, B and [C+PCR primer].
Figure 6:
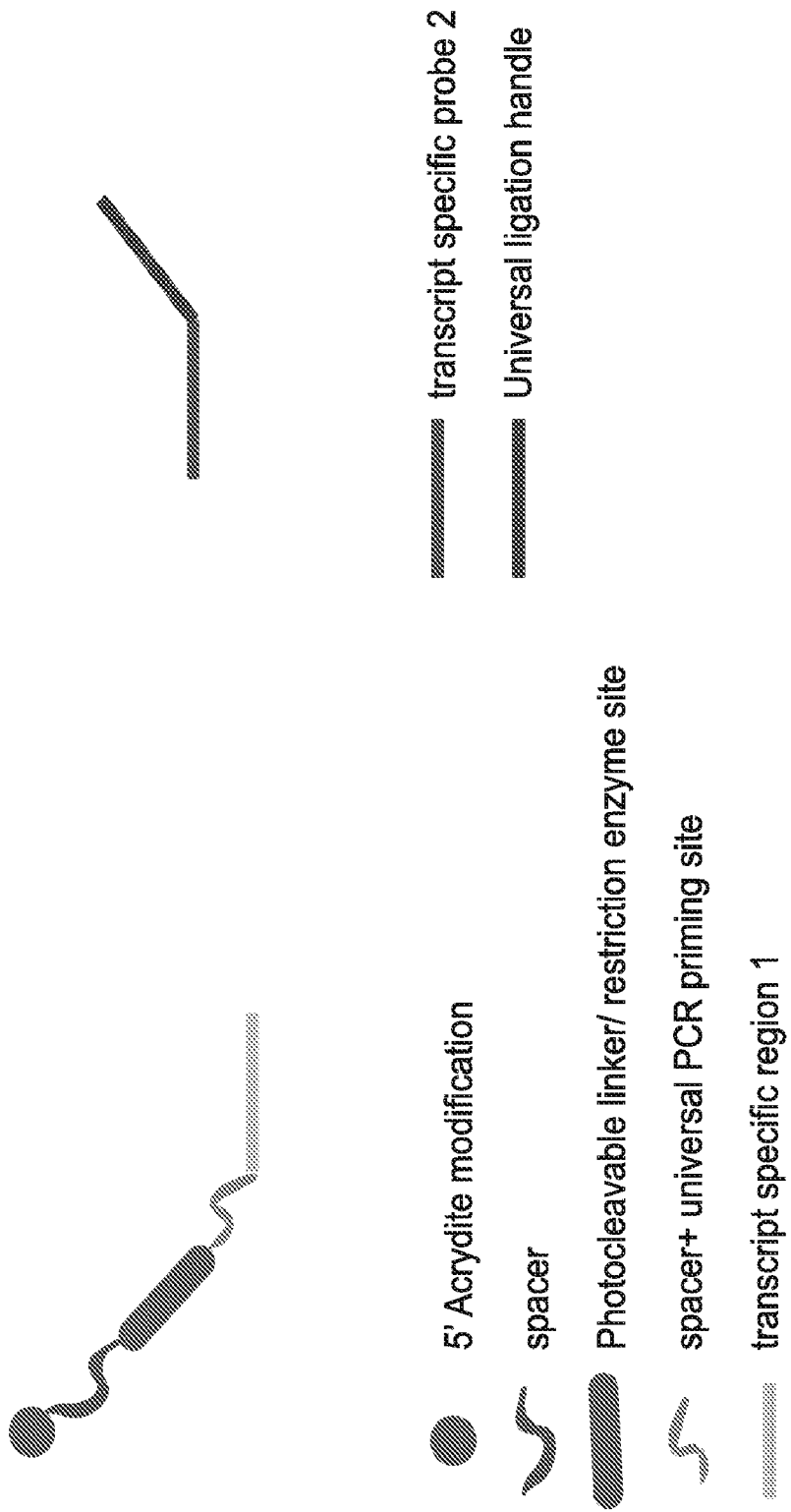
FIG. 6 illustrates staining in bulk with adjacent oligo's that hybridize to an RNA transcript or single guide RNA (sgRNA) at sites adjacent to each other.
Figure 7:
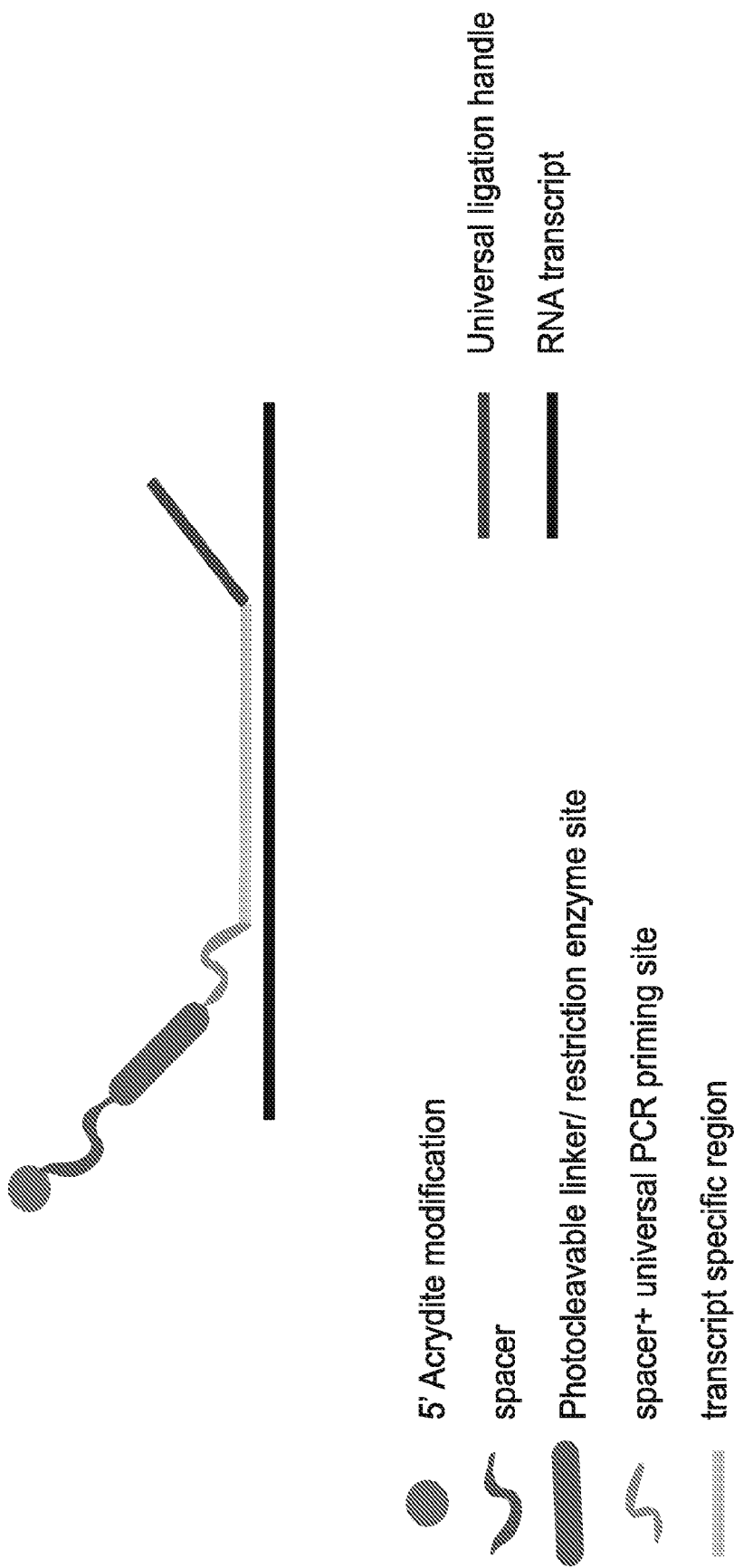
FIG. 7 illustrates single probe detection of an RNA transcript or sgRNA using a single DNA probe that specifically binds to the target transcript.
Figure 8:
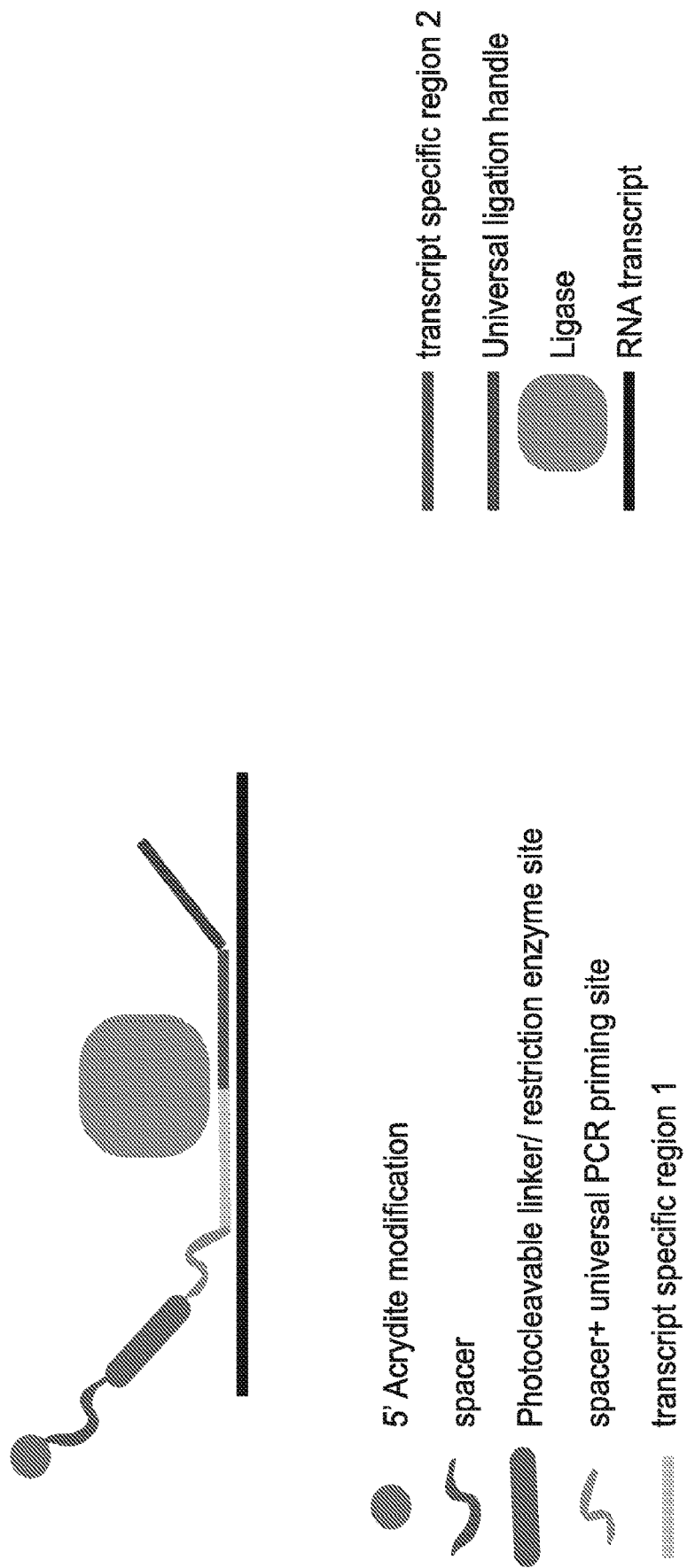
FIG. 8 illustrates dual probe detection of an RNA transcript or sgRNA using adjacently binding probes that are ligated, such that only dually detection events are amplified.
Figure 9:
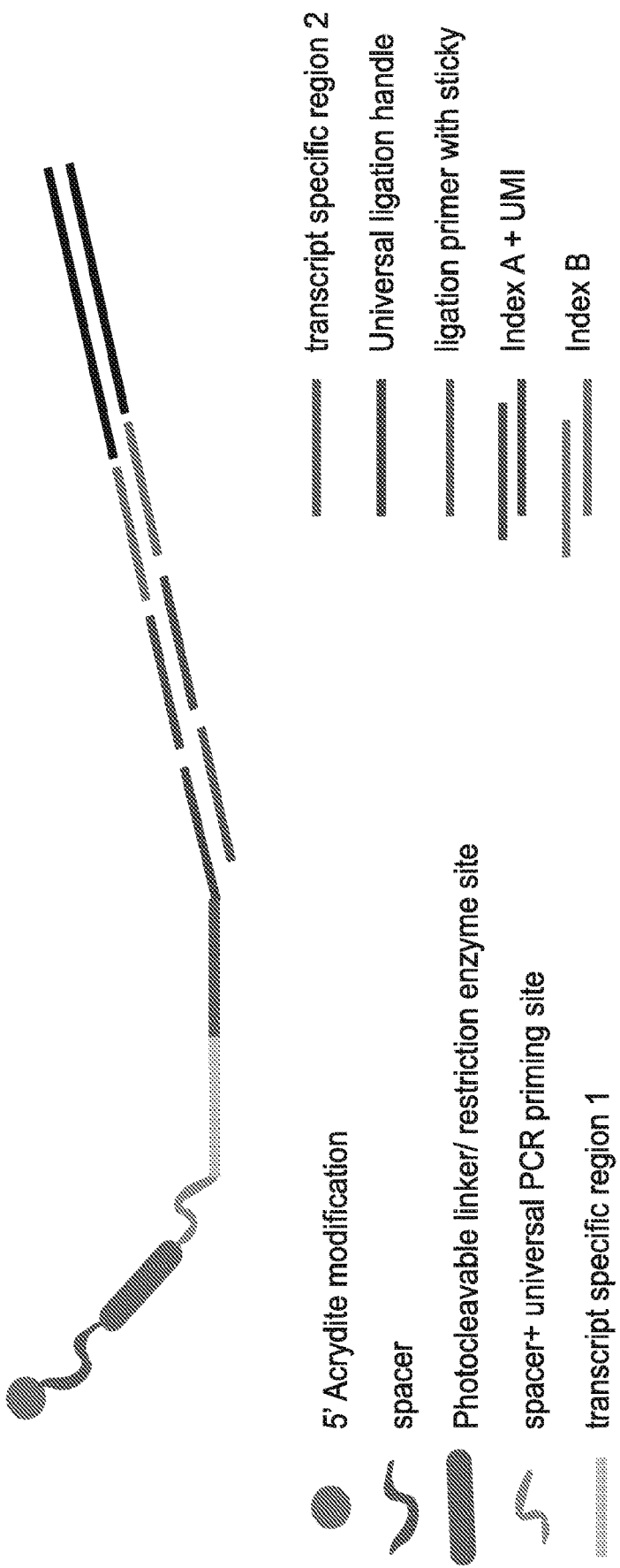
FIG. 9 illustrates staining with the ligation primer and performing split-pool ligation with an Index A containing a UMI.

The hydrogel mesh provides a physical framework, chemically incorporates biomolecules and is permeable to macromolecules such as antibodies (Chung et al., 2013). Lipids are cleared as described (Chung et al., 2013). FIGS. 2 A and B shows hydrogel embedded cells that have been fluorescently stained for genomic DNA, the intracellular protein PCNA, and surface marker CD51. In addition, applicants are able to detect protein levels present in the hydrogel encapsulated cell as shown FIG. 2C, where a GFP KI cell line was stained with an Alexa647 anti-GFP antibody, and a spearman correlation of 0.98 is observed by FACS measurement, whereas a BD Cytofix/perm protocol led to a correlation of 0.36. This shows that clearance of the lipids and the porosity of the hydrogel allow for more efficient washing and removal of unspecific antibodies. This higher accuracy of measurement is especially crucial in a high multiplex measurements and computational inference of regulatory mechanisms.

Example 3

Measuring Protein Levels

FIGS. 3 to 5 and 16 describe embodiments of structures of high affinity binding ligands used in the present invention for measuring protein levels. In these examples, an antibody is bound to an oligonucleotide label through a 5' amino modifier. Any linker chemistry known in the art may be used. An exemplary oligonucleotide structure may be: [5' Amino Modifier]-[~6 bp spacer]-[PhotoCleavable linker]-[~4 bp spacer]-[Illumina PCR primer]-[~8-16 bp UMI]-[~21 bp UCI]-[~20 bp universal ligation handle]. The UMI may be omitted using alternative UMI schemes described herein.

The first step in measuring protein levels may be to stain polymer matrices in bulk with oligo conjugated antibodies. In a second step, generation of a USI is performed by hybridization of a ligation primer that binds to the universal ligation handle on the oligo and provides the sticky end needed for ligation of index A. Optionally, extension may be performed to generate a dsDNA oligo tag before performing split-pool ligation. In a third step, split-pool ligation using the single-cell hydrogel drops as the basic unit is performed by ligation on the ligation handle Index A, B and [C+(UMI)+PCR primer]. The UMI may be on any index, as described herein. In a fourth step, sorting is performed to obtain the desired amount of cells to sequence. The oligo is released from the antibody (photocleave/restriction enzyme digestion) and amplified by Illumina PCR, or T7 amplification followed by a few PCR cycles should complexity of PCR libraries be low. In preferred embodiments, a dsDNA oligo is conjugated to the antibody. Not being bound by a theory, the dsDNA oligo is more stable and there is less chance of nonspecific binding. Not being bound by a theory, including the UMI in C index allows for improved cluster detection, such that the first bases for clustering during sequencing are random. Including a dsDNA oligo obviates the need for 'hybridization of ligation primer' step.

Example 4

Measuring RNA Levels

FIGS. 6 to 9 and 17 describe embodiments of structures of high affinity binding ligands used in the present invention for measuring RNA levels. The first step in measuring RNA levels may be to stain polymer matrices in bulk with oligonucleotide sequences that bind to a sgRNA or RNA transcript adjacent to each other. Alternatively, cells may be lysed, followed by hybridization and ligation in droplets before the initiation of polymerization. The acrylic phosphoramidite modification allows for the oligonucleotide to be incorporated into polymer mesh upon polymerization.

Two alternative embodiments may be used to measure RNA levels. In one embodiment RNA levels are measured by single probe detection. A single DNA probe that specifically binds to target transcript may be used. Additionally, multiple probes binding to different sites on a single transcript may be used. In preferred embodiments, sgRNA's are detected using a single probe. Not being bound by a theory, sgRNA only needs to be detected significantly above background and not precisely quantified.

In another embodiment, RNA levels are measured by dual probe detection. Adjacently binding probes are ligated, such that only dually detection events are amplified. This approach reduces noise and obviates the need to wash, so could be done after cell lysis with subsequent polymerization without the need to wash out unbound probes.

The second step in measuring RNA levels is to stain with a ligation primer as described herein and perform split-pool as described herein. In an alternative embodiment, Index A or C now contains a UMI. Inclusion of the UMI in an index sequence used for generating a USI is applicable to all of the methods described herein. Not being bound by a theory, including the UMI in the Index avoids unspecific binding that is outside of one's control due to the random nature of a UMI sequence. As Index A or C+UMI is dsDNA, unspecific binding during staining is unlikely to occur using this approach. In the Index A or C+UMI scheme, there is no UMI in the oligonucleotide label conjugated to the antibody. Therefore, Applicants can conjugate dsDNA oligos and advantageously provide for more stable storage and the elimination of potential off target binding. Moreover, the oligonucleotide label can already include the 'universal ligation handle' with a sticky end, eliminating the hybridization step.

Figure 17:
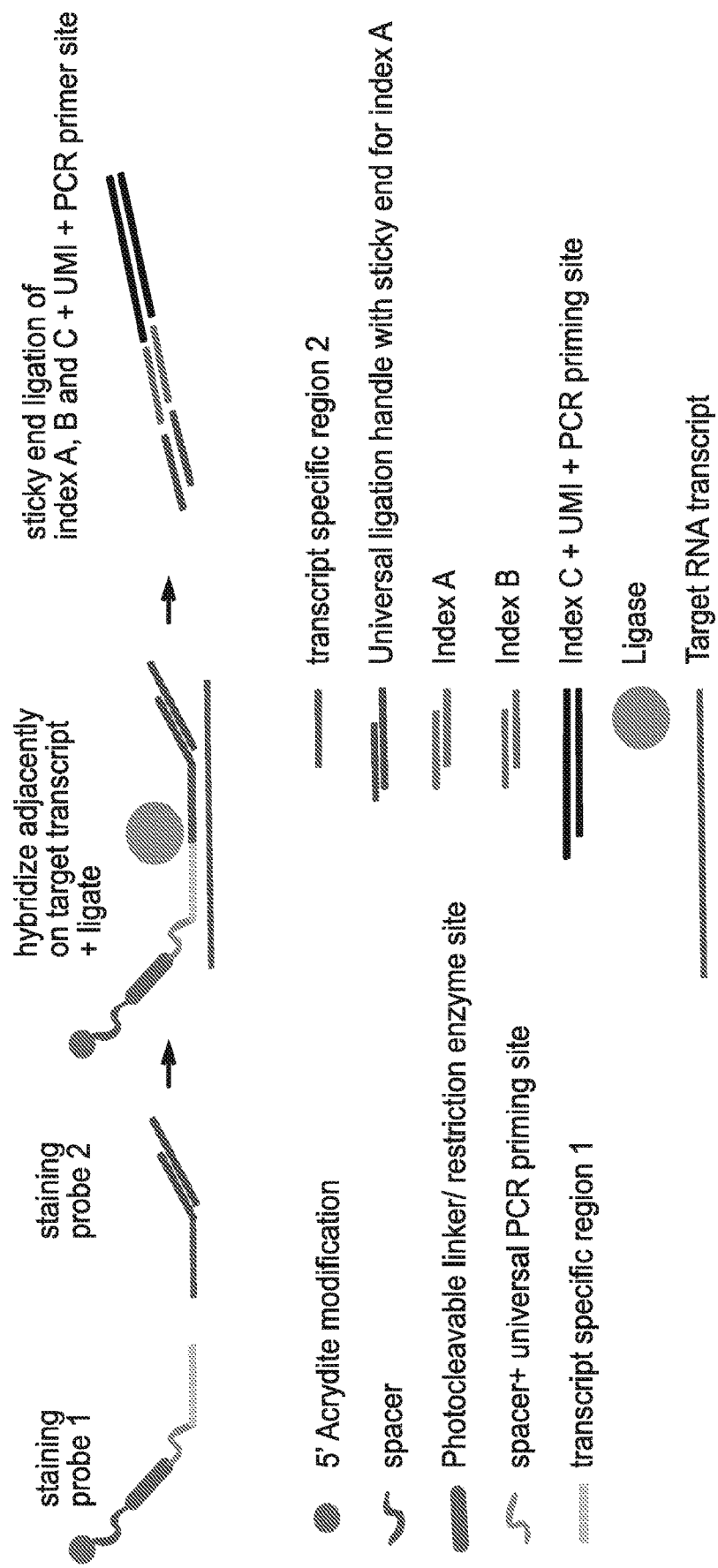
FIG. 17 illustrates alternative embodiments of measuring RNA levels.
Figure 19:
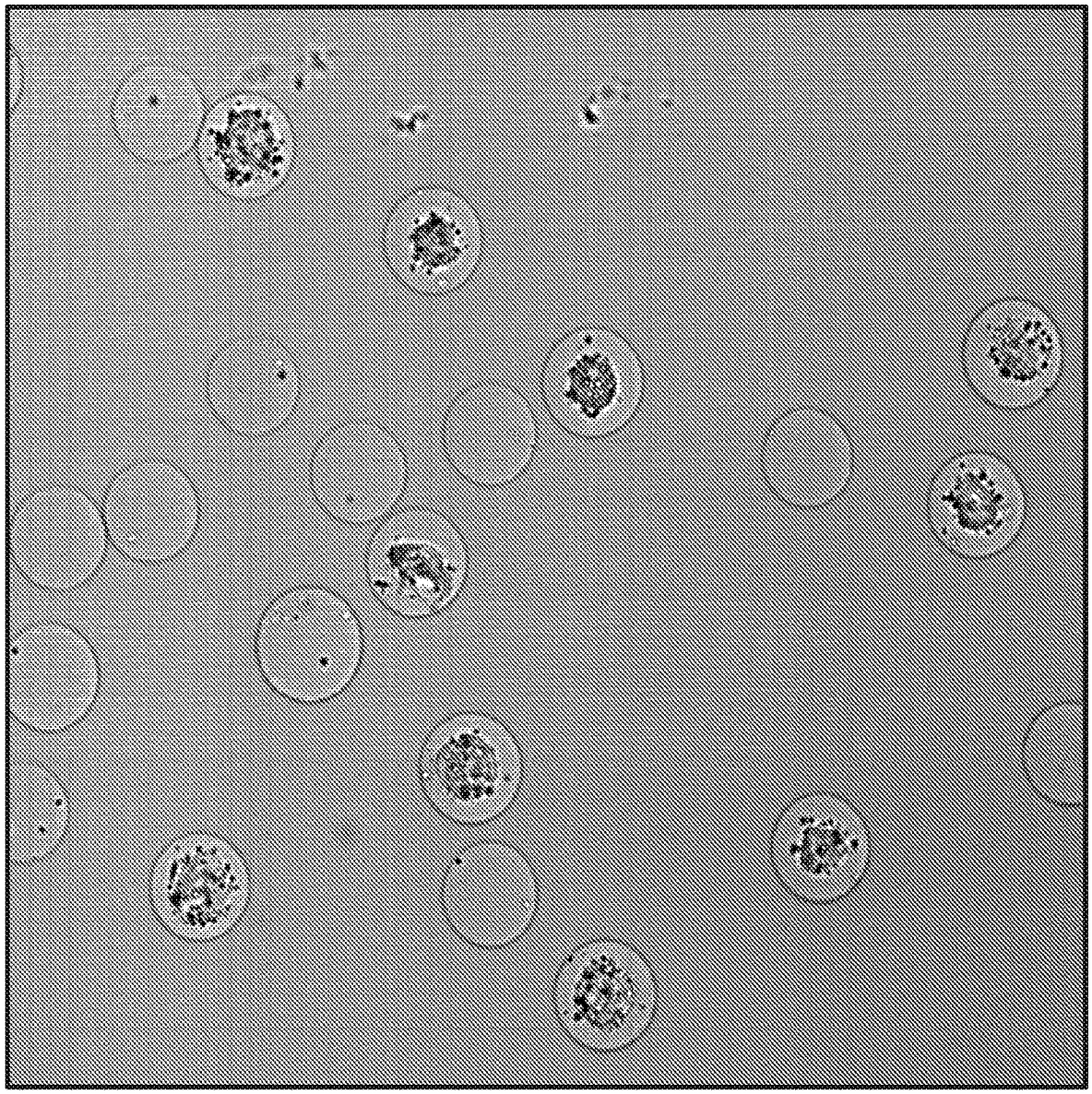
FIG. 19 illustrates a brightfield microscopy image showing hydrogel droplet encapsulated cells with magnetic particles embedded into the droplets to enable magnetic separation, aiding in clean up and washing steps in multiple reactions. Greatly enhances automation and therefore throughput.

FIG. 17 shows how probe 2 is pre-hybridized with a complementary second strand that also already provides overhang for sticky end ligation. Similarly, when staining with a single probe, this is pre-hybridized as well.

Example 5

Generation of Index+UMI

FIGS. 10 and 18 describes an exemplary protocol for generating an Index A or C that includes a UMI. The first step is to synthesize ssDNA with the indicated structure. The second step is to hybridize a primer providing a sticky end at 3' end. The third step is to use DNA polymerase for second strand synthesis. The final step is restriction enzyme digestion to generate the 5' sticky end.

Example 6

Measuring Protein-Protein Complexes

Figure 11:
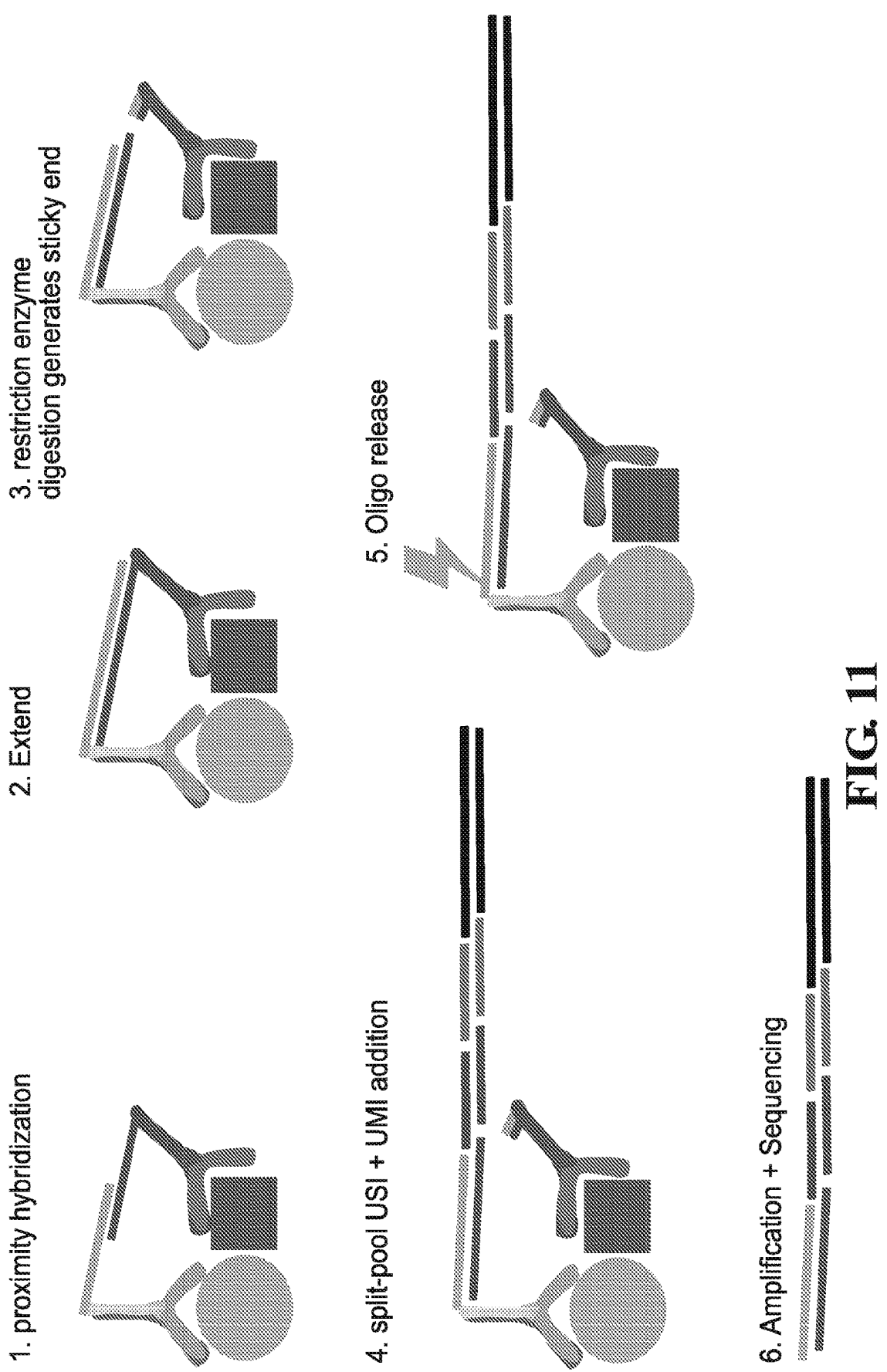
FIG. 11 illustrates measuring protein-protein complexes by performing a restriction enzyme digestion to generate an oligonucleotide containing two UCI and a compatible end for ligation to an index A for split-pool ligation.
Figure 12:
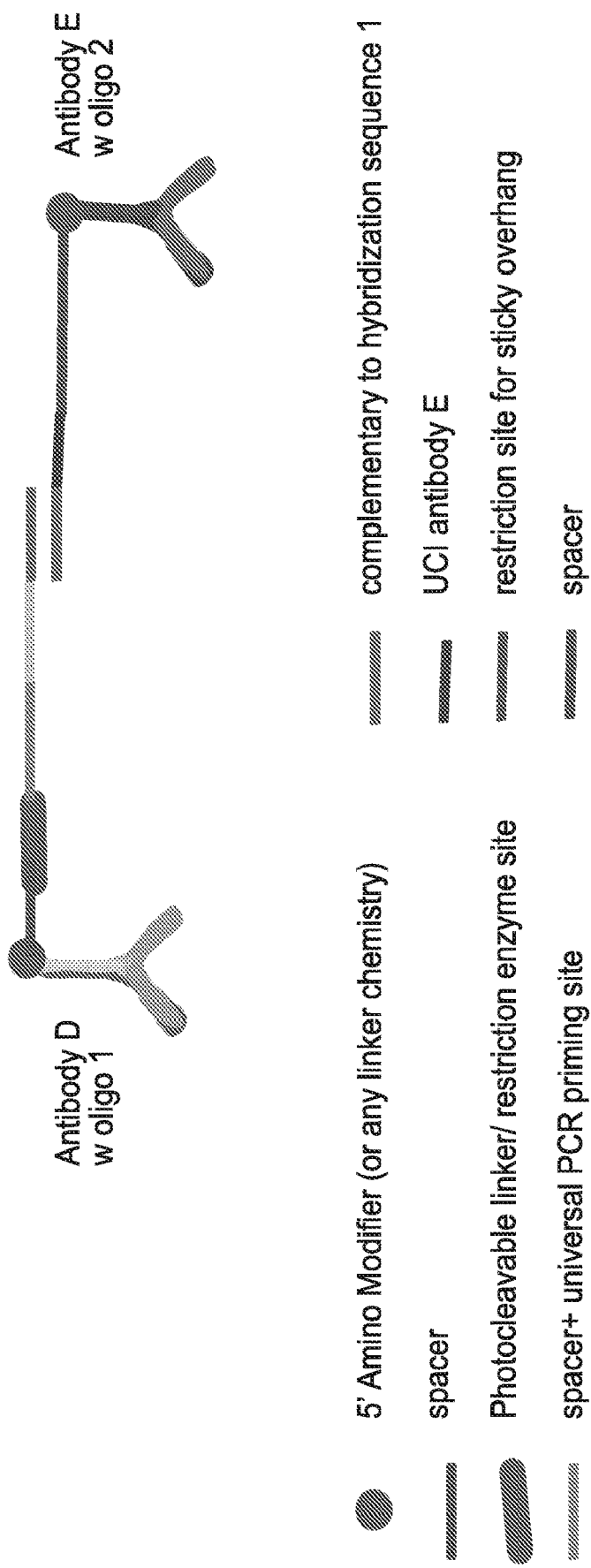
FIG. 12 illustrates oligonucleotide structures for measuring protein-protein complexes. Oligo 1: [5' Amino Modifier]-[~6 bp spacer]-[PhotoCleavable linker]-[~4 bp spacer]-[Illumina PCR primer]-[~21 bp UCI]-[~11 bp Hybridization sequence 1]. Oligo 2: [5' Amino Modifier]-[~6 bp spacer]-[RE site for sticky overhang]-[~21 bp UCI]-[~11 bp Hybridization sequence 1 complement].

FIGS. 11 and 12 describe embodiments of an overall scheme for measuring protein-protein complexes. The basic protocol in FIGS. 11 and 12 utilizes a restriction enzyme digestion coupled to the split-pool ligation protocol described herein. In order to use the Proximity extension Assay described, for each target in a panel, Applicants split an antibody vial into two sets, and label each set with either oligo 1 or oligo 2, such that for each pair of targets, there are complementary hybridization sequences. In step 1, this results in probes that are incompatible, in the case of monoclonal antibodies, 50% of the time. Exemplary, oligonucleotide labels may be:

Oligo 1: [5' Amino Modifier]-[~6 bp spacer]-[Photo-Cleavable linker]-[~4 bp spacer]-[Illumina PCR primer]-[~21 bp UCI]-[~11 bp Hybridization sequence 1]

Oligo 2: [5' Amino Modifier]-[~6 bp spacer]-[RE site for sticky overhang]-[~21 bp UCI]-[~11 bp Hybridization sequence 1 complement]

After restriction enzyme digestion and split-pool USI incorporation, the final oligonucleotide label to sequence contains a pair of UCI's identifying the two proteins in proximity, a UMI and a cellular barcode (Unique source identifier, USI). In preferred embodiments, hybridization length is 9-13 nt. Compared to PEA in solutions, the present invention provides the advantage of the ability to wash away unbound probes, greatly reducing background. Moreover, staining and washing at ~37° C. will melt the hybridization sequence, thus enabling to wash out unbound antibodies, and prevent randomly bound oligo pairs.

In another embodiment, Applicants use polyclonal antibodies, instead of monoclonal, to capture more complexes as the epitope of a monoclonal antibody might be inaccessible due to complex formation.

The Criteria for restriction enzymes are that they recognize a specific sequence which is not present in any of the oligo's conjugated to the antibody panel, they generate a 4-7 bp overhang that serves as a sticky end for ligation of USI indices, they have high fidelity, low star activity (preferably a HF factor >500), and the restriction enzyme works in a buffer that will not denature proteins (NEB Cutsmart). Alternatively, instead of proximity extension assays, Applicants use proximity ligation assays that have no hybridization sequence, but ligates DNA that is in proximity.

Example 7

Measuring Protein-RNA Complexes

Figure 13:
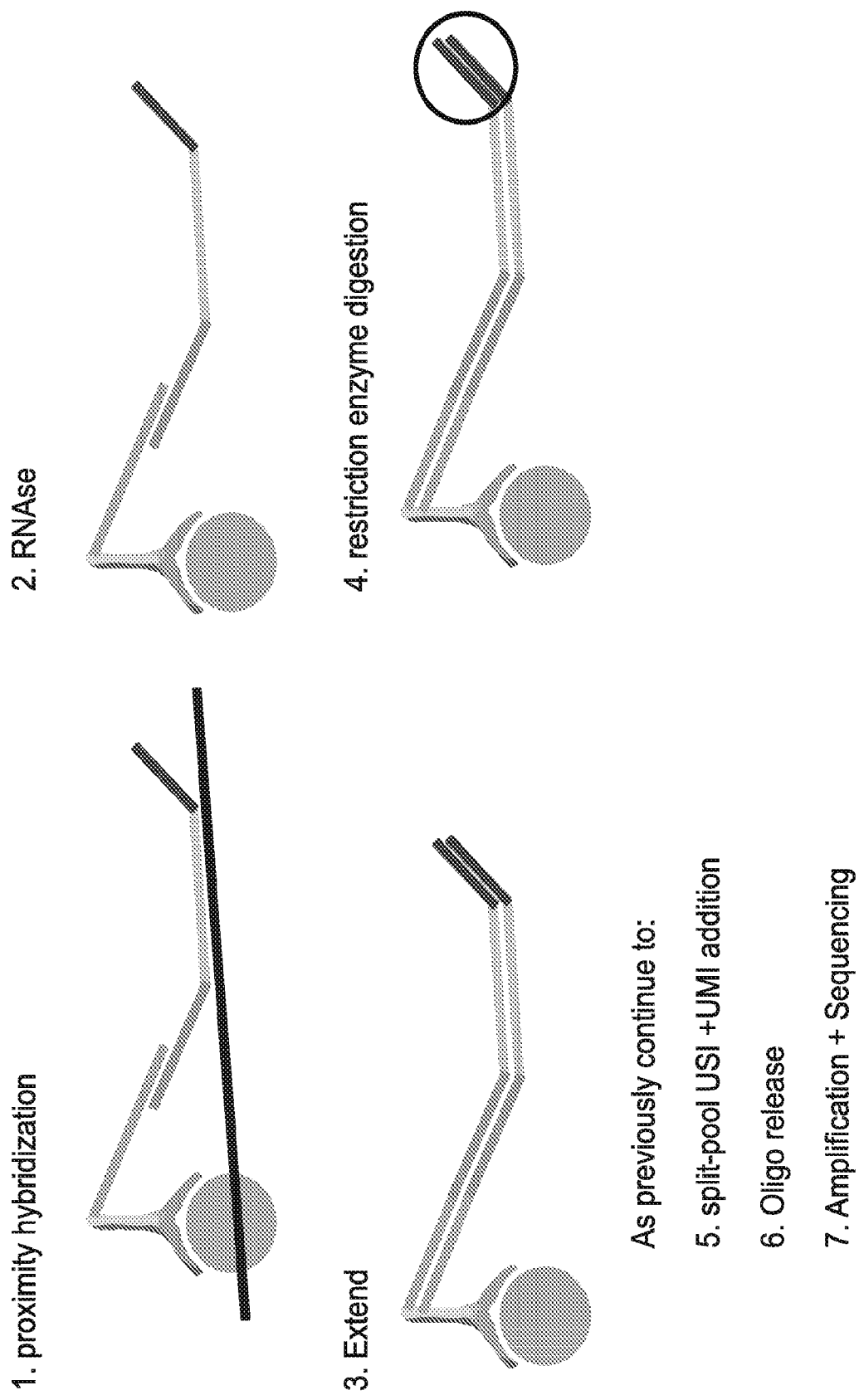
FIG. 13 illustrates measuring protein-RNA complexes using proximity hybridization. The Final oligonucleotide to sequence contains the UCI protein, UCI RNA and UMI+USI via split-pool ligation protocol.
Figure 16:
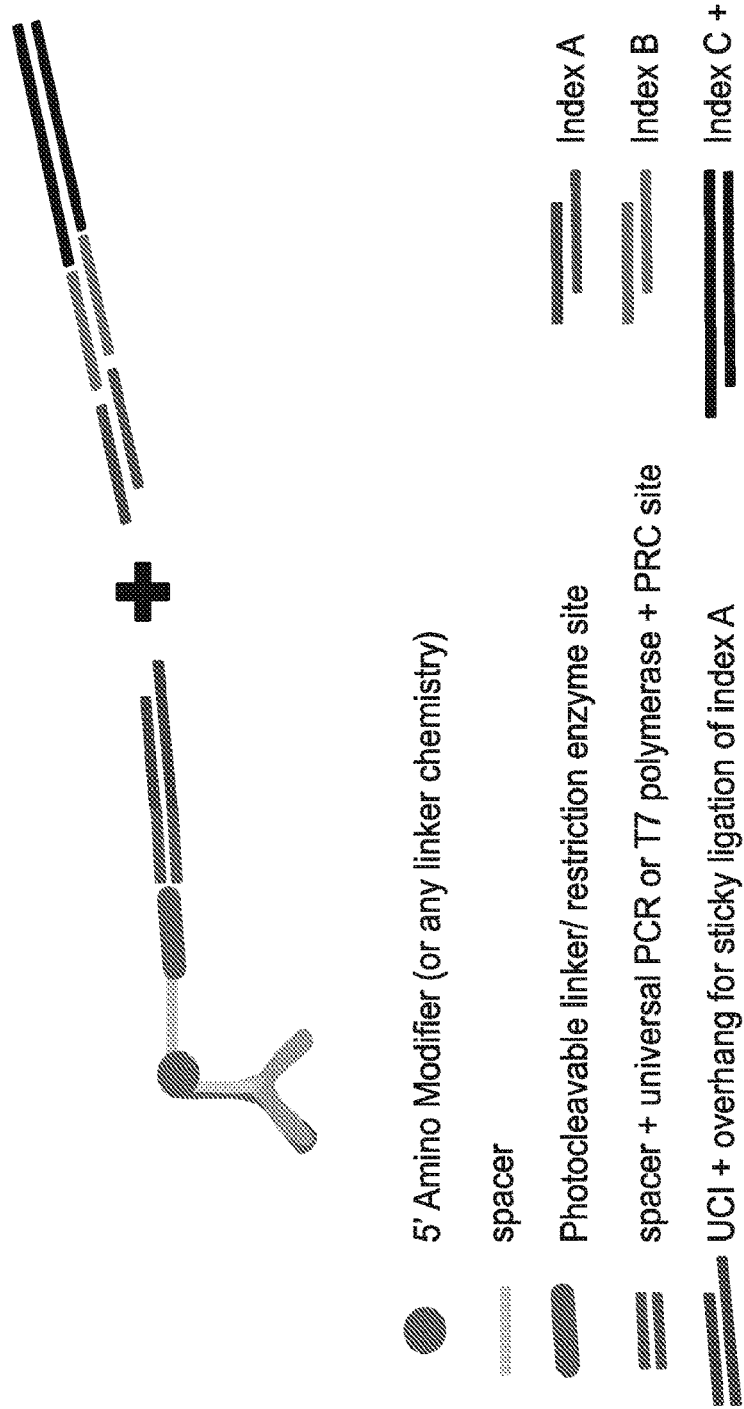
FIG. 16 illustrates staining with an antibody bound to an oligonucleotide label and performing split-pool ligation with an Index C containing a UMI.

FIG. 13 describes an embodiment of measuring protein-RNA complexes. In this embodiment, all antibodies have an oligo1 format conjugated to them and all RNA probes have the complementary hybridization sequence (i.e., 100% compatible). The final oligo to sequence contains a UCI protein, a UCI RNA and a UMI+USI via the split-pool protocol, thus reporting on protein-ma proximity.

Example 8

High Throughput Single-Cell ATAC-Seq

FIGS. 14 and 15 describe embodiments of performing single-cell ATAC-seq.

Single-cell ATAC-seq detects open chromatin in individual cells. ATAC-seq (assay for transposase-accessible chromatin) identifies regions of open chromatin using a hyperactive prokaryotic Tn5-transposase, which preferentially inserts into accessible chromatin and tags the sites with sequencing adaptors (Buenrostro J D, Giresi P G, Zaba L C, Chang H Y, Greenleaf W J. Transposition of native chromatin for fast and sensitive epigenomic profiling of open chromatin, DNA-binding proteins and nucleosome position. Nat Methods. 2013; 10:1213-128). The protocol is straightforward and robust and has become widely popular. Up to this point, ATAC-seq and other methods for the identification of open chromatin have required large pools of cells (Buenrostro, 2013; Thurman R E, Rynes E, Humbert R, Vierstra J, Maurano M T, Haugen E, et al. The accessible chromatin landscape of the human genome. Nature. 2012; 488:75-82), meaning that the data collected reflect cumulative accessibility across all cells in the pool. Independent studies have modified the ATAC-seq protocol for application to single cells (scATAC-seq) (Buenrostro J D, Wu B, Litzenburger U M, Ruff D, Gonzales M L, Snyder M P, et al. Single-cell chromatin accessibility reveals principles of regulatory variation. Nature. 2015; 523:486-90; and Cusanovich D A, Daza R, Adey A, Pliner H A, Christiansen L, Gunderson K L, et al. Epigenetics. Multiplex single-cell profiling of chromatin accessibility by combinatorial cellular indexing. Science. 2015; 348:910-4). These studies provide data on hundreds (Buenrostro, 2015) or thousands (Cusanovich, 2015) of single cells in parallel. Both methods are limited in either the number of cells analyzed or the per-cell coverage. The present invention can be used to isolate chromatin from individual cells in isolated hydrogel matrices, thus allowing for the first time the advantages of both protocols for sc-ATAC. Thus, large numbers of cells may be analyzed and high per-cell coverage achieved. The overall scheme requires temperature controlled microfluidics with microinjection capabilities. The first step requires lysing cells and tagmentation of genomic DNA using the described adapters in discrete reaction vessels. The reaction vessel is preferably a droplet. The droplet or reaction vessel is then infused with monomers of a polymerizable gel and is polymerized. A sticky end is generated and the DNA is extended. A USI is generated by the split-pool ligation method. The UMI is incorporated during USI generation. Amplification by either PCR or T7 amplification is performed and the products are sequenced together.

Example 9

Measuring Protein-DNA Complexes

FIG. 15 describes an embodiment of combining single-cell ATAC-seq and the protein methods described herein to measure protein-DNA complexes. In this embodiment, all antibodies can have an oligo 1 format conjugated to them and all genomic DNA has the complementary hybridization sequence (i.e., 100% compatible). After tagmentation and gel polymerization, the polymer matrices are incubated with antibodies as described herein. The final oligonucleotide label to sequence contains a UCI protein, a genomic DNA sequence and UMI+USI via the split-pool protocol, thus reporting on protein-DNA proximity.

Example 10

Multi-Omics Measurements

Importantly, due to the use of identical final steps of each protocol (extend, restriction, split-pool USI+UMI addition) it is possible to combine proteomics measurements with RNA, protein-protein, protein-RNA and protein-DNA measurements, offering a powerful multi-omic measurement platform.

Example 11

Measuring Protein Complexes Consisting of Two or More Cellular Constituents

Turning to FIG. 20, Applicants have developed a novel probe that can be used to detect protein complexes including of 2 or more cellular constituents at the same time. In one embodiment, the probe (ULI, Unique Location Identifier) is constructed by synthesizing ssDNA with a restriction enzyme site, followed by a Unique Location Index, a Universal hybridization site, and a spacer. The ssDNA is circularized and amplified by rolling circle amplification. The resulting probe has multiple repeats of the same elements. The probe may have any number of repeats, preferably 3 to 10 repeats. The restriction enzyme site allows the probe to be cleaved into individual segments, as well as allowing for a sticky end that can be used to generate a USI by the split pool ligation method. The ULI is a unique sequence that can be used to distinguish different protein complexes. All cellular constituents in a complex and bound by a labeling ligand comprising an oligonucleotide label that also includes a universal hybridization sequence will hybridize to the same probe. The resulting oligonucleotide label of all of the cellular constituents bound to the same probe will have the same ULI and thus, after sequencing the complexes can be resolved. FIG. 21 illustrates an overall scheme to measure the proximity of 3 or more proteins, RNA or DNA molecules. The first step is binding of the hybridization sequence of ligand bound oligo to the complementary hybridization site on the ULI probe. The second step is extension, such that each ligand bound oligo incorporates the same ULI. The third step is a restriction enzyme digestion to generate a 4 bp overhang. The fourth step is to perform sticky end ligation to generate a USI+UMI on the oligonucleotide label. The third index used to generate the USI includes a priming site for sequencing or amplification followed by sequencing. Only the top strand includes the UCI, and PCR fwd and rev primer sites and will thus be exponentially amplified.

Example 12

Protocols

This protocol is used to prepare the hydrogelled single cells, and is an adaptation of a protocol described previously (doi:10.103/nprot.2014.123):

| Make HM solution (400 mL) | | |
|---|---|---|
| 1 | Mix | For 4%/0.05% |
| | 40% wt/vol acrylamide | 40 ml |
| | 2% (wt/vol) bisacrylamide | 10 mL |
| | 10X PBS | 40 mL |
| | 16% (wt/vol) PFA | 100 mL |
| | Distilled water | 210 mL |
| | 0.1% (w/v) ammonium persulfate VA-044 thermal initiator | 1 g |
| 2 | Keep reagents on ice | |
| 3. | Make 10 ml aliquots and freeze at −20° C. | |
| Make SBC solution | | |
| 4 | Prepare stock of 20% (wt/vol) SDS in H20 (store at RT for weeks) | For 4%/0.05% |
| | 40% wt/vol acrylamide | 40 ml |
| 5 | Prepare 1M boric acid buffer (pH adjusted to 8.5). 10 g boric acid, 61.83 g NaOH. Dissolve in 700-800 mL, pH 8.5, and Q.S. to 1L. With a little heat is | |
| 6 | Freshly prepare clearing buffer by diluting 4&5 five fold in distlled water and combine them | |

Procedure

7   Prepare the HM stock solution by thawing frozen vials on ice or in a refridgerator. Gently mix the thawed monomer solution by inverting. Keep all reagents on ice during the whole procedure. CRITICAL STEP Make sure that there is no precipitation floating in the monomer solution; this is an indicator of spontaneous polymerization of the stored monomer solution -continued 8. Incubate the cell in HM (0.5-1k cells/ μL)
9. Put samples in coolrack, open cap, and leave in dessicator vacuum for 10 minutes
10. Disconnect vacuum, keep nitrogen just above atmospheric pressure run microfluidic droplet formation whereby microfluidic channel size is adapted to generate droplets slightly larger then the cell size,
11. use Biorad oil for droplet generation spiked with 0.4% TMED
12. Incubate at 60° C. in thermocycler overnight
13. Wash sample twice with SBC buffer for 1 h at room temperuature to dialyzed the remaining PFA, initiator and monomer.
14. Passive clearing of hydrogel-embedded tissue by gentle shaking in SBC buffer at 37/60° C. for 2-6 hours
15. Wash with boric acid buffer (0.2M/pH 8.5 with 0.1% (vol/vol) Triton X-100) for 1-3 h at 37° C.
16. Resuspend cells in PBST (0.1% Triton X in 1X PBS) for 30 min
17. Incubate in antibody/PST solution for 2-6 hours at 37° C., DAP (1 ug/ml), can also be added at this step
18. Wash off the antibodies with PBST at 4° C. for 2 hours.
19. Samples can be stored in PBST (with 0.01% (wt/vol) sodium azide) at 4° C. for up to a week Oligos are Conjugated to the Antibodies using the Following Kit:

| Product Name | Antibody-Oligonucleotide All-in-One Conjugation Kit |
|---|---|
| Product ID | A-9202-001 |
| Vendor | Solulink |

For the nanobody pilot, Oligo's will be conjugated to nanobodies using a protocol developed by our collaboration Ploegh Lab:
http://www.nature.com/nprot/journal/v8/n9/abs/nprot.2013.102.html
After Cells are Hydrogelled and Stained with Oligo-Antibodies or Oligo-Nanobodies, Currently We Envision 3 Methods of Processing:
  1 multiwell PCR amplification (low throughput)
  2 microfluidic encapsulation and oligo capture using beads (high throughput)
  3 microwell loading and oligo capture using beads (high throughput)
Option 1
Here Applicants proceed as follows:
antibodies were conjugated to an oligo with the following components:
[Illumina adaptors]-[4-7bp Unique Molecular Identifier (UMI)]-[21bp UCI]-[illumina adaptor]
illumina adaptors are used as in the Illumina 16s protocol (page3):
http://supportres.illumina.com/documents/documentation/chemistry_documentation/16s/16s-metagenomic-library-prep-guide-15044223b.pdf
Hydrogelled cells that are sorted directly into a PCR mix undergo a first PCR amplification with primers binding to the Illumina adaptors.
In a second PCR reaction, Illumina nextera indices, providing a cellular barcode, are used for amplification.
After this PCR reaction, libraries can be pooled and NGS sequenced.

Alternative Amplification Scheme: Rolling Circle Amplification

Option 2
antibodies were conjugated to an oligo with the following components: [Illumina adaptors]-[21bp protein barcode]-[binding sequence]

Beads are constructed and joined with hydrogelled cells as reported in: doi:10.1016/j.cell.2015.05.002 http://wwww.sciencedirect.com/science/article/pii/S0092867415005498 or alternatively in: 10.1016/j.cell.2015.04.044
http://www.sciencedirect.com/science/article/pii/S0092867415005000

As mentioned in 'SC_NGS_proteomics.docx', this approach allows for pooling right after the oligo capture phase and pooled library preparation.

Option 3
Similarly load beads described above, but instead of using droplets, we would use microwells such as described in:
10.1126/science.1258367 http://www.sciencemag.org/content/347/6222/1258367.abstract
This protocol is used after cells are hydrogelled, and is an adaptation of the protocol described in:
http://www.olink.com/sites/default/files/0935%20v1.5%20Proseek%20Multiplex%20User%20Manual_final.pdf
specifics of assay
type:http://journals.plos.org/plosone/article?id=10.1371/journal.pone.00951

| Reagents 4° C | |
|---|---|
| Incubation Solution | Contains components needed for the incubation reaction |
| A-probes | Contains 96 antibody probes labeled with A oligos |
| B-probes | Contains 96 antibody probes labeled with B oligos |
| Reagents -20° C | |
| PEA Solution | Contains components needed for the extension reaction |
| PEA Enzyme | For extension of A and B probes which are bound to their target |
| PCR Polymerase | For pre-amplification of the extension product created by the PEA enzyme |
| Detection Solution | Contains components needed for the detection reaction |
| Detection Enzyme | For qPCR amplification |
| Primer Plate | 96-well plate with ready-to-use primers for amplification of extension product |
| Interplate Control | For normalization between runs |
| Negative Control | For determination of background levels |
| Incubation Stabilizer | For stabilization of the incubation reaction |

| PEA PROGRAM | | |
|---|---|---|
| Step | T [C.] | time [min] |
| Extension | 50 | 20 |
| Hot start | 95 | 5 |
| PCR Cycle | 95 | 0.5 |
| | 54 | 1 (17x) |
| | 60 | 1 |
| Maintain the reaction at | 10 | indef |

| PEA PCR after 17 cycles, take out control wells, and for single SC cell wells perform: | | |
| --- | --- | --- |
| Step | T [C.] | time [min] |
| Hot start | 95 | 5 |
| PCR Cycle | 95 | 0.5 |
| | 54 | 1 (17×) |
| | 60 | 1 |
| Maintain the reaction at | 10 | indef |

| BIOMARK PROGRAM | | |
| --- | --- | --- |
| step | T [C.] | time [s] |
| Thermal mix | 50 | 120 |
| | 70 | 1800 |
| | 25 | 600 |
| Hotstart | 95 | 300 |
| PCR Cycle | 95 | 15 |
| | 60 | 60 40× |

| INCUBATION MIX | | |
| --- | --- | --- |
| Reagent | per 96well plate [ul] | ¼th of original |
| Incubation Solution | 70 | 52.5 |
| Incubation Stabilizer | 10 | 7.5 |
| A-probes | 10 | 7.5 |
| B-probes | 10 | 7.5 |
| Total | 100 | 75 |

| EXTENTION MIX | | |
| --- | --- | --- |
| Reagent | per 96well plate [ul] | ~⅓rd of original |
| High Purity Water | 3081.5 | |
| PEA Solution | 361.2 | |
| PEA Enzyme | 18.1 | |
| PCR Polymerase | 7.2 | |
| Total | 3468 | |

| DETECTION MIX | |
| --- | --- |
| Reagent | per 96well plate [ul] |
| Detection Solution | 550 |
| High Purity Water | 230 |
| Detection Enzyme | 7.8 |
| PCR Polymerase | 3.1 |
| Total | 790.9 |

| | | |
| --- | --- | --- |
| Day 1 Incubation | 1 | Thaw samples, vortex and spin down the content at 150 × g, 1 min at room temperature. |
| | 2 | Thaw the Incubation Stabilizer from the Proseek Multiplex Detection Kit 96 × 96 box, vortex and spin briefly. |
| | 3 | Thaw the Interplate Control and Negative Control from the Proseek Multiplex Controls box, vortex and spin briefly. |
| | 4 | Prepare the Incubation mix in a microcentrifuge tube. Vortex and spin each reagent before transfer to the mix. |
| | 5 | Vortex the Incubation mix briefly and spin down the content. |
| | 6 | Use a multi-channel pipette to transfer 3 μL of the Incubation mix from the 8-well strip to the bottom of control wells of a 96-well plate by using reverse pipetting. Do not change pipette tips. Name this plate Incubation Plate. |
| | 7 | Add remaining 82 ul of incubation mix to hydrogelled mixture |
| | 8 | Add 1 μL of Negative Control to the bottom of each well in position C12, D12 and E12 according to the plate layout in FIG. 2. |
| | 9 | Add 1 μL of Interplate Control to the bottom of each well in position F12, G12 and H12 |
| | 10 | Seal the Incubation Plate with an adhesive plastic film. It is important that all wells are properly sealed, especially around the edges to avoid evaporation of samples. Spin down the content at 150 × g, 1 min at room temperature. |
| | 11 | Incubate the Incubation Plate overnight at +2° C. to +8° C. |
| | 12 | Incubate the hydrogelled cell-incubation mix mixture while rotating at 37° C. for 6 h, followed by heavy dilution and 2 × 3 h of PBST washes at 4° C. |
| Day 2 Extension | 13 | Turn on your thermal cycler and activate the heated lid function. |
| | 14 | Thaw the PEA Solution, vortex and spin briefly. Prepare the Extension mix in a centrifuge tube. Use a freezing block when removing the PEA Enzyme and the PCR Polymerase from −20° C. and spin down the content briefly before pipetting the enzymes into the mix. |
| | 15 | Vortex the Extension mix. |
| | 16 | Bring the Incubation Plate to room temperature. Spin down the content at 150 × g, 1 min at room temperature. |
| | 17 | Pour the Extension mix into a multi-channel pipette reservoir. |
| | 18 | Pipette 24 ul of extension mix into 96 well plate, then sort single (hydrogelled) cells into single wells, keep on ice while sorting |
| | 19 | After sort, take 96 ul extension mix for control wells, mix with content of corresponding wells in incubation plate, and reintroduce into original 96 well |

| | | |
|---|---|---|
| | 20 | Start a timer set for 5 min and transfer 96 µL of Extension mix to each well of the Incubation Plate by using reverse pipetting. Do not change pipette tips, place the tips against the upper parts of the well wall. Make sure the tips never come in contact with the contents of the wells. |
| | 21 | Add a new plastic adhesive film to the Incubation Plate. It is important that all wells are properly sealed, especially around the edges to avoid evaporation of samples. |
| | 22 | Vortex gently and spin down the content at 150 × g, 1 min at room temperature. |
| | 23 | Note: Perform steps 19-21 within 5 minutes. |
| | 24 | After the 5 min, place the Incubation Plate in the thermal cycler and run the PEA program (see section 5.2 for details). The PEA program takes approximately 1 h 40 min. |
| | 25 | Take out controls and run PEA PCR SC program for the wells with the single cells |
| | 26 | Note: If your thermal cycler requires a silicon cover for plates covered with plastic film, please use one to avoid evaporation. |
| | 27 | Continue with the Detection step or store the Incubation Plate for up to one week at +4° C. |
| Detection | 28 | Prepare and prime a 96.96 Dynamic Array IFC according to the manufacturer's instructions. |
| | 29 | Thaw the Primer Plate, vortex and spin at 150 × g, 1 mm at room temperature. |
| | 30 | Thaw the Detection Solution, vortex and spin briefly. Prepare the following Detection mix in a microcentrifuge tube. Use a freezing block for the Detection Enzyme and PCR Polymerase and spin down the content briefly before pipetting the enzymes into the mix. |
| | 31 | Vortex the Detection mix and spin briefly. Transfer 95 µL of the Detection mix per well to an 8-well strip. |
| | 32 | Use a multi-channel pipette to transfer 7.2 µL of Detection mix to each well of a new 96-well plate by reverse pipetting. Name this plate Sample Plate. |
| | 33 | Remove the Incubation Plate from the thermal cycler, vortex and spin down the contents. |
| | 34 | Carefully remove the plastic film and transfer 2.8 µL from each well of the Incubation Plate to the Sample Plate. |
| | 35 | Seal the Sample Plate with a new plastic adhesive film, vortex and spin at 150 × g, 1 min at room temperature. Note: For steps 31 and 32, make sure not to leave any inlets empty on the chip. |
| | 36 | Transfer 5 µL from each well of the Sample Plate to the primed 96.96 Dynamic Array IFC by using reverse pipetting. Change pipette tips after each sample. Samples are loaded into their respective inlets on the right side of the chip according to FIG. 3. See Appendix 1 for a detailed instruction on sample loading. |
| | 37 | Gently remove the Primer Plate aluminum sealing to avoid contamination between wells. Transfer 5 µL from each well of the Primer Plate into the inlets on the left side of the chip according to FIG. 3 by reverse pipetting. Change pipette tips after each transfer. |
| | 38 | Remove any visible bubbles, e.g. with a pipette tip or syringe needle and change between each well. |
| | 39 | Load the chip in the Fluidigm IFC Controller HX according to manufacturer's instructions. |
| | 40 | Run the Olink Protein Expression 96 × 96 Program in the Fluidigm Biomark Reader according to manufacturer's instructions. |

All publications, patents, and patent applications mentioned herein are incorporated by reference to the same extent as if each individual publication, patent or patent application was specifically and individually indicated to be incorporated by reference in its entirety.

Various modifications and variations of the described methods, pharmaceutical compositions, and kits of the invention will be apparent to those skilled in the art without departing from the scope and spirit of the invention. Although the invention has been described in connection with specific embodiments, it will be understood that it is capable of further modifications and that the invention as claimed should not be unduly limited to such specific embodiments. Indeed, various modifications of the described modes for carrying out the invention that are obvious to those skilled in the art are intended to be within the scope of the invention. This application is intended to cover any variations, uses, or adaptations of the invention following, in general, the principles of the invention and including such departures from the present disclosure come within known customary practice within the art to which the invention pertains and may be applied to the essential features herein before set forth.

REFERENCES

1 Adiconis, X., Borges-Rivera, D., Satija, R., DeLuca, D. S., Busby, M. A., Berlin, A. M., Sivachenko, A., Thompson, D. A., Wysoker, A., Fennell, T., Gnirke, A., Pochet, N., Regev, A. & Levin, J. Z. Comparative analysis of RNA sequencing methods for degraded or low-input samples. Nat Methods. 10, 623-629, doi:10.1038/nmeth.2483 (2013). PMCID:3821180.

2 Blecher-Gonen, R., Barnett-Itzhaki, Z., Jaitin, D., Amann-Zalcenstein, D., Lara-Astiaso, D. & Amit, I. High-throughput chromatin immunoprecipitation for genome-wide mapping of in vivo protein-DNA interactions and epigenomic states. Nat Protoc. 8, 539-554, doi:10.1038/nprot.2013.023 (2013).

3 Bochkis, I. M., Przybylski, D., Chen, J. & Regev, A. Changes in nucleosome occupancy associated with metabolic alterations in aged mammalian liver. Cell reports. 9, 996-1006, doi:10.1016/j.celrep.2014.09.048 (2014). PMCID:4250828.

4 Bornstein, C., Winter, D., Barnett-Itzhaki, Z., David, E., Kadri, S., Garber, M. & Amit, I. A negative feedback loop of transcription factors specifies alternative dendritic cell chromatin States. Mol Cell. 56, 749-762, doi:10.1016/j.molcel.2014.10.014 (2014). PMCID:4412443.

5 Cabili, M. N., Dunagin, M. C., McClanahan, P. D., Biaesch, A., Padovan-Merhar, O., Regev, A., Rinn, J. L. & Raj, A. Localization and abundance analysis of human lncRNAs at single-cell and single-molecule resolution. *Genome Biol.* 16, 20, doi:10.1186/s13059-015-0586-4 (2015). PMCID:4369099.

6 Cabili, M. N., Trapnell, C., Goff, L., Koziol, M., Tazon-Vega, B., Regev, A. & Rinn, J. L. Integrative annotation of human large intergenic noncoding RNAs reveals global properties and specific subclasses. *Genes Dev.* 25, 1915-1927, doi:10.1101/gad.17446611 (2011). PMCID: 3185964.

7 Chan, M. M., Smith, Z. D., Egli, D., Regev, A. & Meissner, A. Mouse ooplasm confers context-specific reprogramming capacity. *Nature genetics*. 44, 978-980, doi:10.1038/ng.2382 (2012). PMCID:3432711.

8 Cheng, C. S., Rai, K., Garber, M., Hollinger, A., Robbins, D., Anderson, S., Macbeth, A., Tzou, A., Carneiro, M. O., Raychowdhury, R., Russ, C., Hacohen, N., Gershenwald, J. E., Lennon, N., Nusbaum, C., Chin, L., Regev, A. & Amit, I. Semiconductor-based DNA sequencing of histone modification states. *Nat Commun.* 4, 2672, doi: 10.1038/ncomms3672 (2013). PMCID:3917140.

9 Chevrier, N., Mertins, P., Artyomov, M. N., Shalek, A. K., Iannacone, M., Ciaccio, M. F., Gat-Viks, I., Tonti, E., DeGrace, M. M., Clauser, K. R., Garber, M., Eisenhaure, T. M., Yosef, N., Robinson, J., Sutton, A., Andersen, M. S., Root, D. E., von Andrian, U., Jones, R. B., Park, H., Carr, S. A., Regev, A., Amit, I. & Hacohen, N. Systematic discovery of TLR signaling components delineates viral-sensing circuits. *Cell.* 147, 853-867, doi:10.1016/j.cell.2011.10.022 (2011). PMCID:3809888.

10 Engreitz, J. M., Pandya-Jones, A., McDonel, P., Shishkin, A., Sirokman, K., Surka, C., Kadri, S., Xing, J., Goren, A., Lander, E. S., Plath, K. & Guttman, M. The Xist lncRNA exploits three-dimensional genome architecture to spread across the X chromosome. *Science.* 341, 1237973, doi: 10.1126/science.1237973 (2013). PMCID:3778663.

11 Galonska, C., Smith, Z. D. & Meissner, A. In Vivo and in vitro dynamics of undifferentiated embryonic cell transcription factor 1. *Stem Cell Reports.* 2, 245-252, doi: 10.1016/j.stemcr.2014.01.007 (2014). PMCID:3964277.

12 Garber, M., Yosef, N., Goren, A., Raychowdhury, R., Thielke, A., Guttman, M., Robinson, J., Minie, B., Chevrier, N., Itzhaki, Z., Blecher-Gonen, R., Bornstein, C., Amann-Zalcenstein, D., Weiner, A., Friedrich, D., Meldrim, J., Ram, O., Cheng, C., Gnirke, A., Fisher, S., Friedman, N., Wong, B., Bernstein, B. E., Nusbaum, C., Hacohen, N., Regev, A. & Amit, I. A high-throughput chromatin immunoprecipitation approach reveals principles of dynamic gene regulation in mammals. *Mol Cell.* 47, 810-822, doi:10.1016/j.molcel.2012.07.030 (2012). PMCID:3873101.

13 Gat-Viks, I., Chevrier, N., Wilentzik, R., Eisenhaure, T., Raychowdhury, R., Steuerman, Y., Shalek, A. K., Hacohen, N., Amit, I. & Regev, A. Deciphering molecular circuits from genetic variation underlying transcriptional responsiveness to stimuli. *Nature biotechnology.* 31, 342-349, doi:10.1038/nbt.2519 (2013). PMCID:3622156.

14 Guttman, M., Donaghey, J., Carey, B. W., Garber, M., Grenier, J. K., Munson, G., Young, G., Lucas, A. B., Ach, R., Bruhn, L., Yang, X., Amit, I., Meissner, A., Regev, A., Rinn, J. L., Root, D. E. & Lander, E. S. lincRNAs act in the circuitry controlling pluripotency and differentiation. *Nature.* 477, 295-300, doi:10.1038/nature10398 (2011). PMCID:3175327.

15 Haas, B. J., Papanicolaou, A., Yassour, M., Grabherr, M., Blood, P. D., Bowden, J., Couger, M. B., Eccles, D., Li, B., Lieber, M., Macmanes, M. D., Ott, M., Orvis, J., Pochet, N., Strozzi, F., Weeks, N., Westerman, R., William, T., Dewey, C. N., Henschel, R., Leduc, R. D., Friedman, N. & Regev, A. De novo transcript sequence reconstruction from RNA-seq using the Trinity platform for reference generation and analysis. *Nat Protoc.* 8, 1494-1512, doi:10.1038/nprot.2013.084 (2013). PMCID: 3875132.

16 Hacisuleyman, E., Goff, L. A., Trapnell, C., Williams, A., Henao-Mejia, J., Sun, L., McClanahan, P., Hendrickson, D. G., Sauvageau, M., Kelley, D. R., Morse, M., Engreitz, J., Lander, E. S., Guttman, M., Lodish, H. F., Flavell, R., Raj, A. & Rinn, J. L. Topological organization of multichromosomal regions by the long intergenic noncoding RNA Firre. *Nat Struct Mol Biol.* 21, 198-206, doi: 10.1038/nsmb.2764 (2014). PMCID:3950333.

17 Heckl, D., Kowalczyk, M. S., Yudovich, D., Belizaire, R., Puram, R. V., McConkey, M. E., Thielke, A., Aster, J. C., Regev, A. & Ebert, B. L. Generation of mouse models of myeloid malignancy with combinatorial genetic lesions using CRISPR-Cas9 genome editing. *Nature biotechnology.* 32, 941-946, doi:10.1038/nbt.2951 (2014). PMCID: 4160386.

18 Jaitin, D. A., Kenigsberg, E., Keren-Shaul, H., Elefant, N., Paul, F., Zaretsky, I., Mildner, A., Cohen, N., Jung, S., Tanay, A. & Amit, I. Massively parallel single-cell RNA-seq for marker-free decomposition of tissues into cell types. *Science.* 343, 776-779, doi:10.1126/science.1247651 (2014). PMCID:4412462.

19 Jovanovic, M., Rooney, M. S., Mertins, P., Przybylski, D., Chevrier, N., Satija, R., Rodriguez, E. H., Fields, A. P., Schwartz, S., Raychowdhury, R., Mumbach, M. R., Eisenhaure, T., Rabani, M., Gennert, D., Lu, D., Delorey, T., Weissman, J. S., Carr, S. A., Hacohen, N. & Regev, A. Dynamic profiling of the protein life cycle in response to pathogens. *Science.* 347, 1259038, doi:10.1126/science.1259038 (2015). PMCID:PMC Journal—In Process.

20 Kearns, N. A., Genga, R. M., Enuameh, M. S., Garber, M., Wolfe, S. A. & Maehr, R. Cas9 effector-mediated regulation of transcription and differentiation in human pluripotent stem cells. *Development.* 141, 219-223, doi: 10.1242/dev.103341 (2014). PMCID:3865759.

21 Kelley, D. & Rinn, J. Transposable elements reveal a stem cell-specific class of long noncoding RNAs. *Genome Biol.* 13, R107, doi:10.1186/gb-2012-13-11-r107 (2012). PMCID:3580499.

22 Kumar, R. M., Cahan, P., Shalek, A. K., Satija, R., DaleyKeyser, A. J., Li, H., Zhang, J., Pardee, K., Gennert, D., Trombetta, J. J., Ferrante, T. C., Regev, A., Daley, G. Q. & Collins, J. J. Deconstructing transcriptional heterogeneity in pluripotent stem cells. *Nature.* 516, 56-61, doi:10.1038/nature13920 (2014). PMCID:4256722.

23 Lara-Astiaso, D., Weiner, A., Lorenzo-Vivas, E., Zaretsky, I., Jaitin, D. A., David, E., Keren-Shaul, H., Mildner, A., Winter, D., Jung, S., Friedman, N. & Amit, I. Immunogenetics. Chromatin state dynamics during blood formation. *Science.* 345, 943-949, doi:10.1126/science.1256271 (2014). PMCID:4412442.

24 Lee, M. N., Ye, C., Villani, A. C., Raj, T., Li, W., Eisenhaure, T. M., Imboywa, S. H., Chipendo, P. I., Ran, F. A., Slowikowski, K., Ward, L. D., Raddassi, K., McCabe, C., Lee, M. H., Frohlich, I. Y., Hafler, D. A., Kellis, M., Raychaudhuri, S., Zhang, F., Stranger, B. E., Benoist, C. O., De Jager, P. L., Regev, A. & Hacohen, N. Common genetic variants modulate pathogen-sensing responses in human dendritic cells. *Science.* 343, 1246980, doi:10.1126/science.1246980 (2014). PMCID: 4124741.

25 Macosko, E. Z., Basu, A., Satija, R., Nemesh, J., Goldman, M., Tirosh, I., Bialas, A. R., Kamitaki, N., Sanes, J. R., Weitz, D. A., Shalek, A. K., Regev, A. & McCarroll, S. A. Genome-wide expression profiling in thousands of individual neurons using nanoliter droplets. *Cell.* In Press (2015).

26 Na, Y. R., Kim, S. Y., Gaublomme, J. T., Shalek, A. K., Jorgolli, M., Park, H. & Yang, E. G. Probing enzymatic activity inside living cells using a nanowire-cell "sandwich" assay. *Nano Lett.* 13, 153-158, doi:10.1021/nl3037068 (2013). PMCID:3541459.

27 Parnas, O., Jovanovic, M., Eisenhaure, T. M., Herbst, R. H., Dixit, A., Ye, C., Przybylski, D., Platt, R. J., Tirosh, I., Sanjana, N. E., Shalem, O., Satija, R., Raychowdhury, R., Mertins, P., Carr, S. A., Zhang, F., Hacohen, N. & Regev, A. A genome-wide CRISPR screen in primary immune cells to dissect regulatory networks. *Cell.* In Press (2015).

28 Platt, R. J., Chen, S., Zhou, Y., Yim, M. J., Swiech, L., Kempton, H. R., Dahlman, J. E., Parnas, O., Eisenhaure, T. M., Jovanovic, M., Graham, D. B., Jhunjhunwala, S., Heidenreich, M., Xavier, R. J., Langer, R., Anderson, D. G., Hacohen, N., Regev, A., Feng, G., Sharp, P. A. & Zhang, F. CRISPR-Cas9 knockin mice for genome editing and cancer modeling. *Cell.* 159, 440-455, doi:10.1016/j.cell.2014.09.014 (2014). PMCID:4265475.

29 Rabani, M., Raychowdhury, R., Jovanovic, M., Rooney, M., Stumpo, D. J., Pauli, A., Hacohen, N., Schier, A. F., Blackshear, P. J., Friedman, N., Amit, I. & Regev, A. High-resolution sequencing and modeling identifies distinct dynamic RNA regulatory strategies. *Cell.* 159, 1698-1710, doi:10.1016/j.cell.2014.11.015 (2014). PMCID: 4272607.

30 Ram, O., Goren, A., Amit, I., Shoresh, N., Yosef, N., Ernst, J., Kellis, M., Gymrek, M., Issner, R., Coyne, M., Durham, T., Zhang, X., Donaghey, J., Epstein, C. B., Regev, A. & Bernstein, B. E. Combinatorial patterning of chromatin regulators uncovered by genome-wide location analysis in human cells. *Cell.* 147, 1628-1639, doi: 10.1016/j.cell.2011.09.057 (2011). PMCID:3312319.

31 Satija, R., Farrell, J. A., Gennert, D., Schier, A. F. & Regev, A. Spatial reconstruction of single-cell gene expression data. *Nature biotechnology.* 33, 495-502, doi: 10.1038/nbt.3192 (2015).

32 Sauvageau, M., Goff, L. A., Lodato, S., Bonev, B., Groff, A. F., Gerhardinger, C., Sanchez-Gomez, D. B., Hacisuleyman, E., Li, E., Spence, M., Liapis, S. C., Mallard, W., Morse, M., Swerdel, M. R., D'Ecclessis, M. F., Moore, J. C., Lai, V., Gong, G., Yancopoulos, G. D., Frendewey, D., Kellis, M., Hart, R. P., Valenzuela, D. M., Arlotta, P. & Rinn, J. L. Multiple knockout mouse models reveal lincRNAs are required for life and brain development. *eLife.* 2, e01749, doi:10.7554/eLife.01749 (2013). PMCID: 3874104.

33 Schwartz, S., Agarwala, S. D., Mumbach, M. R., Jovanovic, M., Mertins, P., Shishkin, A., Tabach, Y., Mikkelsen, T. S., Satija, R., Ruvkun, G., Carr, S. A., Lander, E. S., Fink, G. R. & Regev, A. High-resolution mapping reveals a conserved, widespread, dynamic mRNA methylation program in yeast meiosis. *Cell.* 155, 1409-1421, doi:10.1016/j.cell.2013.10.047 (2013). PMCID:3956118.

34 Schwartz, S., Bernstein, D. A., Mumbach, M. R., Jovanovic, M., Herbst, R. H., Leon-Ricardo, B. X., Engreitz, J. M., Guttman, M., Satija, R., Lander, E. S., Fink, G. & Regev, A. Transcriptome-wide mapping reveals widespread dynamic-regulated pseudouridylation of ncRNA and mRNA. *Cell.* 159, 148-162, doi:10.1016/j.cell.2014.08.028 (2014). PMCID: 4180118.

35 Schwartz, S., Mumbach, M. R., Jovanovic, M., Wang, T., Maciag, K., Bushkin, G. G., Mertins, P., Ter-Ovanesyan, D., Habib, N., Cacchiarelli, D., Sanjana, N. E., Freinkman, E., Pacold, M. E., Satija, R., Mikkelsen, T. S., Hacohen, N., Zhang, F., Carr, S. A., Lander, E. S. & Regev, A. Perturbation of m6A writers reveals two distinct classes of mRNA methylation at internal and 5' sites. *Cell reports.* 8, 284-296, doi:10.1016/j.celrep.2014.05.048 (2014). PMCID:4142486.

36 Shakya, A., Callister, C., Goren, A., Yosef, N., Garg, N., Khoddami, V., Nix, D., Regev, A. & Tantin, D. Pluripotency transcription factor Oct4 mediates stepwise nucleosome demethylation and depletion. *Mol Cell Biol.* 35, 1014-1025, doi:10.1128/MCB.01105-14 (2015). PMCID: 4333097.

37 Shalek, A. K., Gaublomme, J. T., Wang, L., Yosef, N., Chevrier, N., Andersen, M. S., Robinson, J. T., Pochet, N., Neuberg, D., Gertner, R. S., Amit, I., Brown, J. R., Hacohen, N., Regev, A., Wu, C. J. & Park, H. Nanowire-mediated delivery enables functional interrogation of primary immune cells: application to the analysis of chronic lymphocytic leukemia. *Nano Lett.* 12, 6498-6504, doi: 10.1021/nl3042917 (2012). PMCID:3573729.

38 Shalek, A. K., Satija, R., Adiconis, X., Gertner, R. S., Gaublomme, J. T., Raychowdhury, R., Schwartz, S., Yosef, N., Malboeuf, C., Lu, D., Trombetta, J. J., Gennert, D., Gnirke, A., Goren, A., Hacohen, N., Levin, J. Z., Park, H. & Regev, A. Single-cell transcriptomics reveals bimodality in expression and splicing in immune cells. *Nature.* 498, 236-240, doi:10.1038/nature12172 (2013). PMCID: 3683364.

39 Shalek, A. K., Satija, R., Shuga, J., Trombetta, J. J., Gennert, D., Lu, D., Chen, P., Gertner, R. S., Gaublomme, J. T., Yosef, N., Schwartz, S., Fowler, B., Weaver, S., Wang, J., Wang, X., Ding, R., Raychowdhury, R., Friedman, N., Hacohen, N., Park, H., May, A. P. & Regev, A. Single-cell RNA-seq reveals dynamic paracrine control of cellular variation. *Nature.* 510, 363-369, doi:10.1038/nature13437 (2014). PMCID:4193940.

40 Smith, Z. D., Chan, M. M., Humm, K. C., Karnik, R., Mekhoubad, S., Regev, A., Eggan, K. & Meissner, A. DNA methylation dynamics of the human preimplantation embryo. *Nature.* 511, 611-615, doi:10.1038/nature13581 (2014). PMCID:4178976.

41 Smith, Z. D., Chan, M. M., Mikkelsen, T. S., Gu, H., Gnirke, A., Regev, A. & Meissner, A. A unique regulatory phase of DNA methylation in the early mammalian embryo. *Nature.* 484, 339-344, doi:10.1038/nature10960 (2012). PMCID:3331945.

42 Sun, L., Goff, L. A., Trapnell, C., Alexander, R., Lo, K. A., Hacisuleyman, E., Sauvageau, M., Tazon-Vega, B., Kelley, D. R., Hendrickson, D. G., Yuan, B., Kellis, M., Lodish, H. F. & Rinn, J. L. Long noncoding RNAs regulate adipogenesis. *Proceedings of the National Academy of Sciences of the United States of America.* 110, 3387-3392, doi:10.1073/pnas.1222643110 (2013). PMCID:3587215.

43 Trapnell, C., Cacchiarelli, D., Grimsby, J., Pokharel, P., Li, S., Morse, M., Lennon, N. J., Livak, K. J., Mikkelsen, T. S. & Rinn, J. L. The dynamics and regulators of cell fate decisions are revealed by pseudotemporal ordering of single cells. *Nature biotechnology.* 32, 381-386, doi: 10.1038/nbt.2859 (2014). PMCID:4122333.

44 Trapnell, C., Hendrickson, D. G., Sauvageau, M., Goff, L., Rinn, J. L. & Pachter, L. Differential analysis of gene regulation at transcript resolution with RNA-seq. *Nature biotechnology.* 31, 46-53, doi:10.1038/nbt.2450 (2013). PMCID:3869392.

45 Trombetta, J. J., Gennert, D., Lu, D., Satija, R., Shalek, A. K. & Regev, A. Preparation of Single-Cell RNA-Seq Libraries for Next Generation Sequencing. *Curr Protoc Mol Biol.* 107, 4 22 21-24 22 17, doi:10.1002/0471142727.mb0422s107 (2014). PMCID:4338574.

46 Wang, L., Shalek, A. K., Lawrence, M., Ding, R., Gaublomme, J. T., Pochet, N., Stojanov, P., Sougnez, C., Shukla, S. A., Stevenson, K. E., Zhang, W., Wong, J., Sievers, Q. L., MacDonald, B. T., Vartanov, A. R., Goldstein, N. R., Neuberg, D., He, X., Lander, E., Hacohen, N., Regev, A., Getz, G., Brown, J. R., Park, H. & Wu, C. J. Somatic mutation as a mechanism of Wnt/beta-catenin pathway activation in CLL. *Blood.* 124, 1089-1098, doi: 10.1182/blood-2014-01-552067 (2014). PMCID: 4133483.

47 Washietl, S., Kellis, M. & Garber, M. Evolutionary dynamics and tissue specificity of human long noncoding RNAs in six mammals. *Genome Res.* 24, 616-628, doi: 10.1101/gr.165035.113 (2014). PMCID:3975061.

48 Wu, C., Yosef, N., Thalhamer, T., Zhu, C., Xiao, S., Kishi, Y., Regev, A. & Kuchroo, V. K. Induction of pathogenic TH17 cells by inducible salt-sensing kinase SGK1. *Nature.* 496, 513-517, doi:10.1038/nature11984 (2013). PMCID:3637879.

49 Yosef, N., Shalek, A. K., Gaublomme, J. T., Jin, H., Lee, Y., Awasthi, A., Wu, C., Karwacz, K., Xiao, S., Jorgolli, M., Gennert, D., Satija, R., Shakya, A., Lu, D. Y., Trombetta, J. J., Pillai, M. R., Ratcliffe, P. J., Coleman, M. L., Bix, M., Tantin, D., Park, H., Kuchroo, V. K. & Regev, A. Dynamic regulatory network controlling TH17 cell differentiation. *Nature.* 496, 461-468, doi:10.1038/nature11981 (2013). PMCID:3637864.

50 Assarsson, E., Lundberg, M., Holmquist, G., Bjorkesten, J., Thorsen, S. B., Ekman, D., Eriksson, A., Rennel Dickens, E., Ohlsson, S., Edfeldt, G., et al. (2014). Homogenous 96-plex PEA immunoassay exhibiting high sensitivity, specificity, and excellent scalability. PloS one 9, e95192.

51 Bendall, S. C., Simonds, E. F., Qiu, P., Amir el, A. D., Krutzik, P. O., Finck, R., Bruggner, R. V., Melamed, R., Trejo, A., Ornatsky, O. I., et al. (2011). Single-cell mass cytometry of differential immune and drug responses across a human hematopoietic continuum. Science 332, 687-696.

52 Chung, K., Wallace, J., Kim, S. Y., Kalyanasundaram, S., Andalman, A. S., Davidson, T. J., Mirzabekov, J. J., Zalocusky, K. A., Mattis, J., Denisin, A. K., et al. (2013). Structural and molecular interrogation of intact biological systems. Nature 497, 332-337.

53 Fan, H. C., Fu, G. K., and Fodor, S. P. (2015). Expression profiling. Combinatorial labeling of single cells for gene expression cytometry. Science 347, 1258367.

54 Gomez, D., Shankman, L. S., Nguyen, A. T., and Owens, G. K. (2013). Detection of histone modifications at specific gene loci in single cells in histological sections. Nature methods 10, 171-177.

55 Janssen, K. P., Knez, K., Spasic, D., and Lammertyn, J. (2013). Nucleic acids for ultra-sensitive protein detection. Sensors 13, 1353-1384.

56 Kantlehner, M., Kirchner, R., Hartmann, P., Ellwart, J. W., Alunni-Fabbroni, M., and Schumacher, A. (2011). A high-throughput DNA methylation analysis of a single cell. Nucleic acids research 39, e44.

57 Lorthongpanich, C., Cheow, L. F., Balu, S., Quake, S. R., Knowles, B. B., Burkholder, W. F., Solter, D., and Messerschmidt, D. M. (2013). Single-cell DNA-methylation analysis reveals epigenetic chimerism in preimplantation embryos. Science 341, 1110-1112.

58 Nagano, T., Lubling, Y., Stevens, T. J., Schoenfelder, S., Yaffe, E., Dean, W., Laue, E. D., Tanay, A., and Fraser, P. (2013). Single-cell Hi-C reveals cell-to-cell variability in chromosome structure. Nature 502, 59-64.

59 Pardon, E., Laeremans, T., Triest, S., Rasmussen, S. G., Wohlkonig, A., Ruf, A., Muyldermans, S., Hol, W. G., Kobilka, B. K., and Steyaert, J. (2014). A general protocol for the generation of Nanobodies for structural biology. Nature protocols 9, 674-693.

60 Perfetto, S. P., Chattopadhyay, P. K., and Roederer, M. (2004). Seventeen-colour flow cytometry: unravelling the immune system. Nature reviews Immunology 4, 648-655.

61 Shalek, A. K., Satija, R., Shuga, J., Trombetta, J. J., Gennert, D., Lu, D., Chen, P., Gertner, R. S., Gaublomme, J. T., Yosef, N., et al. (2014). Single-cell RNA-seq reveals dynamic paracrine control of cellular variation. Nature 509, 363-369.

62 Theile, C. S., Witte, M. D., Blom, A. E., Kundrat, L., Ploegh, H. L., and Guimaraes, C. P. (2013). Site-specific N-terminal labeling of proteins using sortase-mediated reactions. Nature protocols 8, 1800-1807.

What is claimed is:

1. A method of assaying single cells or aggregations of cellular constituents from single cells, comprising:
   (a) segregating a plurality of single cells or single aggregations of cellular constituents, each from a single cell, into separate reaction vessels comprising monomers of a polymerizable gel and a fixing agent;
   (b) polymerizing the gel to embed the plurality of single cells or single aggregations of cellular constituents from single cells in discrete polymer matrices, whereby the cellular constituents of the single cells or aggregations are embedded in the discrete polymer matrices;
   (c) pooling the discrete polymer matrices into a single reaction vessel;
   (d) incubating the cellular constituents embedded in the pooled polymer matrices with one or more labeling ligands with specific binding affinity for one or more target cellular constituents to produce one or more labeled cellular constituents in the polymer matrices, wherein each of the one or more labeling ligands comprise a bound oligonucleotide label comprising a unique constituent identifier (UCI) sequence specific for identifying the labeling ligand, wherein the UCI comprises 4 to 30 nucleotides,
   optionally, wherein the oligonucleotide label further comprises a unique molecular identifier (UMI) sequence comprising 4-20 nucleotides,
   wherein the cellular constituents comprise a protein, RNA, and/or a DNA molecule,
   and wherein the incubation comprises binding conditions under which the one or more labeling ligands will bind to the cellular constituents within the polymer matrices, and the incubation further comprises washing the polymer matrices to remove unbound labeling ligands from the polymer matrices; and
   (e) sequencing the oligonucleotide labels for single polymer matrices, optionally amplifying the oligonucleotide labels before sequencing, whereby detecting the UCI by sequencing indicates the presence of the target cellular constituent in the segregated aggregations of cellular constituents.

2. The method of claim 1, further comprising segregating the discrete polymer matrices comprising the labeled constituents after incubating in step (d) and before sequencing in step (e),
   wherein segregating the discrete polymer matrices comprises sorting single discrete matrices into separate reaction vessels; or
   wherein segregating the discrete polymer matrices comprises forming discrete unique-identifier-transfer compositions, each comprising the cellular constituents embedded in a discrete polymer matrix and a transfer particle, wherein:
      (a) the oligonucleotide label further comprises a capture sequence, and the UCI and capture sequence are together releasably attached to the labeling ligand;
      (b) the labelling ligand is bound to the target cellular constituent; and,
      (c) the transfer particle comprises:
         (i) a capture-binding-sequence having specific binding affinity for the capture sequence attached to the UCI, and,
         (ii) a unique source identifier (USI) sequence that is unique to each transfer particle; and
   wherein the method further comprises releasing the UCI from the labeled ligand, under conditions within the unique-identifier-transfer composition so that the released capture sequence binds to the capture-binding-sequence on the transfer particle, thereby transferring the UCI to the transfer particle.

3. The method of claim 2, wherein segregating the discrete polymer matrices into separate reaction vessels further comprises generating a USI for each discrete polymer matrix by a split pool method,
   wherein the oligonucleotide label further comprises a universal ligation handle (ULH) sequence capable of hybridization to a complementary sequence on a first index nucleotide sequence,
   optionally, wherein the ligation handle comprises a restriction site for producing a sequence complementary with a first index sequence, and wherein the method further comprises digestion with a restriction enzyme,
   optionally, wherein the ligation handle comprises a nucleotide sequence complementary with a ligation primer sequence and wherein the sequence complementary with a first index sequence is produced by hybridization of the ligation primer to the ligation handle,
   wherein the first index nucleotide sequence comprises a sequence complementary to a final index sequence or a middle index sequence,
   wherein the middle index sequence comprises a sequence complementary to the first index sequence and to the final index sequence or optionally to another middle index sequence and final index sequence,
   wherein the final index sequence has a sequence complementary to the preceding index sequence,
   wherein the first, middle, and final index sequences are selected from a plurality of unique sequences comprising compatible DNA sequences for hybridization and 10 to 30 base pairs of unique sequence,
   optionally, wherein either the first, middle, or final index sequence further comprises a unique molecular identifier (UMI) sequence comprising 4-20 nucleotides, and
   wherein the split pool method comprises:
      (a) splitting the pool of discrete polymer matrices into separate pools of polymer matrices, each containing a unique first index sequence;
      (b) ligating the first index sequence to the ligation handle or hybridizing and extending the first index sequence on the ligation handle;
      (c) pooling the discrete polymer matrices;
      (d) optionally,
         (i) splitting the pool of discrete polymer matrices into separate pools each containing a unique middle index sequence;
         (ii) ligating the middle index sequence to the first index sequence or hybridizing and extending the middle index sequence on the first index; and
         (iii) pooling the discrete polymer matrices;
      (e) optionally, repeating step (d) with another middle index sequence;
      (f) splitting the pool of discrete polymer matrices into pools containing a unique final index sequence; and
      (g) ligating the final index sequence to the preceding index sequence or hybridizing and extending the final index sequence on the preceding index sequence index,
   whereby each discrete polymer matrix comprises a USI comprising a combination of indexes.

4. The method of claim 1, wherein the aggregation of cellular constituents is an extracellular vesicle, an organelle, or an organized subcomponent thereof.

5. The method of claim 1, wherein the steps of (a) segregating and (b) polymerizing is carried out in an aqueous aliquot or in a droplet formed by an aqueous solution in oil emulsion, and/or
   wherein the polymer matrix is a hydrogel, and/or
   wherein the method is a multiplex assay with a plurality of labeling ligands, each labeling ligand having a distinct UCI, and/or
   wherein the labeling ligand is non-covalently bound to the target cellular constituent, and/or
   wherein the method further comprises treating the cellular constituents embedded in the polymer matrices with a detergent so as to remove lipids from the polymer matrices before incubating the cellular constituents with the labeling ligand, and/or
   wherein the method further comprises quantitating the relative differences in the amount of a cellular constituent between aggregations of cellular constituents.

6. The method of claim 2, further comprising pooling the oligonucleotide labels comprising a USI from the plurality of polymer matrices and sequencing the pooled UCI sequences and USI sequences, or
   further comprising pooling the oligonucleotide labels comprising a USI and UMI from a plurality of polymer matrices and sequencing the pooled UCI sequences, USI sequences, and UMI sequences.

7. The method of claim 1, wherein the labeling ligand is an antibody or an antibody fragment, an aptamer, or an oligonucleotide sequence configured to hybridize to a transcript specific region or guide RNA sequence.

8. The method of claim 7, wherein at least two distinct labeling ligands comprise complementary oligonucleotide sequences, so that binding of the labeling ligands to respective target cellular constituents that are in proximity permits the complementary sequences of the distinct ligands to hybridize, forming an amplifiable polynucleotide duplex, or
   wherein at least two distinct labeling ligands comprise oligonucleotide sequences configured to be ligated, so that binding of the labeling ligands to respective target cellular constituents that are in proximity permits the oligonucleotide sequences of the distinct ligands to ligate, forming an amplifiable polynucleotide duplex;

optionally, wherein one of the labeling ligands comprises a restriction enzyme site between the labeling ligand and the oligonucleotide label, and wherein the method further comprises treating with a restriction enzyme, whereby the UCI from said labeling ligand is transferred to the oligonucleotide label of the labeling ligand in proximity; and wherein the method further comprises amplifying the polynucleotide duplex to provide an amplified sequence that is a detectable signal that target cellular constituents are in proximity.

9. The method of claim 1, further comprising labeling the aggregation of cellular constituents by fluorescent in situ hybridization.

10. The method of claim 1, wherein the aggregation of cellular constituents is a cell that is a member of a cell population, and the method further comprises transforming or transducing the cell population with one or more genomic sequence-perturbation constructs that perturb a genomic sequence in the cells, wherein each distinct genomic sequence-perturbation construct comprises a unique-perturbation-identified (UPI) sequence unique to that construct.

11. The method of claim 1, wherein the oligonucleotide label comprises a regulatory sequence configured for amplification by T7 polymerase, wherein before sequencing the method further comprises T7 amplification of the oligonucleotide label followed by subsequent cDNA generation, and optionally amplification by PCR.

12. The method of claim 1, wherein the oligonucleotide label further comprises at least one spacer sequence, and/or
   wherein the oligonucleotide label further comprises a photocleavable linker, and/or
   wherein the oligonucleotide label further comprises a restriction enzyme site between the labeling ligand and UCI.

13. The method of claim 1, wherein the polymer matrices further comprise magnetic particles.

14. The method of claim 1, wherein the oligonucleotide label comprises one or more iso-dG and/or iso-dC nucleotides.

15. The method of claim 1, wherein the fixing agent is selected from the group consisting of formaldehyde, paraformaldehyde and glutaraldehyde.

16. The method of claim 2, wherein the USI comprises 4-15 nucleotides.

17. The method of claim 7, wherein the antibody or an antibody fragment is a nanobody, Fab, Fab', (Fab')2, Fv, ScFv, diabody, triabody, tetrabody, Bis-scFv, minibody, Fab2, or Fab3 fragment.

18. The method of claim 10, wherein the genomic sequence-perturbation construct comprises a sequence encoding a guide RNA sequence of a CRISPR-Cas targeting system.

* * * * *